United States Patent
De La Rosa et al.

(10) Patent No.: US 10,906,924 B2
(45) Date of Patent: Feb. 2, 2021

(54) MODULATORS OF INDOLEAMINE 2,3-DIOXYGENASE

(71) Applicant: GLAXOSMITHKLINE INTELLECTUAL PROPERTY DEVELOPMENT LIMITED, Brentford (GB)

(72) Inventors: Martha Alicia De La Rosa, Research Triangle Park, NC (US); Hongfeng Deng, Cambridge, MA (US); Ghotas Evindar, Cambridge, MA (US); Wieslaw Mieczyslaw Kazmierski, Research Triangle Park, NC (US); John Franklin Miller, Research Triangle Park, NC (US); Vicente Samano, Research Triangle Park, NC (US); Yoshiaki Washio, Stevenage (GB); Bing Xia, Cambridge, MA (US)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 16/618,537

(22) PCT Filed: Jun. 27, 2018

(86) PCT No.: PCT/IB2018/054767
§ 371 (c)(1),
(2) Date: Dec. 2, 2019

(87) PCT Pub. No.: WO2019/003148
PCT Pub. Date: Jan. 3, 2019

(65) Prior Publication Data
US 2020/0165280 A1  May 28, 2020

Related U.S. Application Data

(60) Provisional application No. 62/666,779, filed on May 4, 2018, provisional application No. 62/525,892, filed on Jun. 28, 2017.

(51) Int. Cl.
C07F 9/6561 (2006.01)
C07D 491/107 (2006.01)
C07D 491/20 (2006.01)

(52) U.S. Cl.
CPC ........ *C07F 9/6561* (2013.01); *C07D 491/107* (2013.01); *C07D 491/20* (2013.01)

(58) Field of Classification Search
CPC .. C07F 9/6561; C07D 491/107; C07D 491/20
See application file for complete search history.

(56) References Cited

U.S. PATENT DOCUMENTS

2016/0120841 A1* 5/2016 Kym ............... A61K 31/4433
514/210.18

FOREIGN PATENT DOCUMENTS

WO   WO 2016/071293 A2   5/2016

OTHER PUBLICATIONS

Database Registry, Database Accession Nos. 1958364-90-3 to 879311-52-1: Compounds 1 to 323 of 323.
Database Registry [Online], Chemical Abstracts Service, Columbus, OH. Jul. 6, 2016, XP002784260, Database Accession No. 1946239-95-7.
Database Registry [Online], Chemical Abstracts Service, Columbus, OH. May 13, 2010, XP002784261, Database Accession No. 1222907-21-2.
Database Registry [Online], Chemical Abstracts Service, Columbus, OH. Apr. 10, 2014, XP002784262, Database Accession No. 1582629-94-4.
Database Registry [Online], Chemical Abstracts Service, Columbus, OH. Apr. 29, 2011, XP002784263, Database Accession No. 1287476-77-0.
Database Registry [Online], Chemical Abstracts Service, Columbus, OH. Jul. 4, 2016, XP002784264, Database Accession No. 1944538-48-0.
R. Dolusic. "Indoleamine 2,3-dioxygenase inhibitors: a patent review (2008-2012)". Expert Opin. Ther. Patents, 23(10): 1367-1381, Aug. 30, 2013.

* cited by examiner

*Primary Examiner* — Timothy R Rozof
(74) *Attorney, Agent, or Firm* — Robert H. Brink; Duke M. Fitch; Edward R. Gimmi

(57) ABSTRACT

Provided are IDO inhibitor compounds of Formula I and pharmaceutically acceptable salts thereof, their pharmaceutical compositions, their methods of preparation, and methods for their use in the prevention and/or treatment of diseases.

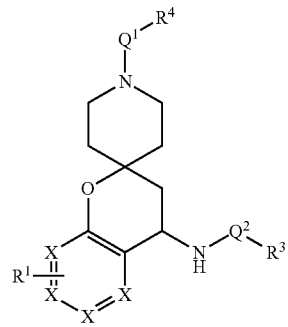

Formula I

17 Claims, No Drawings

MODULATORS OF INDOLEAMINE 2,3-DIOXYGENASE

This application is a § 371 of International Application No. PCT/IB2018/054767, filed 27 Jun. 2018, which claims the benefit of U.S. Provisional Application Nos. 62/666,779, filed 4 May 2018, and 62/525,892, filed 28 Jun. 2017.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase compounds in therapeutically effective amounts are disclosed. Methods for preparing such compounds and methods of using the compounds and pharmaceutical compositions thereof are also disclosed.

BACKGROUND OF THE INVENTION

Indoleamine-2,3-dioxygenase 1 (IDO1) is a heme-containing enzyme that catalyzes the oxidation of the indole ring of tryptophan to produce N-formyl kynurenine, which is rapidly and constitutively converted to kynurenine (Kyn) and a series of downstream metabolites. IDO1 is the rate limiting step of this kynurenine pathway of tryptophan metabolism and expression of IDO1 is inducible in the context of inflammation. Stimuli that induce IDO1 include viral or bacterial products, or inflammatory cytokines associated with infection, tumors, or sterile tissue damage. Kyn and several downstream metabolites are immunosuppressive: Kyn is antiproliferative and proapoptotic to T cells and NK cells (Munn, Shafizadeh et al. 1999, Frumento, Rotondo et al. 2002) while metabolites such as 3-hydroxy anthranilic acid (3-HAA) or the 3-HAA oxidative dimerization product cinnabarinic acid (CA) inhibit phagocyte function (Sekkai, Guittet et al. 1997), and induce the differentiation of immunosuppressive regulatory T cells (Treg) while inhibiting the differentiation of gut-protective IL-17 or IL-22-producing CD4+ T cells (Th17 and Th22)(Favre, Mold et al. 2010). IDO1 induction, among other mechanisms, is likely important in limiting immunopathology during active immune responses, in promoting the resolution of immune responses, and in promoting fetal tolerance. However in chronic settings, such as cancer, or chronic viral or bacterial infection, IDO1 activity prevents clearance of tumor or pathogen and if activity is systemic, IDO1 activity may result in systemic immune dysfunction (Boasso and Shearer 2008, Li, Huang et al. 2012). In addition to these immunomodulatory effects, metabolites of IDO1 such as Kyn and quinolinic acid are also known to be neurotoxic and are observed to be elevated in several conditions of neurological dysfunction and depression. As such, IDO1 is a therapeutic target for inhibition in a broad array of indications, such as to promote tumor clearance, enable clearance of intractable viral or bacterial infections, decrease systemic immune dysfunction manifest as persistent inflammation during HIV infection or immunosuppression during sepsis, and prevent or reverse neurological conditions.

IDO1 and Persistent Inflammation in HIV Infection:

Despite the success of antiretroviral therapy (ART) in suppressing HIV replication and decreasing the incidence of AIDS-related conditions, HIV-infected patients on ART have a higher incidence of non-AIDS morbidities and mortality than their uninfected peers. These non-AIDS conditions include cancer, cardiovascular disease, osteoporosis, liver disease, kidney disease, frailty, and neurocognitive dysfunction (Deeks 2011). Several studies indicate that non-AIDS morbidity/mortality is associated with persistent inflammation, which remains elevated in HIV-infected patients on ART as compared to peers (Deeks 2011). As such, it is hypothesized that persistent inflammation and immune dysfunction despite virologic suppression with ART is a cause of these non-AIDS-defining events (NADEs).

HIV infects and kills CD4+ T cells, with particular preference for cells like those CD4+ T cells that reside in the lymphoid tissues of the mucosal surfaces (Mattapallil, Douek et al. 2005). The loss of these cells combined with the inflammatory response to infection result in a perturbed relationship between the host and all pathogens, including HIV itself, but extending to pre-existing or acquired viral infections, fungal infections, and resident bacteria in the skin and mucosal surfaces. This dysfunctional host:pathogen relationship results in the over-reaction of the host to what would typically be minor problems as well as permitting the outgrowth of pathogens among the microbiota. The dysfunctional host:pathogen interaction therefore results in increased inflammation, which in turn leads to deeper dysfunction, driving a vicious cycle. As inflammation is thought to drive non-AIDS morbidity/mortality, the mechanisms governing the altered host:pathogen interaction are therapeutic targets.

IDO1 expression and activity are increased during untreated and treated HIV infection as well as in primate models of SIV infection (Boasso, Vaccari et al. 2007, Favre, Lederer et al. 2009, Byakwaga, Boum et al. 2014, Hunt, Sinclair et al. 2014, Tenorio, Zheng et al. 2014). IDO1 activity, as indicated by the ratio of plasma levels of enzyme substrate and product (Kyn/Tryp or K:T ratio), is associated with other markers of inflammation and is one of the strongest predictors of non-AIDS morbidity/mortality (Byakwaga, Boum et al. 2014, Hunt, Sinclair et al. 2014, Tenorio, Zheng et al. 2014). In addition, features consistent with the expected impact of increased IDO1 activity on the immune system are major features of HIV and SIV induced immune dysfunction, such as decreased T cell proliferative response to antigen and imbalance of Treg:Th17 in systemic and intestinal compartments (Favre, Lederer et al. 2009, Favre, Mold et al. 2010). As such, we and others hypothesize that IDO1 plays a role in driving the vicious cycle of immune dysfunction and inflammation associated with non-AIDS morbidity/mortality. Thus, we propose that inhibiting IDO1 will reduce inflammation and decrease the risk of NADEs in ART-suppressed HIV-infected persons.

IDO1 and Persistent Inflammation Beyond HIV

As described above, inflammation associated with treated chronic HIV infection is a likely driver of multiple end organ diseases [Deeks 2011]. However, these end organ diseases are not unique to HIV infection and are in fact the common diseases of aging that occur at earlier ages in the HIV-infected population. In the uninfected general population inflammation of unknown etiology is a major correlate of morbidity and mortality [Pinti, 2016 #88]. Indeed many of the markers of inflammation are shared, such as IL-6 and CRP. If, as hypothesized above, IDO1 contributes to persistent inflammation in the HIV-infected population by inducing immune dysfunction in the GI tract or systemic tissues, then IDO1 may also contribute to inflammation and therefore end organ diseases in the broader population. These inflammation-associated end organ diseases are exemplified by cardiovascular diseases, metabolic syndrome, liver disease (NAFLD, NASH), kidney disease, osteoporosis, and neurocognitive impairment. Indeed, the IDO1 pathway has links in the literature to liver disease (Vivoli abstracts at Italian Assoc. for the Study of the Liver Conference 2015], diabetes [Baban, 2010 #89], chronic kidney disease [Schefold, 2009 #90], cardiovascular disease [Mangge, 2014 #92; Mangge, 2014 #91], as well as general aging and all cause mortality [Pertovaara, 2006 #93]. As such, inhibition of IDO1 may have application in decreasing inflammation in the general population to decrease the incidence of specific end organ diseases associated with inflammation and aging.

IDO1 and Oncology

IDO expression can be detected in a number of human cancers (for example; melanoma, pancreatic, ovarian, AML, CRC, prostate and endometrial) and correlates with poor prognosis (Munn 2011). Multiple immunosuppressive roles have been ascribed to the action of IDO, including the induction of Treg differentiation and hyper-activation, suppression of Teff immune response, and decreased DC function, all of which impair immune recognition and promote tumor growth (Munn 2011). IDO expression in human brain tumors is correlated with reduced survival. Orthotropic and transgenic glioma mouse models demonstrate a correlation between reduced IDO expression and reduced Treg infiltration and an increased long term survival (Wainwright, Balyasnikova et al. 2012). In human melanoma a high proportion of tumors (33 of 36 cases) displayed elevated IDO suggesting an important role in establishing an immunosuppressive tumor microenvironment (TME) characterized by the expansion, activation and recruitment of MDSCs in a Treg-dependent manner (Holmgaard, Zamarin et al. 2015). Additionally, host IDO expressing immune cells have been identified in the draining lymph nodes and in the tumors themselves (Mellor and Munn 2004). Hence, both tumor and host-derived IDO are believed to contribute to the immune suppressed state of the TME.

The inhibition of IDO was one of the first small molecule drug strategies proposed for re-establishment of an immunogenic response to cancer (Mellor and Munn 2004). The d-enantiomer of 1-methyl tryptophan (D-1 MTor indoximod) was the first IDO inhibitor to enter clinical trials. While this compound clearly does inhibit the activity of IDO, it is a very weak inhibitor of the isolated enzyme and the in vivo mechanism(s) of action for this compound are still being elucidated. Investigators at Incyte optimized a hit compound obtained from a screening process into a potent and selective inhibitor with sufficient oral exposure to demonstrate a delay in tumor growth in a mouse melanoma model (Yue, Douty et al. 2009). Further development of this series led to INCB204360 which is a highly selective for inhibition of IDO-1 over IDO-2 and TDO in cell lines transiently transfected with either human or mouse enzymes (Liu, Shin et al. 2010). Similar potency was seen for cell lines and primary human tumors which endogenously express IDO1 (IC50s~3-20 nM). When tested in co-culture of DCs and naïve CD4$^+$CD25$^-$ T cells, INCB204360 blocked the conversion of these T cells into CD4$^+$FoxP3$^+$ Tregs. Finally, when tested in a syngeneic model (PAN02 pancreatic cells) in immunocompetent mice, orally dosed INCB204360 provided a significant dose-dependent inhibition of tumor growth, but was without effect against the same tumor implanted in immune-deficient mice. Additional studies by the same investigators have shown a correlation of the inhibition of IDO1 with the suppression of systemic kynurenine levels and inhibition of tumor growth in an additional syngeneic tumor model in immunocompetent mice. Based upon these preclinical studies, INCB24360 entered clinical trials for the treatment of metastatic melanoma (Beatty, O'Dwyer et al. 2013).

In light of the importance of the catabolism of tryptophan in the maintenance of immune suppression, it is not surprising that overexpression of a second tryptophan metabolizing enzyme, TDO2, by multiple solid tumors (for example, bladder and liver carcinomas, melanomas) has also been detected. A survey of 104 human cell lines revealed 20/104 with TDO expression, 17/104 with IDO1 and 16/104 expressing both (Pilotte, Larrieu et al. 2012). Similar to the inhibition of IDO1, the selective inhibition of TDO2 is effective in reversing immune resistance in tumors overexpressing TDO2 (Pilotte, Larrieu et al. 2012). These results support TDO2 inhibition and/or dual TDO2/IDO1 inhibition as a viable therapeutic strategy to improve immune function.

Multiple pre-clinical studies have demonstrated significant, even synergistic, value in combining IDO-1 inhibitors in combination with T cell checkpoint modulating mAbs to CTLA-4, PD-1, and GITR. In each case, both efficacy and related PD aspects of improved immune activity/function were observed in these studies across a variety of murine models (Balachandran, Cavnar et al. 2011, Holmgaard, Zamarin et al. 2013, M. Mautino 2014, Wainwright, Chang et al. 2014). The Incyte IDO1 inhibitor (INCB204360, epacadostat) has been clinically tested in combination with a CTLA4 blocker (ipilimumab), but it is unclear that an effective dose was achieved due to dose-limited adverse events seen with the combination. In contrast recently released data for an on-going trial combining epacadostat with Merck's PD-1 mAb (pembrolizumab) demonstrated improved tolerability of the combination allowing for higher doses of the IDO1 inhibitor. There have been several clinical responses across various tumor types which is encouraging. However, it is not yet known if this combination is an improvement over the single agent activity of pembrolizumab (Gangadhar, Hamid et al. 2015). Similarly, Roche/Genentech are advancing NGL919/GDC-0919 in combination with both mAbs for PD-L1 (MPDL3280A, Atezo) and OX-40 following the recent completion of a phase 1a safety and PK/PD study in patients with advanced tumors.

IDO1 and Chronic Infections

IDO1 activity generates kynurenine pathway metabolites such as Kyn and 3-HAA that impair at least T cell, NK cell, and macrophage activity (Munn, Shafizadeh et al. 1999, Frumento, Rotondo et al. 2002) (Sekkai, Guittet et al. 1997, Favre, Mold et al. 2010). Kyn levels or the Kyn/Tryp ratio are elevated in the setting of chronic HIV infection (Byakwaga, Boum et al. 2014, Hunt, Sinclair et al. 2014, Tenorio, Zheng et al. 2014), HBV infection (Chen, Li et al. 2009), HCV infection (Larrea, Riezu-Boj et al. 2007, Asghar, Ashiq et al. 2015), and TB infection (Suzuki, Suda et al. 2012) and are associated with antigen-specific T cell dysfunction (Boasso, Herbeuval et al. 2007, Boasso, Hardy et al. 2008, Loughman and Hunstad 2012, Ito, Ando et al. 2014, Lepiller, Soulier et al. 2015). As such, it is thought that in these cases of chronic infection, IDO1-mediated inhibition of the pathogen-specific T cell response plays a role in the persistence of infection, and that inhibition of IDO1 may have a benefit in promoting clearance and resolution of infection.

IDO1 and Sepsis

IDO1 expression and activity are observed to be elevated during sepsis and the degree of Kyn or Kyn/Tryp elevation corresponded to increased disease severity, including mortality (Tattevin, Monnier et al. 2010, Darcy, Davis et al. 2011). In animal models, blockade of IDO1 or IDO1 genetic knockouts protected mice from lethal doses of LPS or from mortality in the cecal ligation/puncture model (Jung, Lee et al. 2009, Hoshi, Osawa et al. 2014). Sepsis is characterized by an immunosuppressive phase in severe cases (Hotchkiss, Monneret et al. 2013), potentially indicating a role for IDO1 as a mediator of immune dysfunction, and indicating that pharmacologic inhibition of IDO1 may provide a clinical benefit in sepsis.

IDO1 and Neurological Disorders

In addition to immunologic settings, IDO1 activity is also linked to disease in neurological settings (reviewed in Lovelace Neuropharmacology 2016 (Lovelace, Varney et al. 2016)). Kynurenine pathway metabolites such as 3-hydroxykynurenine and quinolinic acid are neurotoxic, but are balanced by alternative metabolites kynurenic acid or picolinic acid, which are neuroprotective. Neurodegenerative and psychiatric disorders in which kynurenine pathway metabolites have been demonstrated to be associated with disease include multiple sclerosis, motor neuron disorders such as amyotrophic lateral sclerosis, Huntington's disease, Parkinson's disease, Alzheimer's disease, major depressive disorder, schizophrenia, anorexia (Lovelace, Varney et al. 2016). Animal models of neurological disease have shown some impact of weak IDO1 inhibitors such as 1-methyltryptophan on disease, indicating that IDO1 inhibition may provide clinical benefit in prevention or treatment of neurological and psychiatric disorders.

It would therefore be an advance in the art to discover IDO inhibitors that effective the balance of the aforementioned properties as a disease modifying therapy in chronic HIV infections to decrease the incidence of non-AIDS morbidity/mortality; and/or a disease modifying therapy to prevent mortality in sepsis; and/or an immunotherapy to enhance the immune response to HIV, HBV, HCV and other chronic viral infections, chronic bacterial infections, chronic fungal infections, and to tumors; and/or for the treatment of depression or other neurological/neuropsychiatric disorders.

Asghar, K., M. T. Ashiq, B. Zulfiqar, A. Mahroo, K. Nasir and S. Murad (2015). "Indoleamine 2,3-dioxygenase expression and activity in patients with hepatitis C virus-induced liver cirrhosis." *Exp Ther Med* 9(3): 901-904.

Balachandran, V. P., M. J. Cavnar, S. Zeng, Z. M. Bamboat, L. M. Ocuin, H. Obaid, E. C. Sorenson, R. Popow, C. Ariyan, F. Rossi, P. Besmer, T. Guo, C. R. Antonescu, T. Taguchi, J. Yuan, J. D. Wolchok, J. P. Allison and R. P. Dematteo (2011). "Imatinib potentiates antitumor T cell responses in gastrointestinal stromal tumor through the inhibition of Ido." *Nature Medicine* 17(9): 1094-1100.

Beatty, G. L., P. J. O'Dwyer, J. Clark, J. G. Shi, R. C. Newton, R. Schaub, J. Maleski, L. Leopold and T. Gajewski (2013). "Phase I study of the safety, pharmacokinetics (PK), and pharmacodynamics (PD) of the oral inhibitor of indoleamine 2,3-dioxygenase (IDO1) INCB024360 in patients (pts) with advanced malignancies." *ASCO Meeting Abstracts* 31(15_suppl): 3025.

Boasso, A., A. W. Hardy, S. A. Anderson, M. J. Dolan and G. M. Shearer (2008). "HIV-induced type I interferon and tryptophan catabolism drive T cell dysfunction despite phenotypic activation." *PLoS One* 3(8): e2961.

Boasso, A., J. P. Herbeuval, A. W. Hardy, S. A. Anderson, M. J. Dolan, D. Fuchs and G. M. Shearer (2007). "HIV inhibits CD4+ T-cell proliferation by inducing indoleamine 2,3-dioxygenase in plasmacytoid dendritic cells." *Blood* 109(8): 3351-3359.

Boasso, A. and G. M. Shearer (2008). "Chronic innate immune activation as a cause of HIV-1 immunopathogenesis." *Clin Immunol* 126(3): 235-242.

Boasso, A., M. Vaccari, A. Hryniewicz, D. Fuchs, J. Nacsa, V. Cecchinato, J. Andersson, G. Franchini, G. M. Shearer and C. Chougnet (2007). "Regulatory T-cell markers, indoleamine 2,3-dioxygenase, and virus levels in spleen and gut during progressive simian immunodeficiency virus infection." *J Virol* 81(21): 11593-11603.

Byakwaga, H., Y. Boum, 2nd, Y. Huang, C. Muzoora, A. Kembabazi, S. D. Weiser, J.

Bennett, H. Cao, J. E. Haberer, S. G. Deeks, D. R. Bangsberg, J. M. McCune, J. N. Martin and P. W. Hunt (2014). "The kynurenine pathway of tryptophan catabolism, CD4+ T-cell recovery, and mortality among HIV-infected Ugandans initiating antiretroviral therapy." *J Infect Dis* 210(3): 383-391.

Chen, Y. B., S. D. Li, Y. P. He, X. J. Shi, Y. Chen and J. P. Gong (2009). "Immunosuppressive effect of IDO on T cells in patients with chronic hepatitis B*." *Hepatol Res* 39(5): 463-468.

Darcy, C. J., J. S. Davis, T. Woodberry, Y. R. McNeil, D. P. Stephens, T. W. Yeo and N. M. Anstey (2011). "An observational cohort study of the kynurenine to tryptophan ratio in sepsis:association with impaired immune and microvascular function." *PLoS One* 6(6): e21185.

Deeks, S. G. (2011). "HIV infection, inflammation, immunosenescence, and aging." *Annu Rev Med* 62: 141-155.

Favre, D., S. Lederer, B. Kanwar, Z. M. Ma, S. Proll, Z. Kasakow, J. Mold, L. Swainson, J. D. Barbour, C. R. Baskin, R. Palermo, I. Pandrea, C. J. Miller, M. G. Katze and J. M. McCune (2009). "Critical loss of the balance between Th17 and T regulatory cell populations in pathogenic SIV infection." *PLoS Pathog* 5(2): e1000295.

Favre, D., J. Mold, P. W. Hunt, B. Kanwar, P. Loke, L. Seu, J. D. Barbour, M. M. Lowe, A. Jayawardene, F. Aweeka, Y. Huang, D. C. Douek, J. M. Brenchley, J. N. Martin, F. M. Hecht, S. G. Deeks and J. M. McCune (2010). "Tryptophan catabolism by indoleamine 2,3-dioxygenase 1 alters the balance of TH17 to regulatory T cells in HIV disease." *Sci Transl Med* 2(32): 32ra36.

Frumento, G., R. Rotondo, M. Tonetti, G. Damonte, U. Benatti and G. B. Ferrara (2002). "Tryptophan-derived catabolites are responsible for inhibition of T and natural killer cell proliferation induced by indoleamine 2,3-dioxygenase." *J Exp Med* 196(4): 459-468.

Gangadhar, T., O. Hamid, D. Smith, T. Bauer, J. Wasser, J. Luke, A. Balmanoukian, D. Kaufman, Y. Zhao, J. Maleski, L. Leopold and T. Gajewski (2015). "Preliminary results from a Phase I/II study of epacadostat (incb024360) in combination with pembrolizumab in patients with selected advanced cancers." *Journal for ImmunoTherapy of Cancer* 3(Suppl 2): O7.

Holmgaard, R. B., D. Zamarin, Y. Li, B. Gasmi, D. H. Munn, J. P. Allison, T. Merghoub and J. D. Wolchok (2015). "Tumor-Expressed IDO Recruits and Activates MDSCs in a Treg-Dependent Manner." *Cell Reports* 13(2): 412-424.

Holmgaard, R. B., D. Zamarin, D. H. Munn, J. D. Wolchok and J. P. Allison (2013). "Indoleamine 2,3-dioxygenase is a critical resistance mechanism in antitumor T cell immunotherapy targeting CTLA-4." *Journal of Experimental Medicine* 210(7): 1389-1402.

Hoshi, M., Y. Osawa, H. Ito, H. Ohtaki, T. Ando, M. Takamatsu, A. Hara, K. Saito and M. Seishima (2014). "Blockade of indoleamine 2,3-dioxygenase reduces mortality from peritonitis and sepsis in mice by regulating functions of CD11b+ peritoneal cells." *Infect Immun* 82(11): 4487-4495.

Hotchkiss, R. S., G. Monneret and D. Payen (2013). "Sepsis-induced immunosuppression: from cellular dysfunctions to immunotherapy." *Nat Rev Immunol* 13(12): 862-874.

Hunt, P. W., E. Sinclair, B. Rodriguez, C. Shive, B. Clagett, N. Funderburg, J. Robinson, Y. Huang, L. Epling, J. N. Martin, S. G. Deeks, C. L. Meinert, M. L. Van Natta, D. A. Jabs and M. M. Lederman (2014). "Gut epithelial barrier dysfunction and innate immune activation predict mortality in treated HIV infection." *J Infect Dis* 210(8): 1228-1238.

Ito, H., T. Ando, K. Ando, T. Ishikawa, K. Saito, H. Moriwaki and M. Seishima (2014). "Induction of hepatitis B virus surface antigen-specific cytotoxic T lymphocytes can be up-regulated by the inhibition of indoleamine 2,3-dioxygenase activity." *Immunology* 142(4): 614-623.

Jung, I. D., M. G. Lee, J. H. Chang, J. S. Lee, Y. I. Jeong, C. M. Lee, W. S. Park, J. Han, S. K. Seo, S. Y. Lee and Y. M. Park (2009). "Blockade of indoleamine 2,3-dioxygenase protects mice against lipopolysaccharide-induced endotoxin shock." *J Immunol* 182(5): 3146-3154.

Larrea, E., J. I. Riezu-Boj, L. Gil-Guerrero, N. Casares, R. Aldabe, P. Sarobe, M. P. Civeira, J. L. Heeney, C. Rollier, B. Verstrepen, T. Wakita, F. Borras-Cuesta, J. J. Lasarte and J. Prieto (2007). "Upregulation of indoleamine 2,3-dioxygenase in hepatitis C virus infection." *J Virol* 81(7): 3662-3666.

Lepiller, Q., E. Soulier, Q. Li, M. Lambotin, J. Barths, D. Fuchs, F. Stoll-Keller, T. J. Liang and H. Barth (2015). "Antiviral and Immunoregulatory Effects of Indoleamine-2,3-Dioxygenase in Hepatitis C Virus Infection." *J Innate Immun* 7(5): 530-544. Li, L., L. Huang, H. P. Lemos, M. Mautino and A. L. Mellor (2012). "Altered tryptophan metabolism as a paradigm for good and bad aspects of immune privilege in chronic inflammatory diseases." *Front Immunol* 3: 109.

Liu, X., N. Shin, H. K. Koblish, G. Yang, Q. Wang, K. Wang, L. Leffet, M. J. Hansbury, B. Thomas, M. Rupar, P. Waeltz, K. J. Bowman, P. Polam, R. B. Sparks, E. W. Yue, Y. Li, R. Wynn, J. S. Fridman, T. C. Burn, A. P. Combs, R. C. Newton and P. A. Scherle (2010). "Selective inhibition of IDO1 effectively regulates mediators of antitumor immunity." *Blood* 115(17): 3520-3530.

Loughman, J. A. and D. A. Hunstad (2012). "Induction of indoleamine 2,3-dioxygenase by uropathogenic bacteria attenuates innate responses to epithelial infection." *J Infect Dis* 205(12): 1830-1839.

Lovelace, M. D., B. Varney, G. Sundaram, M. J. Lennon, C. K. Lim, K. Jacobs, G. J. Guillemin and B. J. Brew (2016). "Recent evidence for an expanded role of the kynurenine pathway of tryptophan metabolism in neurological diseases." *Neuropharmacology*.

M. Mautino, C. J. L., N. Vahanian, J. Adams, C. Van Allen, M. D. Sharma, T. S. Johnson and D. H. Munn (2014). "Synergistic antitumor effects of combinatorial immune checkpoint inhibition with anti-PD-1/PD-L antibodies and the IDO pathway inhibitors NLG919 and indoximod in the context of active immunotherapy." April 2014 *AACR Meeting Poster* #5023.

Mattapallil, J. J., D. C. Douek, B. Hill, Y. Nishimura, M. Martin and M. Roederer (2005). "Massive infection and loss of memory CD4+ T cells in multiple tissues during acute SIV infection." *Nature* 434(7037): 1093-1097.

Mellor, A. L. and D. H. Munn (2004). "IDO expression by dendritic cells: Tolerance and tryptophan catabolism." *Nature Reviews Immunology* 4(10): 762-774.

Munn, D. H. (2011). "Indoleamine 2,3-dioxygenase, Tregs and cancer." *Current Medicinal Chemistry* 18(15): 2240-2246.

Munn, D. H., E. Shafizadeh, J. T. Attwood, I. Bondarev, A. Pashine and A. L. Mellor (1999). "Inhibition of T cell proliferation by macrophage tryptophan catabolism." *J Exp Med* 189(9): 1363-1372.

Pilotte, L., P. Larrieu, V. Stroobant, D. Colau, E. Dolušić, R. Frédérick, E. De Plaen, C. Uyttenhove, J. Wouters, B. Masereel and B. J. Van Den Eynde (2012). "Reversal of tumoral immune resistance by inhibition of tryptophan 2,3-dioxygenase." *Proceedings of the National Academy of Sciences of the United States of America* 109(7): 2497-2502.

Sekkai, D., O. Guittet, G. Lemaire, J. P. Tenu and M. Lepoivre (1997). "Inhibition of nitric oxide synthase expression and activity in macrophages by 3-hydroxyanthranilic acid, a tryptophan metabolite." *Arch Biochem Biophys* 340(1): 117-123.

Suzuki, Y., T. Suda, K. Asada, S. Miwa, M. Suzuki, M. Fujie, K. Furuhashi, Y. Nakamura, N. Inui, T. Shirai, H. Hayakawa, H. Nakamura and K. Chida (2012). "Serum indoleamine 2,3-dioxygenase activity predicts prognosis of pulmonary tuberculosis." *Clin Vaccine Immunol* 19(3): 436-442.

Tattevin, P., D. Monnier, O. Tribut, J. Dulong, N. Bescher, F. Mourcin, F. Uhel, Y. Le Tulzo and K. Tarte (2010). "Enhanced indoleamine 2,3-dioxygenase activity in patients with severe sepsis and septic shock." *J Infect Dis* 201(6): 956-966.

Tenorio, A. R., Y. Zheng, R. J. Bosch, S. Krishnan, B. Rodriguez, P. W. Hunt, J. Plants, A. Seth, C. C. Wilson, S. G. Deeks, M. M. Lederman and A. L. Landay (2014). "Soluble markers of inflammation and coagulation but not T-cell activation predict non-AIDS-defining morbid events during suppressive antiretroviral treatment." *J Infect Dis* 210(8): 1248-1259.

Wainwright, D. A., I. V. Balyasnikova, A. L. Chang, A. U. Ahmed, K.-S. Moon, B. Auffinger, A. L. Tobias, Y. Han and M. S. Lesniak (2012). "IDO Expression in Brain Tumors Increases the Recruitment of Regulatory T Cells and Negatively Impacts Survival." *Clinical Cancer Research* 18(22): 6110-6121.

Wainwright, D. A., A. L. Chang, M. Dey, I. V. Balyasnikova, C. K. Kim, A. Tobias, Y. Cheng, J. W. Kim, J. Qiao, L. Zhang, Y. Han and M. S. Lesniak (2014). "Durable therapeutic efficacy utilizing combinatorial blockade against IDO, CTLA-4, and PD-L1 in mice with brain tumors." *Clinical Cancer Research* 20(20): 5290-5301.

Yue, E. W., B. Douty, B. Wayland, M. Bower, X. Liu, L. Leffet, Q. Wang, K. J. Bowman, M. J. Hansbury, C. Liu, M. Wei, Y. Li, R. Wynn, T. C. Burn, H. K. Koblish, J. S. Fridman, B. Metcalf, P. A. Scherle and A. P. Combs (2009). "Discovery of potent competitive inhibitors of indoleamine 2,3-dioxygenase with in vivo pharmacodynamic activity and efficacy in a mouse melanoma model." *Journal of Medicinal Chemistry* 52(23): 7364-7367.

SUMMARY OF THE INVENTION

Briefly, in one aspect, the present invention discloses compounds of Formula I

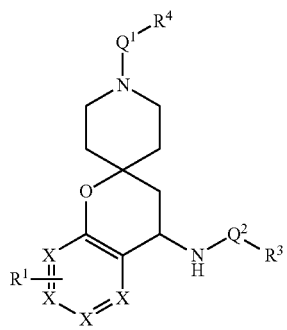

Formula I or a pharmaceutically acceptable salt thereof wherein: or a pharmaceutically acceptable salt thereof wherein:

each X is CH or one X is N and the other 3 are CH;

$Q^1$ is a bond (i.e. is absent), —C(O)C—, or —C(O)—;

$Q^2$ is a bond (i.e. is absent) or —C(O)—;

$R^1$ is absent, halogen, $C_{1-3}$alkylOH, or C(O)O$C_{1-3}$alkyl;

$R^3$ is $C_{5-9}$aryl, or 5-9 membered heteroaryl, wherein aryl and heteroaryl include bicycles and heteroaryl contains 1-3 hetero atoms selected from O, S, and N, and wherein $R^3$ may optionally be substituted with a substituent selected from halogen, OH, $C_{1-3}$alkyl, $OC_{1-3}$ alkyl, $C_{1-3}$fluoroalkyl, CN, and $NH_2$; and $R^4$ is H, $C_{1-3}$haloalkyl, phenyl or $C_{1-6}$alkyl In another aspect, the present invention discloses a method for treating diseases or conditions that would benefit from inhibition of IDO.

In another aspect, the present invention discloses pharmaceutical compositions comprising a compound of Formula I or a pharmaceutically acceptable salt thereof.

In another aspect, the present invention provides a compound of Formula I or a pharmaceutically acceptable salt thereof for use in therapy.

In another aspect, the present invention provides a compound of Formula I or a pharmaceutically acceptable salt thereof for use in treating diseases or condition that would benefit from inhibition of IDO.

In another aspect, the present invention provides use of a compound of Formula I or a pharmaceutically acceptable salt thereof in the manufacture of a medicament for use in treating diseases or conditions that would benefit from inhibition of IDO.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

DETAILED DESCRIPTION OF REPRESENTATIVE EMBODIMENTS

Preferably each X is CH.

Preferably $Q^1$ is C(O)O.

Preferably $Q^2$ is C(O).

Preferably $R^1$ is Br, $OCH_3$, or is absent.

Preferably $R^3$ is indole, benzodiazole, phenyl, pyridyl, diazole, or pyrimidine, and wherein $R^3$ may optionally be substituted with a substituent selected from halogen, OH, $C_{1-3}$alkyl, $OC_{1-3}$alkyl, $C_{1-3}$ fluoroalkyl, CN, and $NH_2$. More preferably $R^3$ is indole or benzodiazole, and may optionally be substituted with a substituent selected from halogen, OH, $C_{1-3}$alkyl, $OC_{1-3}$alkyl, $C_{1-3}$fluoroalkyl, CN, and $NH_2$. Most preferably $R^3$ is unsubstituted indazole.

Preferably $R^4$ is H, $C_{1-4}$alkyl, $CF_3$, or phenyl. More preferably $R^4$ is $C_{1-4}$alkyl.

Preferably the stereochemistry of the carbon atom to which NH-$Q^2$-$R^3$ is bonded is as depicted below.

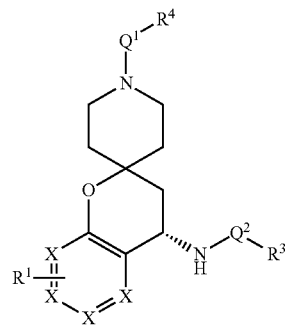

Preferred pharmaceutical compositions include unit dosage forms. Preferred unit dosage forms include tablets.

In particular, it is expected that the compounds and composition of this invention will be useful for prevention and/or treatment of HIV; including the prevention of the progression of AIDS and general immunosuppression. It is expected that in many cases such prevention and/or treatment will involve treating with the compounds of this invention in combination with at least one other drug thought to be useful for such prevention and/or treatment. For example, the IDO inhibitors of this invention may be used in combination with other immune therapies such as immune checkpoints (PD1, CTLA4, ICOS, etc.) and possibly in combination with growth factors or cytokine therapies (IL21, IL-7, etc.).

In is common practice in treatment of HIV to employ more than one effective agent. Therefore, in accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors. Examples of such additional agents are Dolutegravir, Bictegravir, and Cabotegravir.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment, the pharmaceutical formulation containing a compound of Formula I or a salt thereof is a formulation adapted for oral or parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of l-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

EXAMPLES

Compounds of the invention can be prepared by one skilled in the art according to the following general synthetic scheme.

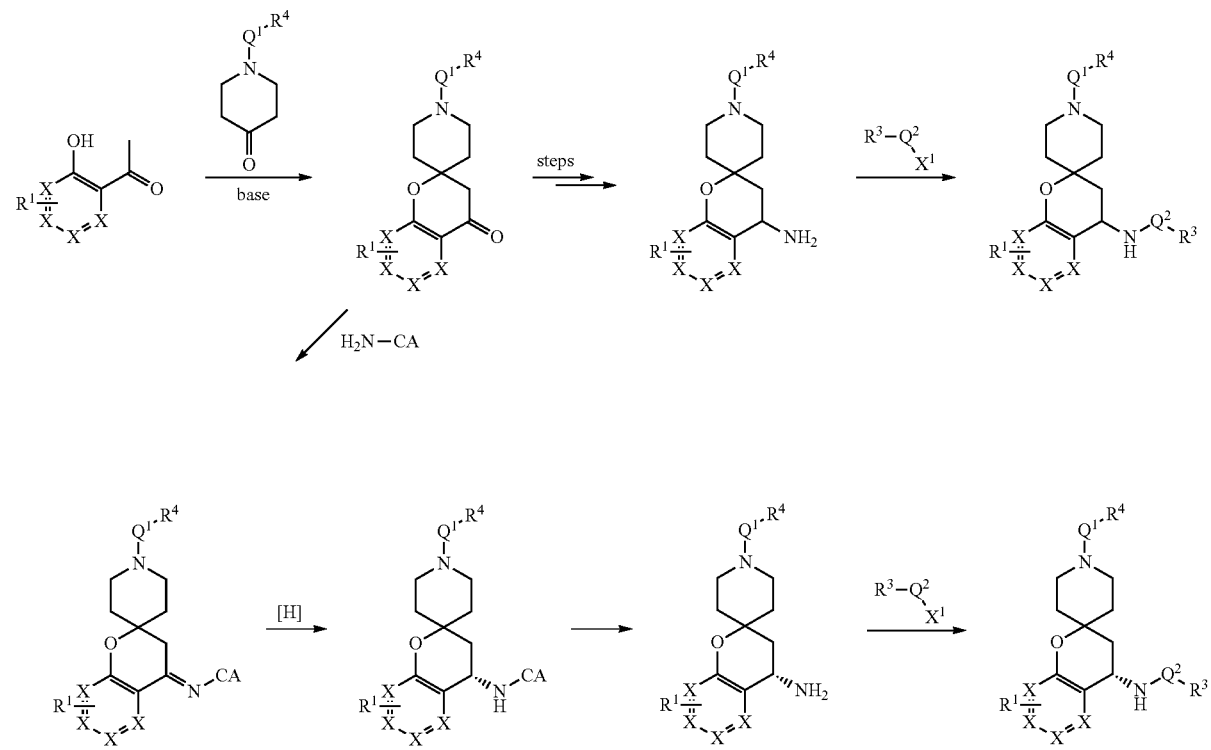

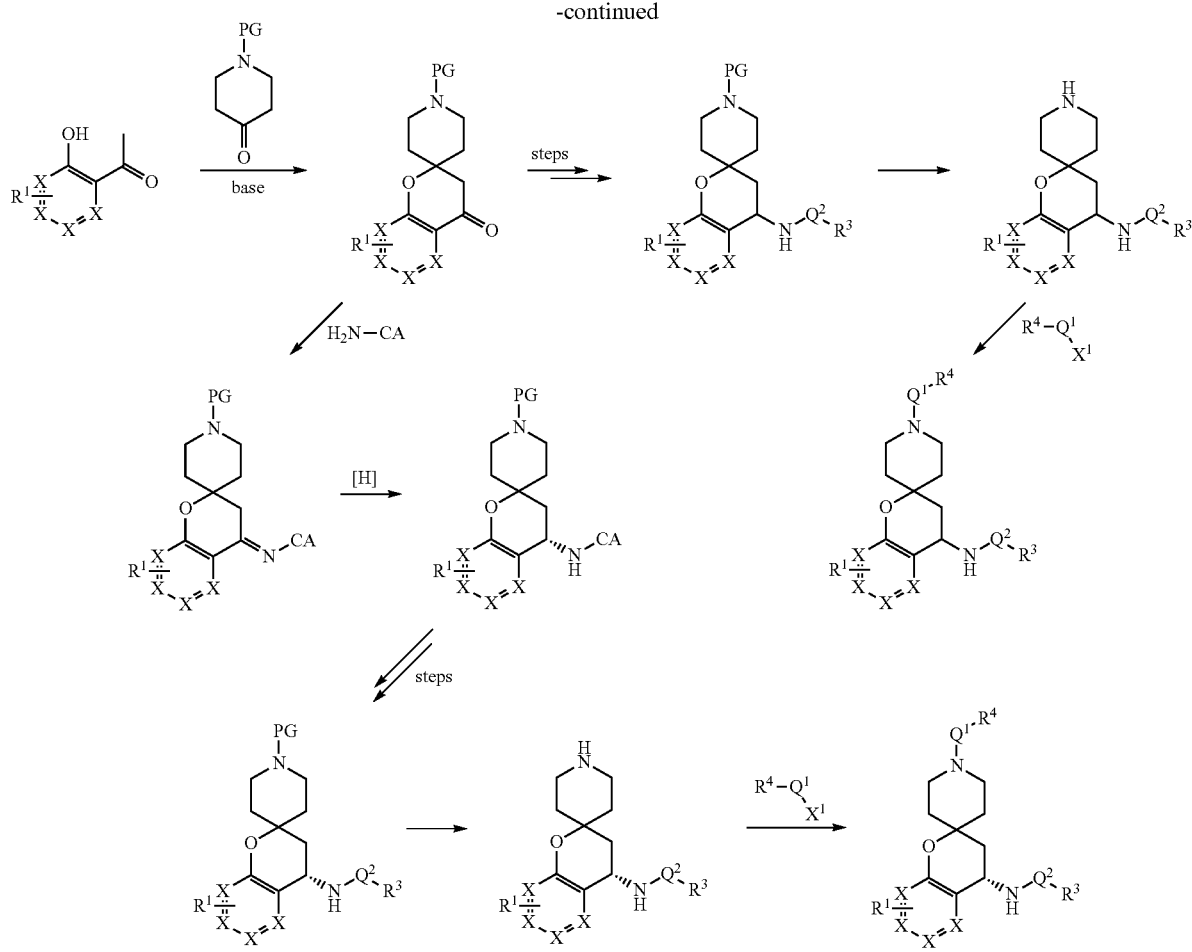

PG = protecting group
CA = chiral auxillary
X¹ = halogen or other leaving group

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

| abbreviation | meaning |
| --- | --- |
| ° C. | degrees Celsius |
| DCM | dichloromethane |
| DEA | diethylamine |
| DIEA | N,N-diisopropylethylamine |
| DMF | N,N-dimethylformamide |
| DMSO | dimethylsulfoxide |
| ESI | electrospray ionization |
| h or hr | hours |
| HATU | (1-[bis(dimethylamino)methylene]-1H-1,2,3-triazolo[4,5-b]pyridinium 3-oxid hexafluorophosphate) |
| HPLC | high performance liquid chromatography |
| J | coupling constant in Hz |
| LCMS | liquid chromatography - mass spectrometry |
| M | molar |
| Mg | milligram |
| min | minute |
| mL | milliliters |
| mM | millimolar |
| mmol | millimole |
| µL or uL | microliters |
| µM or uM | micromolar |
| MS | mass spectrum |
| N | normal |
| NBS | N-bromosuccinimide |
| NMR | nuclear magnetic resonance |
| PE | petroleum ether |
| ppm | parts per million |
| RT | room temperature |
| Rf | retention factor |
| TEA | triethylamine |
| TFA | trifluoroacetic acid |
| THF | tetrahydrofuran |
| TLC | thin layer chromatography |

Equipment Description $^1$H NMR spectra were recorded on a Varian 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters ACQUITY UPLC with SQ Detectors using a Waters BEH C18, 2.1×50 mm, 1.7 μm using a gradient elution method. Solvent A: 0.1% formic acid (FA) in water. Solvent B: 0.1% FA in acetonitrile; 30% B for 0.5 min followed by 30-100% B over 2.5 min.

Example 1: (S)-ethyl 6-bromo-4-(1H-indole-7-carboxamido)spiro[chroman-2,4'-piperidine]-1'-carboxylate

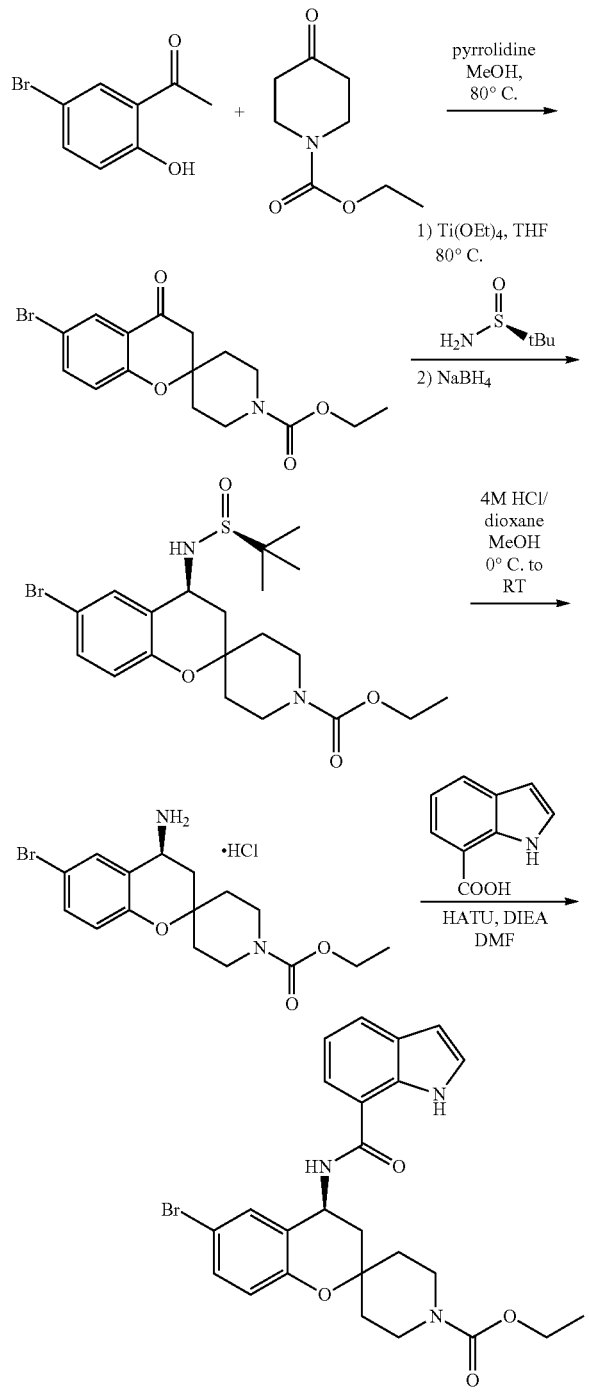

Step 1: Preparation of ethyl 6-bromo-4-oxospiro[chroman-2,4'-piperidine]-1'-carboxylate

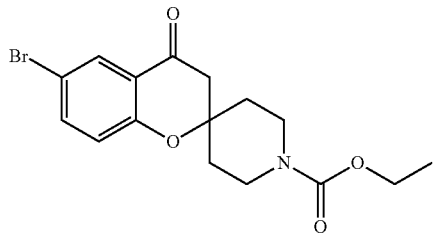

To a stirred solution of 1-(5-bromo-2-hydroxyphenyl)ethan-1-one (2.00 g, 9.30 mmol) in MeOH (15 mL) in a screw capped pressure vessel was added pyrrolidine (0.385 mL, 4.65 mmol). The resulting yellow-orange solution was stirred at RT for 30 minutes, and then treated with a solution of ethyl 4-oxopiperidine-1-carboxylate (1.59 g, 9.30 mmol) in MeOH (3 mL). The reaction vessel was sealed and heated to 80° C. After 4 hours LCMS indicated complete reaction. The vessel was cooled to RT during which time a solid crystallized. The suspension was cooled in an ice water bath for 30 minutes, and the solid collected by vacuum filtration, washing with two portions of ice cold MeOH. Drying in vacuo afforded the title compound as a light tan solid (3.02 g, 88%). LCMS (ESI) m/z calcd for $C_{16}H_{18}BrNO_4$: 367.04. Found: 368.12 (M+1)+. $^1$H NMR (400 MHz, DMSO-d$_6$) δ 7.68-7.81 (m, 2H), 7.07 (d, J=9.0 Hz, 1H), 4.01 (q, J=7.0 Hz, 2H), 3.67-3.81 (m, 2H), 3.15 (br s, 2H), 2.86 (s, 2H), 1.87 (m, 2H), 1.54-1.70 (m, 2H), 1.15 (t, J=7.0 Hz, 3H).

Step 2: Preparation of (S)-ethyl 6-bromo-4-((S)-1,1-dimethylethylsulfinamido)spiro[chroman-2,4'-piperidine]-1'-carboxylate

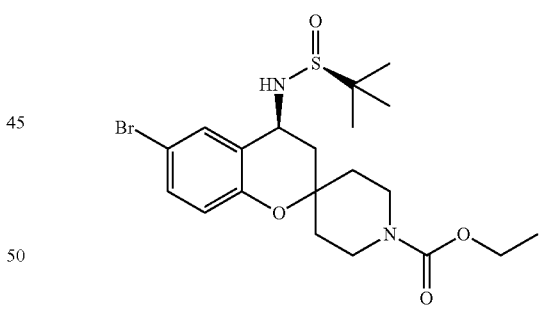

To a stirred solution of ethyl 6-bromo-4-oxospiro[chromane-2,4'-piperidine]-1'-carboxylate (1.00 g, 2.72 mmol) and (S)-2-methylpropane-2-sulfinamide (0.658 g, 5.43 mmol) in anhydrous THF (12 mL) in a screw capped glass pressure vessel under a nitrogen atmosphere was added Ti(OEt)$_4$ (1.71 mL, 8.15 mmol). The vessel was sealed and the solution heated in an 80° C. oil bath. Conversion of the starting material to the imine intermediate was monitored by LCMS. After 24 hours the conversion was nearly complete. The solution was cooled to RT and then to 0° C. in an ice water bath. The solution was treated with NaBH$_4$ (0.514 g, 13.6 mmol). After stirring at 0° C. for 30 minutes the mixture was allowed to warm to RT. After 18 hours LCMS indicated complete conversion of the imine intermediate to the desired amine product as a 92:8 mixture of diastereomers. The cloudy solution was cooled to 0° C. and quenched by slow addition of MeOH until gas evolution ceased. The resulting mixture was treated with saturated aqueous brine (6 mL) to afford a thick, light yellow suspension. The solid was removed by filtration through a medium fritted funnel. The filter cake was washed with EtOAc (3×). The filtrate was washed with saturated brine (1×), dried over $Na_2SO_4$, and concentrated at reduced pressure. The residue was subjected to flash chromatography (silica gel, 20-100% EtOAc/DCM, gradient elution) to afford the title compound as a white solid (0.732 g, 57% yield). LCMS (ESI) m/z calcd for $C_{20}H_{29}BrN_2O_4S$: 472.10. Found: 473.19 (M+1)$^+$. $^1$H NMR (400 MHz, CDCl$_3$) δ 7.73 (d, J=2.0 Hz, 1H), 7.23-7.31 (m, 1H), 6.74 (d, J=8.6 Hz, 1H), 4.52-4.64 (m, 1H), 4.13 (q, J=7.0 Hz, 2H), 3.93 (br s, 2H), 3.42-3.53 (m, 2H), 2.97-3.35 (m, 2H), 2.03-2.09 (m, 1H), 1.41-2.01 (m, 4H), 1.16-1.33 (m, 12H).

Step 3: Preparation of (S)-ethyl 4-amino-6-bromo-spiro[chroman-2,4'-piperidine]-1'-carboxylate hydrochloride

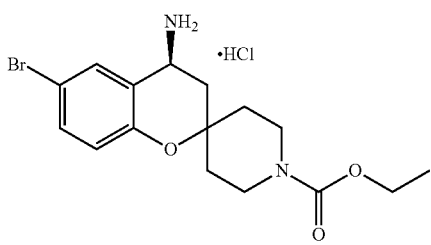 [SMILES: CCOC(=O)N1CCC2(CC1)C[C@H](N)c1cc(Br)ccc1O2 ; Cl]

To a stirred suspension of ethyl (S)-6-bromo-4-(((S)-tert-butylsulfinyl)amino)spiro[chromane-2,4'-piperidine]-1'-carboxylate (0.200 g, 0.422 mmol) in anhydrous MeOH (5 mL) at 0° C. was added 4N HCl/dioxane (0.106 mL, 0.422 mmol) by dropwise addition. The solution was then allowed to warm to RT. After 3 hours the solution was treated with an additional portion of 4N HCl/dioxane (0.10 mL) and stirring at RT continued. After another 2 hours LCMS indicated complete reaction. The solution was concentrated to dryness at reduced pressure. The residue was redissolved in MeOH and again concentrated to dryness to afford the title compound as a tan solid in quantitative yield. This material was used without further purification. $^1$H NMR (400 MHz, methanol-d$_4$) δ 7.62 (d, J=1.6 Hz, 1H), 7.43 (dd, J=8.8, 2.2 Hz, 1H), 6.91 (d, J=9.0 Hz, 1H), 4.66 (dd, J=11.5, 6.8 Hz, 1H), 4.11 (q, J=7.3 Hz, 2H), 3.94-4.03 (m, 1H), 3.83-3.92 (m, 1H), 3.29-3.49 (m, 1H), 2.99-3.15 (m, 1H), 2.32 (dd, J=13.3, 6.6 Hz, 1H), 1.73-1.96 (m, 4H), 1.52-1.63 (m, 1H), 1.24 (t, J=7.0 Hz, 3H).

Step 4: Preparation of (S)-ethyl 6-bromo-4-(1H-indole-7-carboxamido)spiro[chroman-2,4'-piperidine]-1'-carboxylate

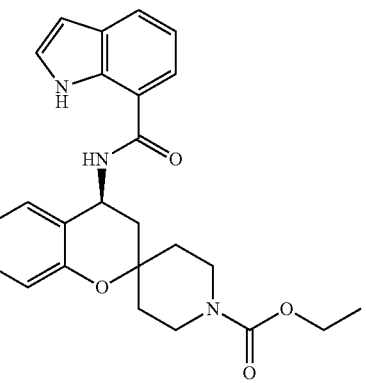

To a stirred solution of (S)-ethyl 4-amino-6-bromospiro[chroman-2,4'-piperidine]-1'-carboxylate hydrochloride (85.0 mg, 0.210 mmol) and 1H-indole-7-carboxylic acid (37.1 mg, 0.230 mmol) in DMF (3 mL) was added DIEA (0.110 mL, 0.629 mmol) followed by HATU (0.119 g, 0.314 mmol). The resulting solution was stirred at RT. After 18 hours the solution was treated with 2M ammonia/MeOH (2 mL), stirred for an additional 20 minutes, and then partitioned between EtOAc and 10% aqueous citric acid. After separating the phases, the EtOAc phase was washed with 10% aqueous citric acid (1×), saturated aqueous NaHCO$_3$ (2×), dried over Na$_2$SO$_4$ and concentrated to dryness at reduced pressure. The residue was subjected to flash chromatography (silica gel, 20-100% EtOAc/hexanes, gradient elution) to afford the title compound as a white solid (65 mg, 61% yield). Chiral analytical HPLC indicated an enantiomeric purity of 98% [Chiralpak AD column (4.6 mm×250 mm, 5μ); mobile phase: 1:1 EtOH/hexane; flow rate 1 mL/min; injection volume: 8 uL (1 mg/mL conc.); monitored at 254 nm]. LCMS (ESI) m/z calcd for $C_{25}H_{26}BrN_3O_4$: 511.11. Found: 512.16 (M+1)$^+$. $^1$H NMR (400 MHz, CDCl$_3$) δ 10.30 (brs, 1H), 7.85 (d, J=7.8 Hz, 1H), 7.44 (d, J=1.6 Hz, 1H), 7.34-7.39 (m, 2H), 7.31 (dd, J=8.8, 2.2 Hz, 1H), 7.13 (t, J=7.6 Hz, 1H), 6.79 (d, J=8.6 Hz, 1H), 6.61 (t, J=2.7 Hz, 1H), 6.47 (d, J=8.6 Hz, 1H), 5.51-5.62 (m, 1H), 4.14 (q, J=7.0 Hz, 2H), 3.96 (brs, 2H), 3.30-3.42 (m, 1H), 3.06-3.19 (m, 1H), 2.30 (dd, J=13.5, 6.4 Hz, 1H), 1.55-1.99 (m, 5H), 1.58-1.26 (t, J=7.2 Hz, 3H).

Example 2: (S)-ethyl 6-bromo-4-(1H-indazole-7-carboxamido)spiro[chroman-2,4'-piperidine]-1'-carboxylate

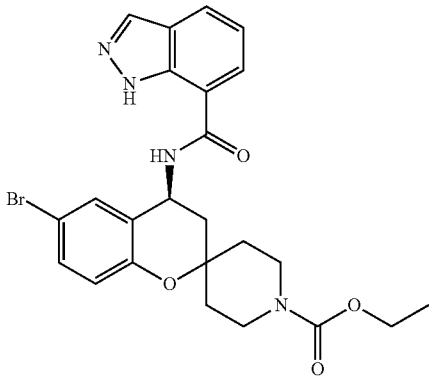 [SMILES: CCOC(=O)N1CCC2(CC1)C[C@H](NC(=O)c1cccc3cn[nH]c13)c1cc(Br)ccc1O2]

The title compound was prepared in 58% yield from (S)-ethyl 4-amino-6-bromospiro[chroman-2,4'-piperidine]-1'-carboxylate hydrochloride and 1H-indazole-7-carboxylic acid according to the method described herein for the synthesis of (S)-ethyl 6-bromo-4-(1H-indole-7-carboxamido)spiro[chroman-2,4'-piperidine]-1'-carboxylate. Chiral analytical HPLC indicated an enantiomeric purity of 99% [Regis (S,S) Whelk-O1 column (4.6 mm×250 mm, 5p); mobile phase: 1:1 EtOH/hexane; flow rate 1 mL/min; injection volume: 5 uL (1 mg/mL conc.); monitored at 254 nm]. LCMS (ESI) m/z calcd for $C_{24}H_{25}BrN_4O_4$: 512.11. Found: 513.19 (M+1)$^+$. $^1$H NMR (400 MHz, CDCl$_3$) δ 11.75 (brs, 1H), 8.15 (s, 1H), 7.98 (d, J=7.8 Hz, 1H), 7.59 (d, J=7.4 Hz, 1H), 7.43 (d, J=1.6 Hz, 1H), 7.17-7.36 (m, 2H), 6.80 (d, J=8.6 Hz, 1H), 6.57 (brs, 1H), 5.52-5.70 (m, 1H), 3.75-4.20 (m, 4H), 3.28-3.44 (m, 1H), 3.02-3.20 (m, 1H), 2.34 (dd, J=13.5, 6.4 Hz, 1H), 1.47-2.01 (m, 5H), 1.19-1.31 (m, 3H).

Example 3: (R)-ethyl 6-bromo-4-(1H-indazole-7-carboxamido)spiro[chroman-2,4'-piperidine]-1'-carboxylate

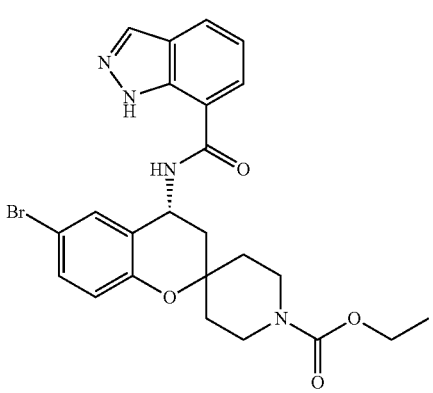 [SMILES: CCOC(=O)N1CCC2(CC1)C[C@@H](NC(=O)c1cccc3cn[nH]c13)c1cc(Br)ccc1O2]

The title compound was prepared in 3 steps starting with ethyl 6-bromo-4-oxospiro[chroman-2,4'-piperidine]-1'-carboxylate and (R)-2-methylpropane-2-sulfinamide according to the sequence described herein for the synthesis of (S)-ethyl 6-bromo-4-(1H-indazole-7-carboxamido)spiro[chroman-2,4'-piperidine]-1'-carboxylate. Chiral analytical HPLC indicated an enantiomeric purity of 99% [Regis (S,S) Whelk-O1 column (4.6 mm×250 mm, 5p); mobile phase: 1:1 EtOH/hexane; flow rate 1 mL/min; injection volume: 5 uL (1 mg/mL conc.); monitored at 254 nm]. LCMS (ESI) m/z calcd for $C_{24}H_{25}BrN_4O_4$: 512.11. Found: 513.24 (M+1)$^+$. $^1$H NMR (400 MHz, CDCl$_3$) δ 11.75 (br s, 1H), 8.15 (s, 1H), 7.98 (d, J=7.8 Hz, 1H), 7.59 (d, J=7.4 Hz, 1H), 7.43 (d, J=1.6 Hz, 1H), 7.17-7.36 (m, 2H), 6.80 (d, J=8.6 Hz, 1H), 6.57 (br s, 1H), 5.52-5.70 (m, 1H), 3.75-4.20 (m, 4H), 3.28-3.44 (m, 1H), 3.02-3.20 (m, 1H), 2.34 (dd, J=13.5, 6.4 Hz, 1H), 1.47-2.01 (m, 5H), 1.19-1.31 (m, 3H).

Example 4: (S)-methyl 6-bromo-4-(1H-indole-7-carboxamido)spiro[chroman-2,4'-piperidine]-1'-carboxylate

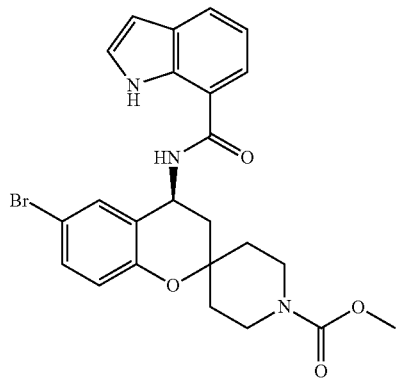 [SMILES: COC(=O)N1CCC2(CC1)C[C@H](NC(=O)c1cccc3cc[nH]c13)c1cc(Br)ccc1O2]

The title compound was prepared in 4 steps starting with 1-(5-bromo-2-hydroxyphenyl)ethanone and methyl 4-oxopiperidine-1-carboxylate according to the sequence described herein for the synthesis of (S)-ethyl 6-bromo-4-(1H-indole-7-carboxamido)spiro[chroman-2,4'-piperidine]-1'-carboxylate. LCMS (ESI) m/z calcd for $C_{24}H_{24}BrN_3O_4$: 497.10. Found: 498.20 (M+1)$^+$. $^1$H NMR (400 MHz, DMSO-d$_6$) δ 11.23 (br s, 1H), 8.91 (d, J=8.2 Hz, 1H), 7.74 (d, J=7.8 Hz, 1H), 7.69 (d, J=7.4 Hz, 1H), 7.26-7.37 (m, 3H), 7.05 (t, J=7.6 Hz, 1H), 6.83 (d, J=8.6 Hz, 1H), 6.49 (dd, J=2.9, 2.2 Hz, 1H), 5.36-5.47 (m, 1H), 3.68-3.86 (m, 2H), 3.58 (s, 3H), 3.24-3.37 (m, 1H), 3.06 (br s, 1H), 2.16 (dd, J=13.3, 6.6 Hz, 1H), 1.95-2.05 (m, 1H) 1.50-1.87 (m, 4H).

Example 5: (S)-methyl 6-bromo-4-(1H-indazole-7-carboxamido)spiro[chroman-2,4'-piperidine]-1'-carboxylate

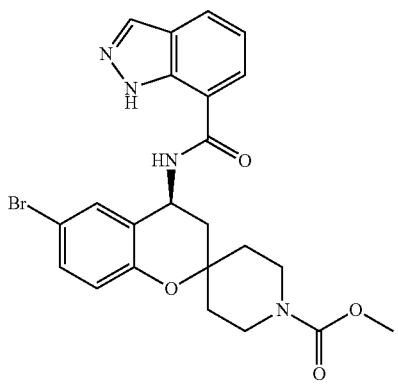 [SMILES: COC(=O)N1CCC2(CC1)C[C@H](NC(=O)c1cccc3cn[nH]c13)c1cc(Br)ccc1O2]

The title compound was prepared in 4 steps starting with 1-(5-bromo-2-hydroxyphenyl)ethanone and methyl 4-oxopiperidine-1-carboxylate according to the sequence described herein for the synthesis of (S)-ethyl 6-bromo-4-(1H-indazole-7-carboxamido)spiro[chroman-2,4'-piperidine]-1'-carboxylate. LCMS (ESI) m/z calcd for $C_{23}H_{23}BrN_4O_4$: 498.09. Found: 499.24 (M+1)$^+$. $^1$H NMR (400 MHz, DMSO-d$_6$) δ 13.18 (br s, 1H), 9.06 (d, J=7.0 Hz, 1H), 8.16 (s, 1H), 7.96 (dd, J=13.5, 7.6 Hz, 2H), 7.27-7.39 (m, 2H), 7.19 (t, J=7.6 Hz, 1H), 6.84 (d, J=8.6 Hz, 1H), 5.36-5.49 (m, 1H), 3.66-3.87 (m, 2H), 3.58 (s, 3H), 3.21-3.38 (m, 1H), 2.97-3.16 (m, 1H), 2.19 (dd, J=13.3, 6.3 Hz, 1H), 1.98 (t, J=12.5 Hz, 1H), 1.52-1.89 (m, 4H).

Example 6: (S)-isopropyl 6-bromo-4-(1H-indazole-7-carboxamido)spiro[chroman-2,4'-piperidine]-1'-carboxylate

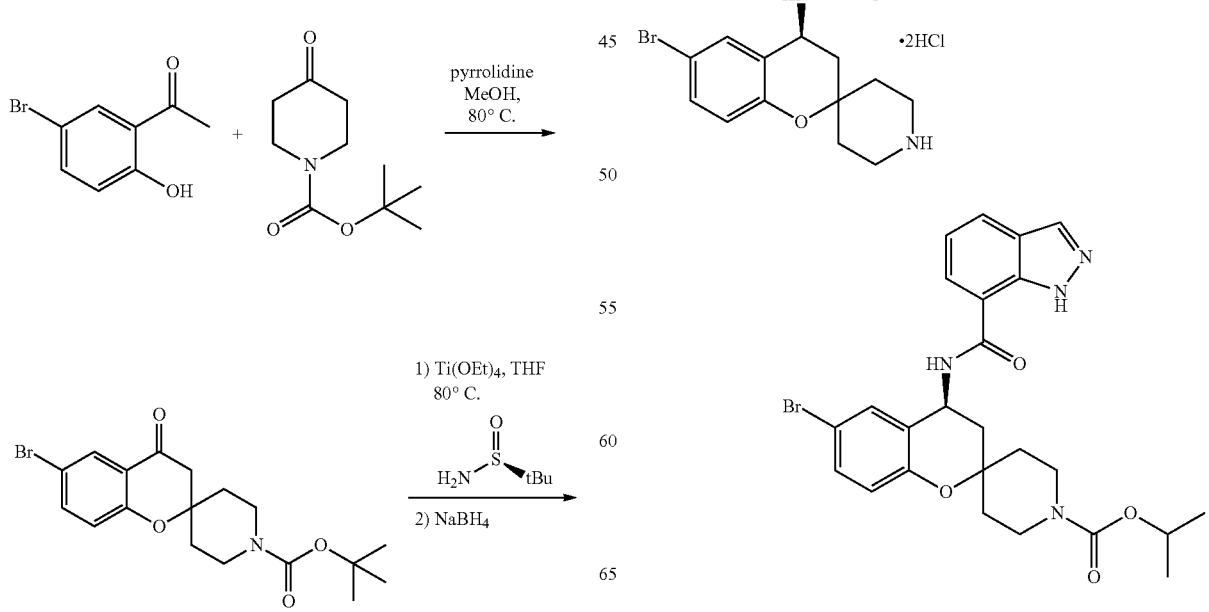

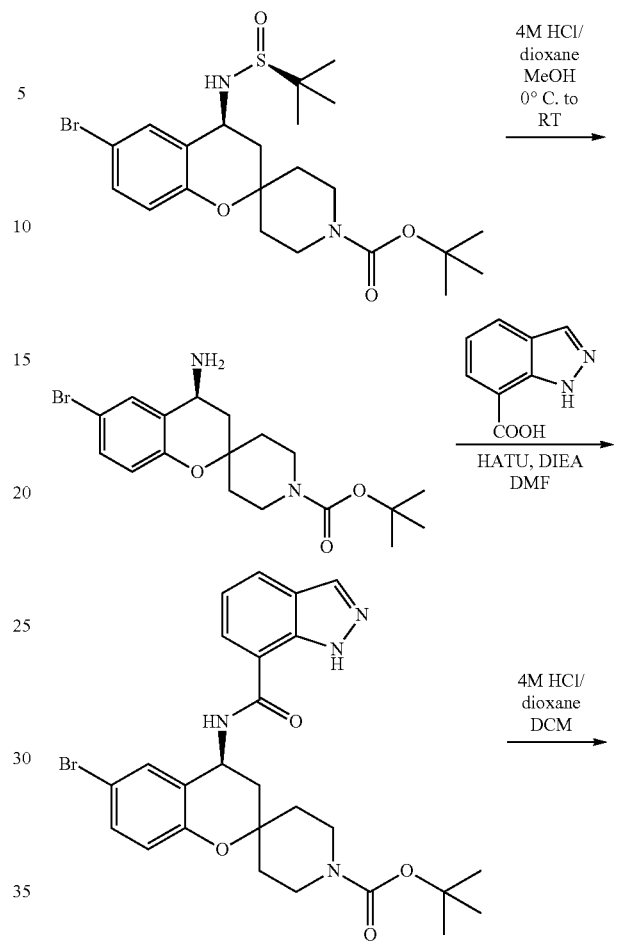

Step 1: Preparation of tert-butyl 6-bromo-4-oxospiro[chroman-2,4'-piperidine]-1'-carboxylate

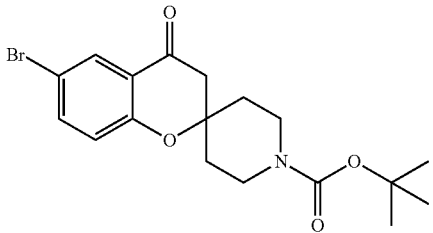 [SMILES: CC(C)(C)OC(=O)N1CCC2(CC1)CC(=O)c1cc(Br)ccc1O2]

To a stirred solution of 1-(5-bromo-2-hydroxyphenyl)ethan-1-one (10.0 g, 46.5 mmol) in MeOH (80 mL) in a screw capped pressure vessel was added pyrrolidine (1.92 mL, 23.3 mmol). The resulting yellow-orange solution was stirred at RT for 30 minutes, and then treated with tert-butyl 4-oxopiperidine-1-carboxylate (9.27 g, 46.5 mmol). The reaction vessel was sealed and heated to 80° C. After 18 hours LCMS indicated complete reaction. The solution was cooled to RT and concentrated to a syrup at reduced pressure. The residue was partitioned between EtOAc and 10% aqueous citric acid and the phases separated. The aqueous phase was extracted with EtOAc (1×). The combined EtOAc solutions were washed with 10% aqueous citric acid (1×), saturated aqueous NaHCO$_3$ (2×), dried over Na$_2$SO$_4$, and concentrated at reduced pressure. The residue was subjected to flash chromatography (silica gel, 0-60% EtOAc/hexanes, gradient elution) followed by crystallization from hexanes to afford the title compound as a white solid (16.1 g, 88% yield). $^1$H NMR (400 MHz, CDCl$_3$) δ 7.96 (d, J=2.3 Hz, 1H), 7.56 (dd, J=9.0, 2.3 Hz, 1H), 6.88 (d, J=9.0 Hz, 1H), 3.86 (br s, 2H), 3.11-3.23 (m, 2H), 2.70 (s, 2H), 1.94-2.04 (m, 2H), 1.54-1.67 (m, 2H), 1.44 (s, 9H).

Step 2: Preparation of (5)-tert-butyl 6-bromo-4-((S)-1,1-dimethylethylsulfinamido)spiro[chroman-2,4'-piperidine]-1'-carboxylate

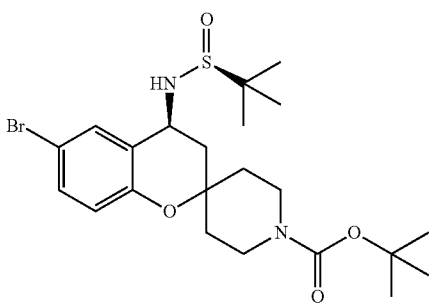 [SMILES: CC(C)(C)OC(=O)N1CCC2(CC1)C[C@H](N[S@@](=O)C(C)(C)C)c1cc(Br)ccc1O2]

The title compound was prepared in 90% yield from tert-butyl 6-bromo-4-oxospiro[chroman-2,4'-piperidine]-1'-carboxylate and (S)-2-methylpropane-2-sulfinamide according to the procedure described herein for the synthesis of (S)-ethyl 6-bromo-4-((S)-1,1-dimethylethylsulfinamido)spiro[chroman-2,4'-piperidine]-1'-carboxylate. LCMS (ESI) m/z calcd for C$_{22}$H$_{33}$BrN$_2$O$_4$S: 500.13. Found: 501.23 (M+1)$^+$. $^1$H NMR (400 MHz, CDCl$_3$) δ 7.74 (s, 1H), 7.24-7.33 (m, 1H), 6.75 (d, J=8.6 Hz, 1H), 4.52-4.65 (m, 1H), 3.87 (br s, 2H), 3.48 (d, J=6.3 Hz, 1H), 2.96-3.34 (m, 2H), 2.03-2.13 (m, 1H), 1.07-2.01 (m, 23H).

Step 3: Preparation of (5)-tert-butyl 4-amino-6-bromospiro[chroman-2,4'-piperidine]-1'-carboxylate

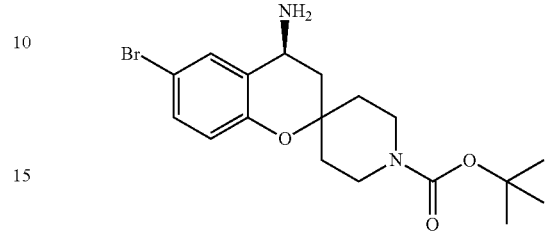

To a stirred solution of tert-butyl (S)-6-bromo-4-(((S)-tert-butylsulfinyl)amino)spiro[chromane-2,4'-piperidine]-1'-carboxylate (3.00 g, 5.98 mmol) in MeOH (30 ml) at 0° C. was added 4N HCl/dioxane (1.50 ml, 5.98 mmol) by dropwise addition. The solution was stirred at 0° C. for 30 minutes and then allowed to warm to RT. After 3 hours LCMS indicated complete reaction. The solution was treated with 2M ammonia/MeOH (8.97 mL, 18.0 mmol) and concentrated at reduced pressure. The residue was partitioned between DCM and 10% aqueous Na$_2$CO$_3$ and the phases separated. The aqueous phase was extracted with DCM (2×). The combined DCM solutions were dried over Na$_2$SO$_4$ and concentrated to dryness at reduced pressure. The residue was crystallized from hexanes to afford the title compound as a white solid (1.87 g, 79% yield). LCMS (ESI) m/z calcd for C$_{18}$H$_{25}$BrN$_2$O$_3$: 396.11. Found: 397.26 (M+1)$^+$. $^1$H NMR (400 MHz, CDCl$_3$) δ 7.57 (d, J=2.0 Hz, 1H), 7.22 (dd, J=8.6, 2.3 Hz, 1H), 6.70 (d, J=8.6 Hz, 1H), 3.67-4.06 (m, 3H), 3.23-3.38 (m, 1H), 2.98-3.12 (m, 1H), 2.05 (dd, J=13.3, 6.3 Hz, 1H), 1.34-1.86 (m, 16H).

Step 4: Preparation of (5)-tert-butyl 6-bromo-4-(1H-indazole-7-carboxamido)spiro[chroman-2,4'-piperidine]-1'-carboxylate

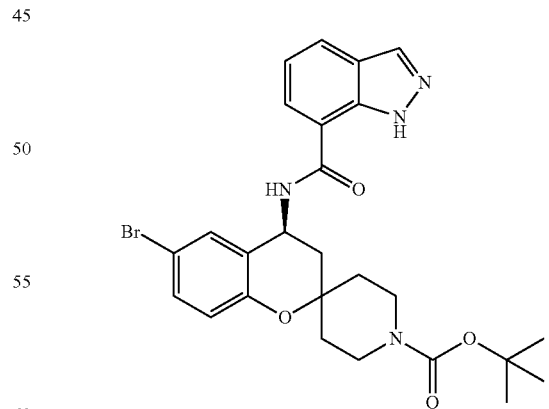

To a stirred solution of tert-butyl (S)-4-amino-6-bromo-spiro[chromane-2,4'-piperidine]-1'-carboxylate (1.51 g, 3.80 mmol) and 1H-indazole-7-carboxylic acid (0.678 g, 4.18 mmol) in DMF (15 mL) was added DIEA (2.00 mL, 11.4 mmol) followed by HATU (1.88 g, 4.94 mmol). The resulting solution was stirred at RT. After 2 hours LCMS indicated complete reaction. The solution was partitioned between EtOAc and 10% aqueous citric acid and the phases separated. The aqueous phase was extracted once with EtOAc. The combined EtOAc solutions were washed with 10% aqueous citric acid (2×), saturated aqueous NaHCO$_3$ (2×), dried over Na$_2$SO$_4$, and concentrated at reduced pressure. The crude product was purified by flash chromatography (silica gel, 0-100% EtOAc/hexanes, gradient elution) to afford the title compound as a white solid (1.87 g, 91% yield). LCMS (ESI) m/z calcd for C$_{26}$H$_{29}$BrN$_4$O$_4$: 540.14. Found: 541.33 (M+1)$^+$. $^1$H NMR (400 MHz, CDCl$_3$) δ 8.13 (s, 1H), 7.96 (d, J=8.2 Hz, 1H), 7.60 (d, J=7.4 Hz, 1H), 7.42 (d, J=2.0 Hz, 1H), 7.28 (dd, J=8.8, 2.2 Hz, 1H), 7.19 (t, J=7.6 Hz, 1H), 6.77 (d, J=8.6 Hz, 1H), 6.67 (br s, 1H), 5.53-5.67 (m, 1H), 3.75-3.99 (m, 2H), 2.96-3.38 (m, 2H), 2.34 (dd, J=13.5, 6.4 Hz, 1H), 1.76-1.96 (m, 3H), 1.54-1.74 (m, 2H), 1.45 (s, 9H).

Step 5: Preparation of (S)—N-(6-bromospiro[chroman-2,4'-piperidin]-4-yl)-1H-indazole-7-carboxamide dihydrochloride

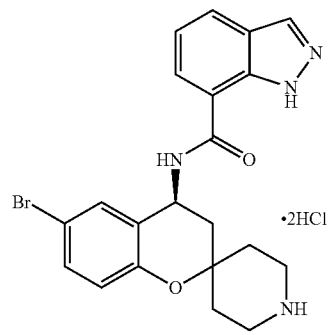 [SMILES: O=C(N[C@H]1CC2(CCNCC2)Oc2ccc(Br)cc21)c1cccc2cn[nH]c12]

To a stirred solution of tert-butyl (S)-6-bromo-4-(1H-indazole-7-carboxamido)spiro[chromane-2,4'-piperidine]-1'-carboxylate (1.80 g, 3.32 mmol) in DCM (35 mL) was added 4N HCl/dioxane (12.5 mL, 49.9 mmol). The resulting solution was stirred at RT. After 18 hours LCMS indicated complete reaction. The suspension was concentrated to dryness at reduced pressure. The residue was suspended in DCM and evaporated a second time to give afford the title compound as a white solid in quantitative yield. LCMS (ESI) m/z calcd for C$_{21}$H$_{21}$BrN$_4$O$_2$: 440.09. Found: 441.21 (M+1)$^+$. $^1$H NMR (400 MHz, DMSO-d$_6$) δ 9.00-9.31 (m, 3H), 8.17 (s, 1H), 7.97 (dd, J=7.4, 4.7 Hz, 2H), 7.31-7.39 (m, 2H), 7.19 (t, J=7.6 Hz, 1H), 6.89 (d, J=9.4 Hz, 1H), 5.39-5.51 (m, 1H), 3.08-3.28 (m, 2H), 2.91-3.05 (m, 1H), 2.23 (dd, J=13.7, 6.3 Hz, 1H), 1.80-2.12 (m, 5H).

Step 6: Preparation of (S)-isopropyl 6-bromo-4-(1H-indazole-7-carboxamido)spiro[chroman-2,4'-piperidine]-1'-carboxylate

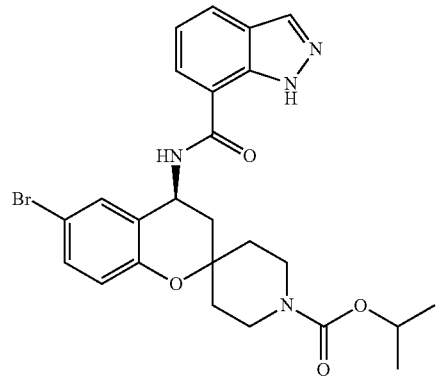 [SMILES: CC(C)OC(=O)N1CCC2(CC1)C[C@H](NC(=O)c1cccc3cn[nH]c13)c1cc(Br)ccc1O2]

To a stirred suspension of (S)—N-(6-bromospiro[chromane-2,4'-piperidin]-4-yl)-1H-indazole-7-carboxamide dihydrochloride (50 mg, 0.097 mmol) in DCM (4 mL) at 0° C. was added TEA (68 uL, 0.49 mmol). The resulting solution was treated with 1.0 M isopropyl chloroformate/PhMe (97 uL, 0.097 mmol) by dropwise addition. After 30 minutes TLC and LCMS indicated complete reaction. The solution was treated with 2M ammonia/MeOH (3 mL), stirred for an additional 10 minutes, and then concentrated to dryness at reduced pressure. The residue was subjected to RP-HPLC purification (C18, 10-100% MeCN/water with 0.1% FA) to afford the title compound as a white solid (35 mg, 68% yield). LCMS (ESI) m/z calcd for C$_{25}$H$_{27}$BrN$_4$O$_4$: 526.12. Found: 527.29 (M+1)$^+$. $^1$H NMR (400 MHz, CDCl$_3$) δ 8.14 (s, 1H), 7.98 (d, J=7.8 Hz, 1H), 7.58 (d, J=7.4 Hz, 1H), 7.43 (d, J=2.0 Hz, 1H), 7.31 (dd, J=8.6, 2.3 Hz, 1H), 7.21 (t, J=7.6 Hz, 1H), 6.80 (d, J=8.6 Hz, 1H), 6.54 (d, J=8.2 Hz, 1H), 5.52-5.65 (m, 1H), 4.85-4.98 (m, 1H), 3.96 (br s, 2H), 3.28-3.41 (m, 1H), 3.04-3.18 (m, 1H), 2.34 (dd, J=13.5, 6.4 Hz, 1H), 1.79-1.98 (m, 3H), 1.48-1.77 (m, 2H), 1.24 (d, J=5.9 Hz, 6H).

Example 7: (S)-ethyl 4-(1H-indazole-7-carboxamido)spiro[chroman-2,4'-piperidine]-1'-carboxylate

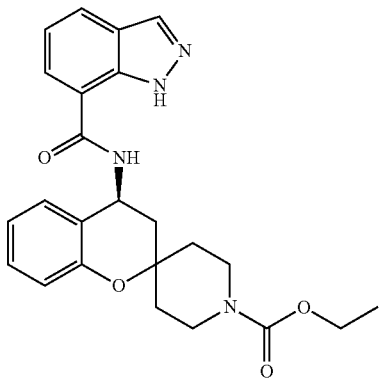 [SMILES: CCOC(=O)N1CCC2(CC1)C[C@H](NC(=O)c1cccc3cn[nH]c13)c1ccccc1O2]

A solution of ethyl (S)-6-bromo-4-(1H-indazole-7-carboxamido)spiro[chromane-2,4'-piperidine]-1'-carboxylate (0.400 g, 0.779 mmol) in MeOH (30 mL) was subjected to hydrogenation at 60 psi in the presence of 10% Pd(C) (0.250 g, 0.235 mmol). After 3 hours LCMS indicated complete reaction. The vessel was purged with nitrogen, catalyst removed by filtration, and the filtrate concentrated to dryness at reduced pressure. The residue was dissolved in DCM. The solution was washed with saturated aqueous NaHCO$_3$ (2×), dried over Na$_2$SO$_4$ and concentrated to dryness at reduced pressure. The residue was subjected to flash chromatography (silica gel, 0-100% EtOAc/DCM, gradient elution) to give the title compound as a white solid (0.224 g, 66% yield). LCMS (ESI) m/z calcd for C$_{24}$H$_{26}$N$_4$O$_4$: 434.20. Found: 435.31 (M+1)$^+$. $^1$H NMR (400 MHz, CDCl$_3$) δ 11.8 (br s, 1H), 8.13 (s, 1H), 7.96 (d, J=7.8 Hz, 1H), 7.55 (d, J=7.4 Hz, 1H), 7.33 (d, J=7.4 Hz, 1H), 7.14-7.27 (m, 2H), 6.87-6.97 (m, 2H), 6.58 (br s, 1H), 5.54-5.67 (m, 1H), 4.13 (q, J=7.0 Hz, 2H), 3.97 (br s, 2H), 3.29-3.43 (m, 1H), 3.06-3.23 (m, 1H), 2.37 (dd, J=13.3, 6.6 Hz, 1H), 1.80-2.02 (m, 3H), 1.55-1.77 (m, 2H), 1.26 (t, J=7.03 Hz, 3H).

Example 8: (S)-ethyl 6-bromo-4-(1H-indole-4-carboxamido)spiro[chroman-2,4'-piperidine]-1'-carboxylate

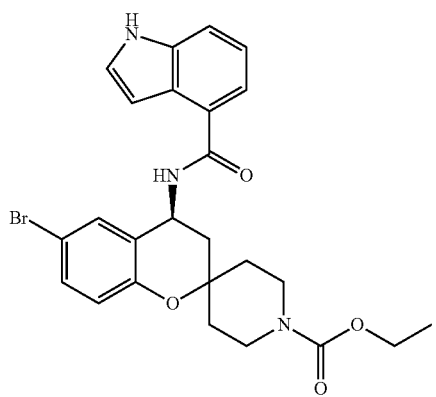 [SMILES: CCOC(=O)N1CCC2(CC1)C[C@H](NC(=O)c1cccc3[nH]ccc13)c1cc(Br)ccc1O2]

The title compound was prepared in 90% yield from (S)-ethyl 4-amino-6-bromospiro[chroman-2,4'-piperidine]-1'-carboxylate hydrochloride and 1H-indole-4-carboxylic acid according to the procedure described herein for the synthesis of (S)-ethyl 6-bromo-4-(1H-indole-7-carboxamido)spiro[chroman-2,4'-piperidine]-1'-carboxylate.
LCMS (ESI) m/z calcd for C$_{25}$H$_{26}$BrN$_3$O$_4$: 511.11. Found: 512.28 (M+1)$^+$. $^1$H NMR (400 MHz, methanol-d$_4$) δ 7.57 (d, J=8.2 Hz, 1H), 7.49-7.40 (m, 2H), 7.37 (d, J=2.7 Hz, 1H), 7.28 (d, J=8.2 Hz, 1H), 7.17 (t, J=7.6 Hz, 1H), 6.87 (d, J=2.3 Hz, 1H), 6.81 (d, J=9.0 Hz, 1H), 5.60-5.50 (m, 1H), 4.12 (q, J=7.0 Hz, 2H), 4.02-3.86 (m, 2H), 3.52-3.34 (m, 1H), 3.24-3.07 (m, 1H), 2.28-2.16 (m, 1H), 2.07-1.91 (m, 2H), 1.90-1.61 (m, 3H), 1.26 (t, J=7.0 Hz, 3H).

Example 9: ethyl 4'-(1H-indazole-7-carboxamido)-6'-methoxy-3',4'-dihydrospiro[piperidine-4,2'-pyrano[3,2-b]pyridine]-1-carboxylate

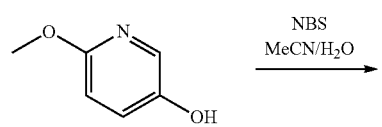

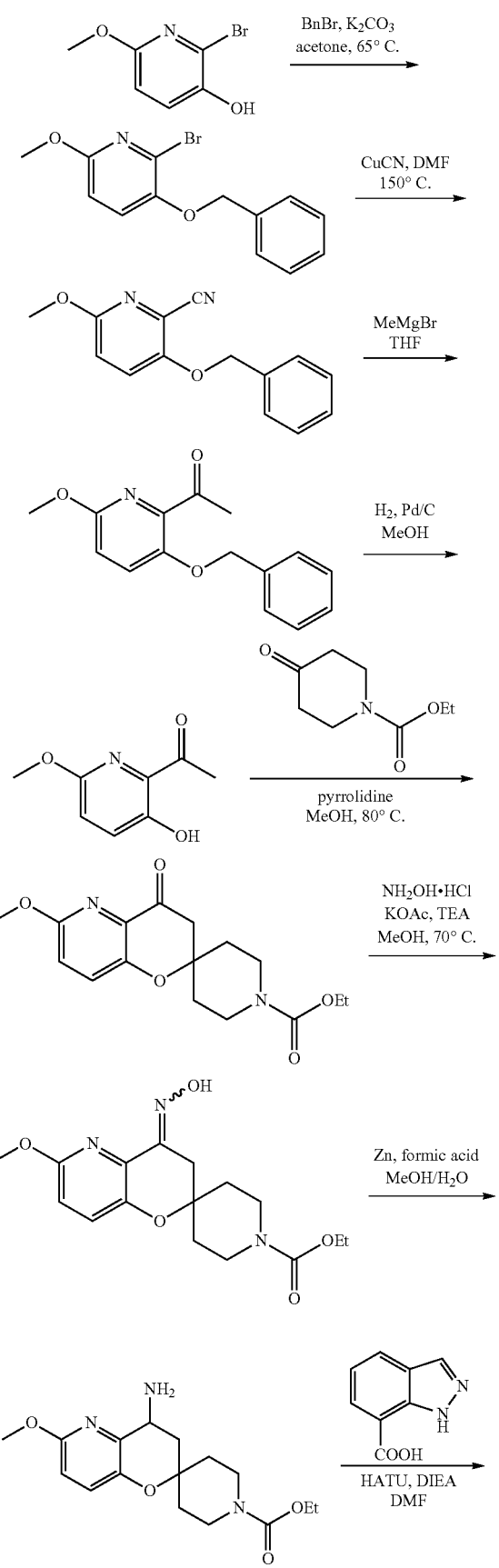

-continued

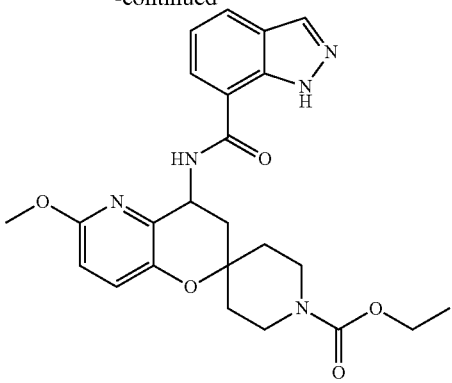

Step 1: Preparation of 2-bromo-6-methoxypyridin-3-ol

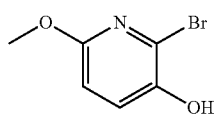

To a stirred solution of 6-methoxypyridin-3-ol (6.00 g, 48.0 mmol) in MeCN (130 mL) and water (25 mL) at 0° C. was added NBS (9.39 g, 52.7 mmol). The reaction mixture was allowed to warm to RT and the reaction progress monitored by LCMS. Once the reaction was complete, the mixture was mixed with ice water (120 mL) and extracted with EtOAc (2x). The combined EtOAc solutions were washed with brine, dried over $Na_2SO_4$, and concentrated at reduced pressure. The crude material was purified by flash chromatography (silica gel, 30% EtOAc/PE) to afford the title compound as a pale yellow solid (6.0 g, 61% yield). LCMS (ESI) m/z calcd for $C_6H_6BrNO_2$: 202.96. Found: 204.00 $(M+1)^+$.

Step 2: Preparation of 3-(benzyloxy)-2-bromo-6-methoxypyridine

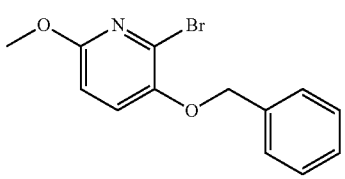 [SMILES: COc1ccc(OCc2ccccc2)c(C#N)n1]

To a stirred solution of 2-bromo-6-methoxypyridin-3-ol (6.00 g, 29.4 mmol) in acetone (120 mL) was added benzyl bromide (3.85 mL, 32.3 mmol) followed by $K_2CO_3$ (8.14 g, 58.8 mmol) and the resulting mixture stirred at 65° C. After 16 hours, the mixture was cooled to RT, filtered to remove solids, the filter cake washed with acetone, and the filtrate concentrated at reduced pressure. The residue was subjected to flash chromatography (silica gel, 30% EtOAc/PE) to afford the title compound as a pale yellow liquid (6.00 g, 69% yield). LCMS (ESI) m/z calcd for $C_{13}H_{12}BrNO_2$: 293.01. Found: 294.08 $(M+1)^+$.

Step 3: Preparation of 3-(benzyloxy)-6-methoxypicolinonitrile

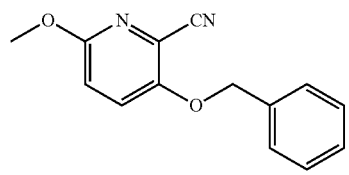

To a stirred solution of 3-(benzyloxy)-2-bromo-6-methoxypyridine (6.00 g, 18.4 mmol) in DMF (100 mL) was added CuCN (6.58 g, 73.4 mmol). The resulting mixture was heated to 150° C. After 16 hours the mixture was cooled to RT and diluted with EtOAc (300 mL). The mixture was filtered to remove solids and the filtrate concentrated at reduced pressure. The crude residue was subjected to flash chromatography (silica gel, 20% EtOAc/PE) to afford the title compound as a pale yellow liquid (3.50 g, 75%). LCMS (ESI) m/z calcd for $C_{14}H_{12}N_2O_2$: 240.09. Found: 241.08 $(M+1)^+$.

Step 4: Preparation of 1-(3-(benzyloxy)-6-methoxypyridin-2-yl)ethanone

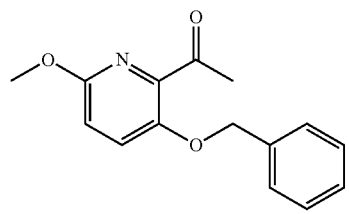 [SMILES: COc1ccc(OCc2ccccc2)c(C(C)=O)n1]

To a stirred solution of 3-(benzyloxy)-6-methoxypicolinonitrile (3.00 g, 11.7 mmol) in THF (30 mL) at RT was slowly added 3M MeMgBr/THF (39.1 mL, 117 mmol). After 16 hours, the solution was quenched by addition of 1N aqueous HCl, stirred for 1 hour, and then basified by addition of 2M aqueous NaOH. The resulting mixture was extracted with EtOAc (2x). The combined extracts were dried over $Na_2SO_4$ and concentrated at reduced pressure. The crude material was purified by flash chromatography (silica gel, 20% EtOAc/hexanes) to afford the title compound in 29% yield. LCMS (ESI) m/z calcd for $C_{15}H_{15}NO_3$: 257.11. Found: 258.07 $(M-1)^+$.

Step 5: Preparation of 1-(3-hydroxy-6-methoxypyridin-2-yl)ethanone

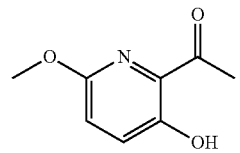

A solution of 1-(3-(benzyloxy)-6-methoxypyridin-2-yl)ethanone (1.10 g, 3.12 mmol) in MeOH (10 mL) was subjected to hydrogenation in the presence of 10% Pd/C (0.531 g). After 16 hours the vessel was purged with nitrogen, catalyst removed by filtration, and the filtrate concentrated to dryness at reduced pressure. The residue was subjected to flash chromatography (silica gel, 10% EtOAc/PE) to afford the title compound (0.50 g, 90% yield). LCMS (ESI) m/z calcd for $C_8H_9NO_3$: 167.06. Found: 168.06 $(M-1)_+$. Preparation of ethyl 6'-methoxy-4'-oxo-3',4'-dihydrospiro[piperidine-4,2'-pyrano[3,2-b]pyridine]-1-carboxylate

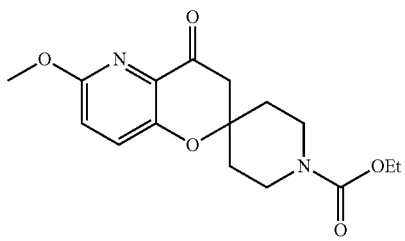 [SMILES: CCOC(=O)N1CCC2(CC1)CC(=O)c1nc(OC)ccc1O2]

Step 6: To a stirred solution of 1-(3-hydroxy-6-methoxy-pyridin-2-yl)ethanone (0.480 g, 2.70 mmol) in MeOH (3 mL) in a screw capped pressure vessel was added pyrrolidine (0.379 mL, 4.59 mmol) followed by ethyl 4-oxopiperidine-1-carboxylate (0.601 g, 3.51 mmol). The vessel was sealed and the solution heated to 80° C. After 4 hours the solution was cooled to RT and concentrated at reduced pressure. The residue was dissolved in EtOAc. The solution was washed with brine, dried over $Na_2SO_4$, and concentrated to dryness. The crude product was purified by flash chromatography (silica gel, 10% EtOAc/PE) to give the title compound in 54% yield. LCMS (ESI) m/z calcd for $C_{16}H_{20}N_{12}O_5$: 320.14. Found: 321.37 $(M+1)^+$.

Step 7: Preparation of ethyl 4'-(hydroxyimino)-6'-methoxy-3',4'-dihydrospiro[piperidine-4,2'-pyrano[3,2-b]pyridine]-1-carboxylate

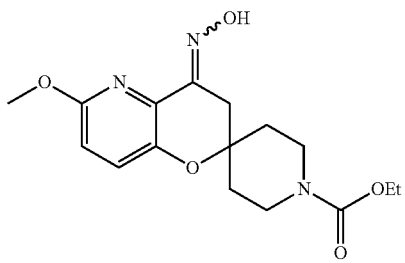 [SMILES: CCOC(=O)N1CCC2(CC1)CC(=NO)c1nc(OC)ccc1O2]

To a stirred solution of ethyl 6'-methoxy-4'-oxo-3',4'-dihydrospiro[piperidine-4,2'-pyrano[3,2-b]pyridine]-1-carboxylate (0.450 g, 1.31 mmol) in MeOH (3 mL) was added hydroxylamine hydrochloride (0.363 g, 5.23 mmol), potassium acetate (0.513 g, 5.23 mmol), and TEA (0.728 mL, 5.23 mmol). The resulting mixture was heated at 70° C. for 20 hours and then cooled to RT. The mixture was filtered to remove solids and the filtrated concentrated to dryness at reduced pressure. The crude residue was subjected to flash chromatography (silica gel, 10% EtOAc/PE) to afford the title compound a s a white solid (0.420 g, 94% yield). LCMS (ESI) m/z calcd for $C_{16}H_{21}N_3O_5$: 335.15. Found: 336.42 $(M+1)^+$.

Step 8: Preparation of ethyl 4'-amino-6'-methoxy-3',4'-dihydrospiro[piperidine-4,2'-pyrano[3,2-b]pyridine]-1-carboxylate

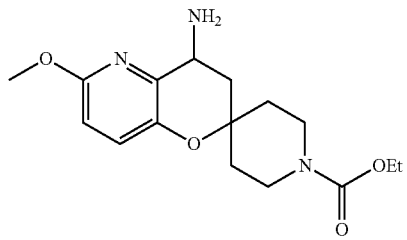 [SMILES: CCOC(=O)N1CCC2(CC1)CC(N)c1nc(OC)ccc1O2]

To a stirred solution of 4'-(hydroxyimino)-6'-methoxy-3',4'-dihydrospiro[piperidine-4,2'-pyrano[3,2-b]pyridine]-1-carboxylate (0.420 g, 1.25 mmol) in 1:1 MeOH/water (8 mL) was added zinc dust (0.819 g, 12.5 mmol) followed by formic acid (0.721 mL, 18.8 mmol). After stirring at RT for 16 hours, the solids were removed by filtration, and the filtrate concentrated at reduced pressure to afford the title compound as a brown solid (0.370 g, 89% yield) which was used in the next step without further purification. LCMS (ESI) m/z calcd for $C_{16}H_{23}N_3O_4$: 321.17. Found: 322.12 $(M+1)^+$.

Step 9: Preparation of ethyl 4'-(1H-indazole-7-carboxamido)-6'-methoxy-3',4'-dihydrospiro[piperidine-4,2'-pyrano[3,2-b]pyridine]-1-carboxylate

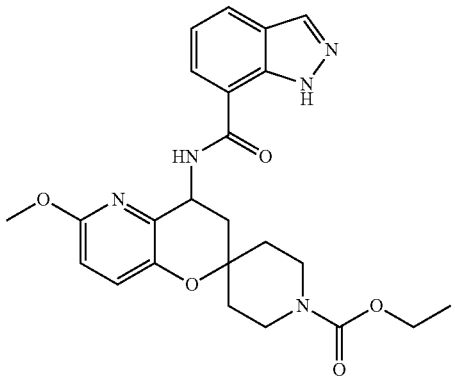 [SMILES: CCOC(=O)N1CCC2(CC1)CC(NC(=O)c1cccc3cn[nH]c13)c1nc(OC)ccc1O2]

To a stirred solution of 1H-indazole-7-carboxylic acid (0.106 g, 0.652 mmol) in DCM (5 mL) was added HATU (0.310 g, 0.815 mmol) followed by DIEA (0.474 mL, 2.72 mmol). After stirring at RT for 10 minutes, the solution was treated with ethyl 4'-amino-6'-methoxy-3',4'-dihydrospiro[piperidine-4,2'-pyrano[3,2-b]pyridine]-1-carboxylate (0.180 g, 0.560 mmol). After 16 hours the solution was concentrated to dryness at reduced pressure and the residue was suspended in water (5 mL). The mixture was stirred for 10 minutes, and the aqueous solution decated away from the solid which was then dissolved in DCM. The DCM solution was dried over $Na_2SO_4$ and concentrated to dryness at reduced pressure. The crude product was purified by reverse phase HPLC (C18, 10-100% MeCN/water with 10 mM $NH_4HCO_3$ in water) to afford the title compound as an off-white solid (33 mg, 13% yield). LCMS (ESI) m/z calcd for $C_{24}H_{27}N_5O_5$: 465.20. Found: 466.16 $(M+1)^+$. $^1$H NMR (400 MHz, DMSO-d$_6$) δ 13.06 (br s, 1H), 8.83 (d, J=7.7 Hz, 1H), 8.14 (s, 1H), 7.94 (t, J=8.4 Hz, 2H), 7.28 (d, J=8.8 Hz, 1H), 7.19 (t, J=7.6 Hz, 1H), 6.68 (d, J=8.8 Hz, 1H), 5.23-5.40 (m, 1H), 4.05 (q, J=7.0 Hz, 2H), 3.73-3.87 (m, 2H), 3.63 (s, 3H), 3.05-3.42 (m, 2H), 2.30 (dd, J=13.6, 6.6 Hz, 1H), 2.03-2.16 (m, 1H), 1.57-1.95 (m, 4H), 1.19 (t, J=7.0 Hz, 3H).

Examples 10-49 were prepared using methods similar to those described herein for examples 1-9.

Example 10: (S)-ethyl 4-(2-aminobenzamido)-6-bromospiro[chroman-2,4'-piperidine]-1'-carboxylate

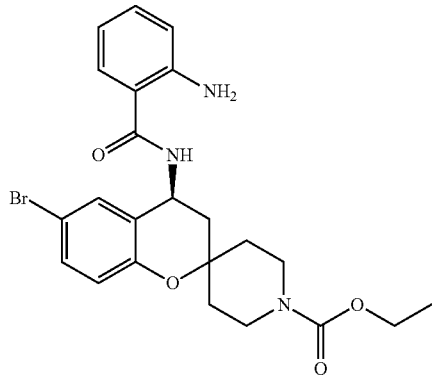 [SMILES: CCOC(=O)N1CCC2(CC1)C[C@H](NC(=O)c1ccccc1N)c1cc(Br)ccc1O2]

Example 11: (S)-propyl 6-bromo-4-(1H-indazole-7-carboxamido)spiro[chroman-2,4'-piperidine]-1'-carboxylate

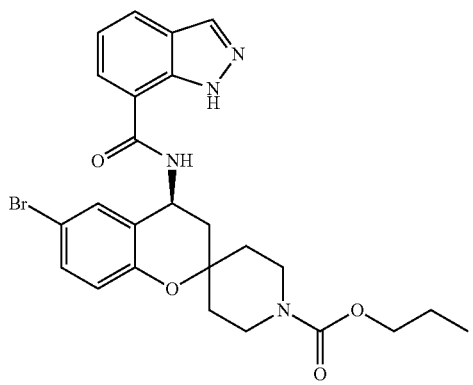 [SMILES: CCCOC(=O)N1CCC2(CC1)C[C@H](NC(=O)c1cccc3cn[nH]c13)c1cc(Br)ccc1O2]

Example 12: (S)-ethyl 6-bromo-4-(1H-indazole-4-carboxamido)spiro[chroman-2,4'-piperidine]-1'-carboxylate

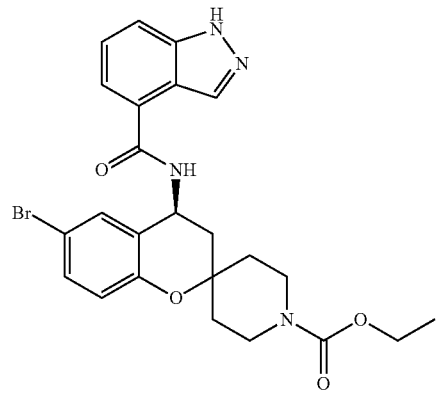 [SMILES: CCOC(=O)N1CCC2(CC1)C[C@H](NC(=O)c1cccc3[nH]ncc13)c1cc(Br)ccc1O2]

Example 13: ethyl 4-(1H-indazole-7-carboxamido)spiro[chroman-2,4'-piperidine]-1'-carboxylate

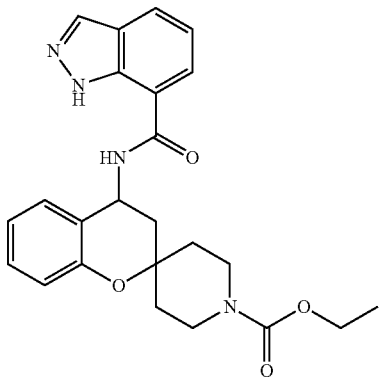 [SMILES: CCOC(=O)N1CCC2(CC1)CC(NC(=O)c1cccc3cn[nH]c13)c1ccccc1O2]

Example 14: (S)-ethyl 6-bromo-4-(2-hydroxybenzamido)spiro[chroman-2,4'-piperidine]-1'-carboxylate

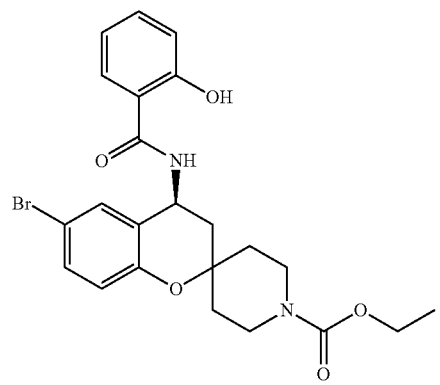

Example 15: ethyl 4-(1H-indole-7-carboxamido) spiro[chroman-2,4'-piperidine]-1'-carboxylate Example 18: ethyl 6-(hydroxymethyl)-4-(1H-indazole-7-carboxamido)spiro[chroman-2,4'-piperidine]-1'-carboxylate

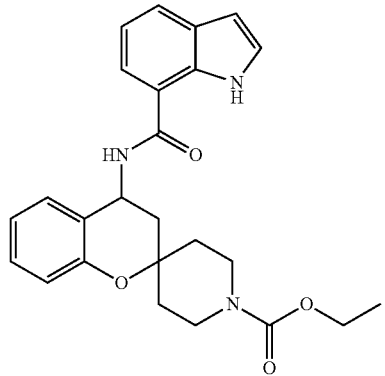 [SMILES: CCOC(=O)N1CCC2(CC1)CC(NC(=O)c1cccc3cc[nH]c13)c1ccccc1O2]

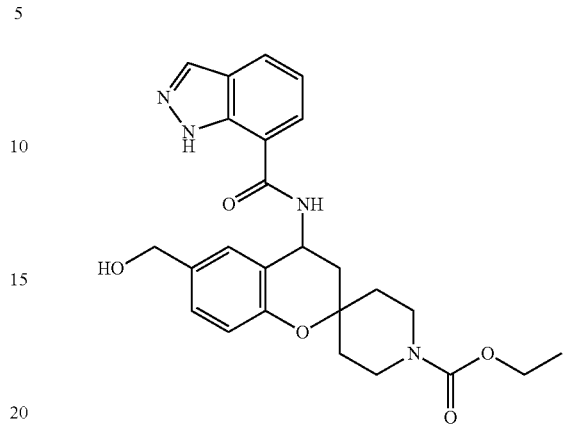

Example 16: ethyl 6'-bromo-4'-(1H-indazole-7-carboxamido)-3',4'-dihydrospiro[piperidine-4,2'-pyrano[2,3-c]pyridine]-1-carboxylate Example 19: 1'-ethyl 6-methyl 4-(1H-indazole-7-carboxamido)spiro[chroman-2,4'-piperidine]-1',6-dicarboxylate

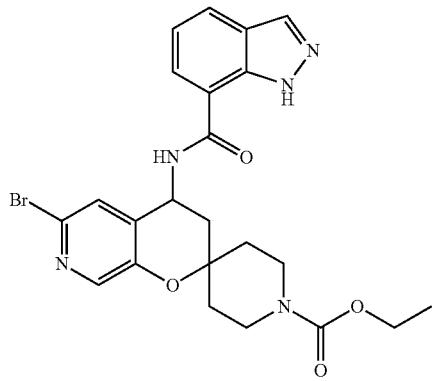

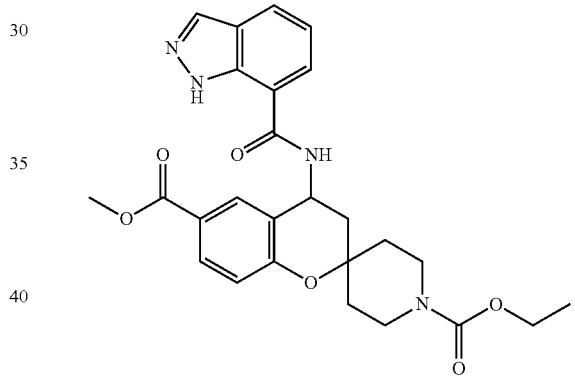

Example 17: ethyl 5-bromo-4-(1H-indole-7-carboxamido)spiro[chroman-2,4'-piperidine]-1'-carboxylate Example 20: (S)-ethyl 6-bromo-4-(2-methoxybenzamido)spiro[chroman-2,4'-piperidine]-1'-carboxylate

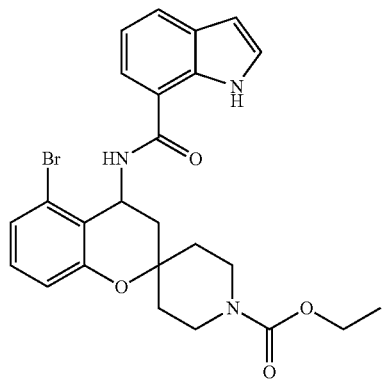 [SMILES: CCOC(=O)N1CCC2(CC1)CC(NC(=O)c1cccc3cc[nH]c13)c1c(Br)cccc1O2]

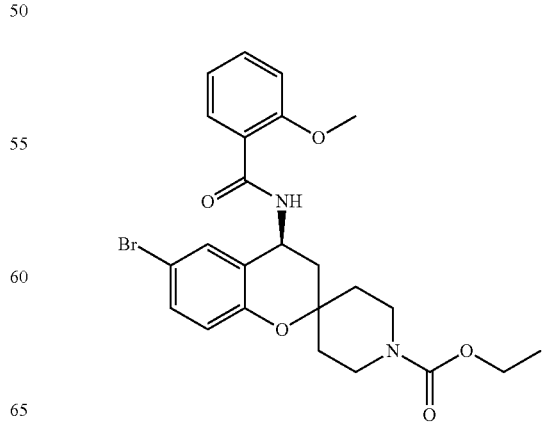

Example 21: ethyl 6-bromo-4-(nicotinamido)spiro[chroman-2,4'-piperidine]-1'-carboxylate

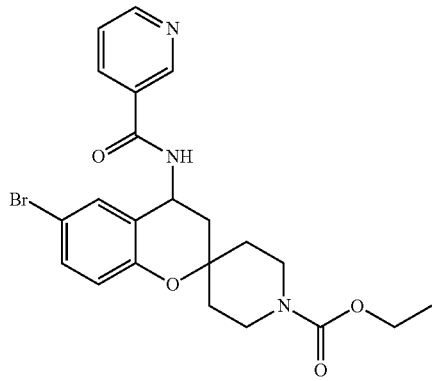 [SMILES: CCOC(=O)N1CCC2(CC1)CC(NC(=O)c1cccnc1)c1cc(Br)ccc1O2]

Example 22: (S)—N-(6-bromo-1'-butyrylspiro[chroman-2,4'-piperidin]-4-yl)-1H-indazole-7-carboxamide

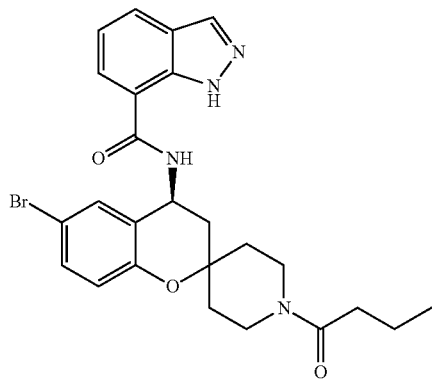 [SMILES: CCCC(=O)N1CCC2(CC1)C[C@H](NC(=O)c1cccc3cn[nH]c13)c1cc(Br)ccc1O2]

Example 23: ethyl 6'-bromo-4'-(1H-indazole-7-carboxamido)-3',4'-dihydrospiro[piperidine-4,2'-pyrano[2,3-b]pyridine]-1-carboxylate

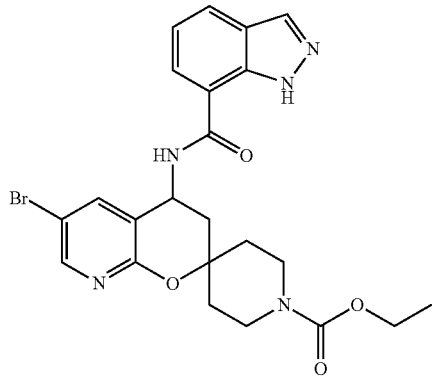 [SMILES: CCOC(=O)N1CCC2(CC1)CC(NC(=O)c1cccc3cn[nH]c13)c1cc(Br)cnc1O2]

Example 24: ethyl 7-bromo-4-(1H-indole-7-carboxamido)spiro[chroman-2,4'-piperidine]-1'-carboxylate

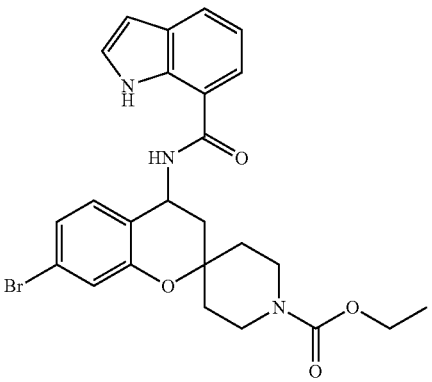 [SMILES: CCOC(=O)N1CCC2(CC1)CC(NC(=O)c1cccc3cc[nH]c13)c1ccc(Br)cc1O2]

Example 25: (S)-ethyl 6-bromo-4-(6-hydroxypicolinamido)spiro[chroman-2,4'-piperidine]-1'-carboxylate

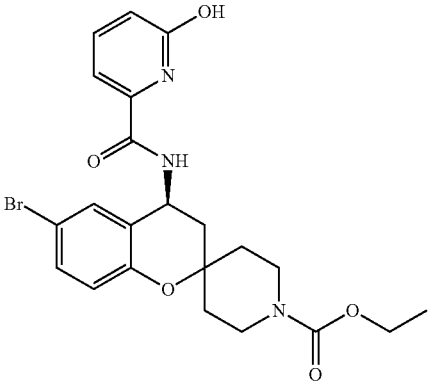 [SMILES: CCOC(=O)N1CCC2(CC1)C[C@H](NC(=O)c1cccc(O)n1)c1cc(Br)ccc1O2]

Example 26: ethyl 4-(1H-pyrazolo[4,3-c]pyridine-7-carboxamido)spiro[chroman-2,4'-piperidine]-1'-carboxylate

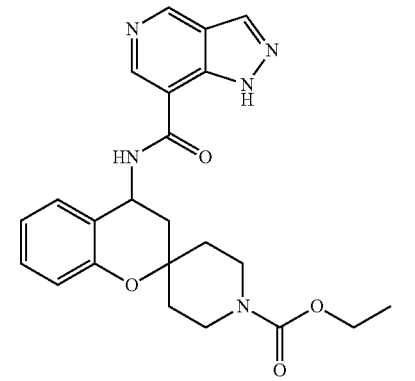

Example 27: tert-butyl 4-(1H-indole-7-carbox-
amido)spiro[chroman-2,4'-piperidine]-1'-carboxylate

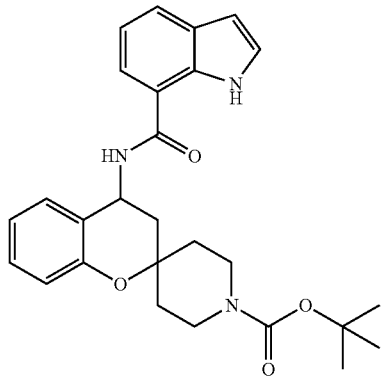 [SMILES: CC(C)(C)OC(=O)N1CCC2(CC1)CC(NC(=O)c1cccc3cc[nH]c13)c1ccccc1O2]

Example 28: (S)-tert-butyl 6-bromo-4-(1H-indazole-
7-carboxamido)spiro[chroman-2,4'-piperidine]-1'-
carboxylate

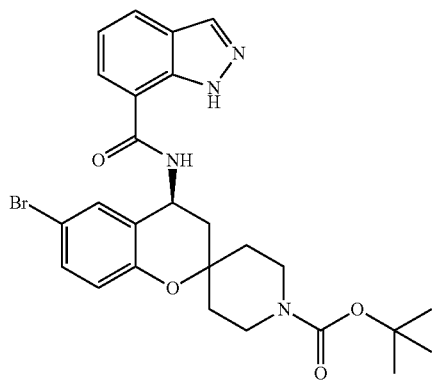 [SMILES: CC(C)(C)OC(=O)N1CCC2(CC1)C[C@H](NC(=O)c1cccc3cn[nH]c13)c1cc(Br)ccc1O2]

Example 29: ethyl 4'-(1H-indazole-7-carboxamido)-
3',4'-dihydrospiro[piperidine-4,2'-pyrano[3,2-b]pyri-
dine]-1-carboxylate

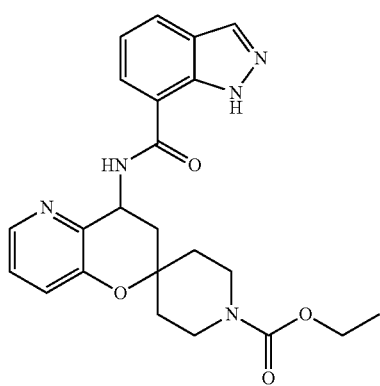 [SMILES: CCOC(=O)N1CCC2(CC1)CC(NC(=O)c1cccc3cn[nH]c13)c1ncccc1O2]

Example 30: ethyl 4-(5-fluoronicotinamido)spiro
[chroman-2,4'-piperidine]-1'-carboxylate

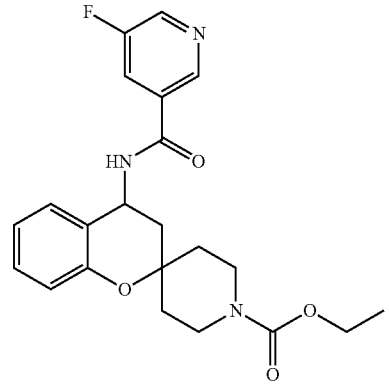 [SMILES: CCOC(=O)N1CCC2(CC1)CC(NC(=O)c1cncc(F)c1)c1ccccc1O2]

Example 31: (S)-phenyl 6-bromo-4-(1H-indazole-7-
carboxamido)spiro[chroman-2,4'-piperidine]-1'-car-
boxylate

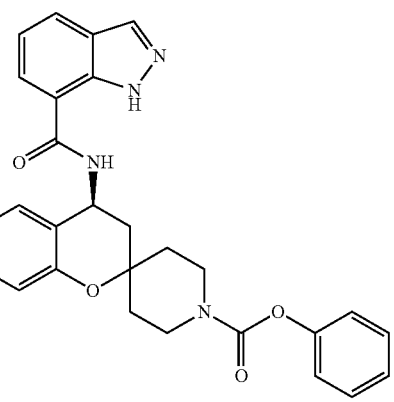

Example 32: (S)-ethyl 6-bromo-4-(1H-imidazole-2-
carboxamido)spiro[chroman-2,4'-piperidine]-1'-car-
boxylate

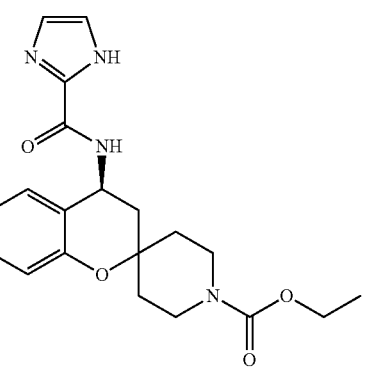

Example 33: ethyl 4'-(1H-indazole-7-carboxamido)-3',4'-dihydrospiro[piperidine-4,2'-pyrano[2,3-c]pyridine]-1-carboxylate

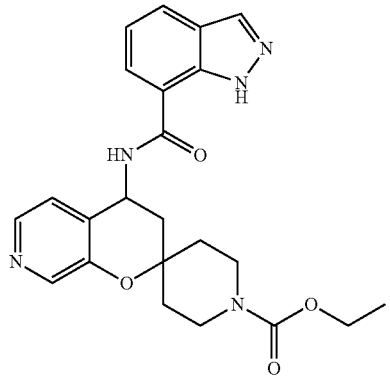 [SMILES: CCOC(=O)N1CCC2(CC1)CC(NC(=O)c1cccc3cn[nH]c13)c1ccncc1O2]

Example 36: (R)-ethyl 6-bromo-4-(1H-indole-7-carboxamido)spiro[chroman-2,4'-piperidine]-1'-carboxylate

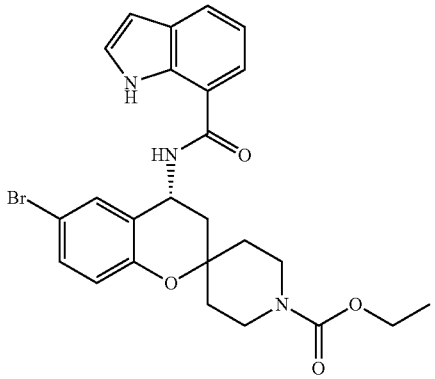

Example 34: ethyl 4-(picolinamido)spiro[chroman-2,4'-piperidine]-1'-carboxylate

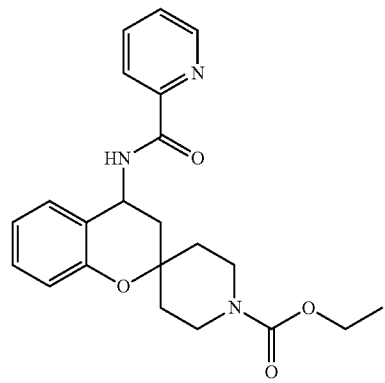 [SMILES: CCOC(=O)N1CCC2(CC1)CC(NC(=O)c1ccccn1)c1ccccc1O2]

Example 37: (R)-ethyl 6-bromo-4-(1H-indazole-7-carboxamido)spiro[chroman-2,4'-piperidine]-1'-carboxylate

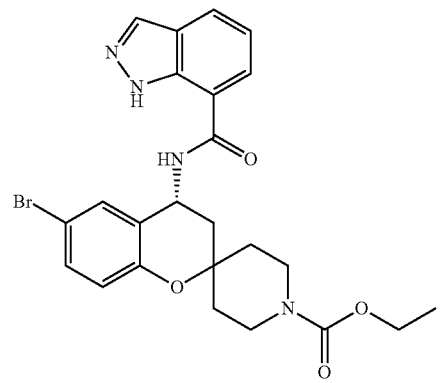

Example 35: ethyl 6'-methoxy-4'-(nicotinamido)-3',4'-dihydrospiro[piperidine-4,2'-pyrano[3,2-b]pyridine]-1-carboxylate

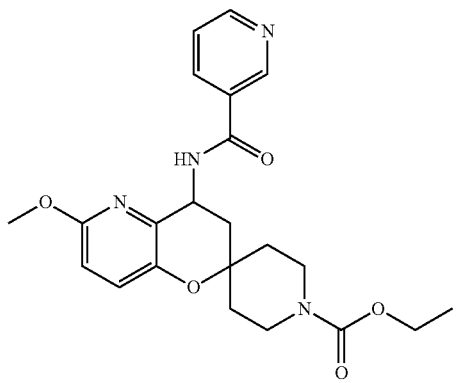 [SMILES: CCOC(=O)N1CCC2(CC1)CC(NC(=O)c1cccnc1)c1nc(OC)ccc1O2]

Example 38: ethyl 4-(1-methyl-1H-indole-7-carboxamido)spiro[chroman-2,4'-piperidine]-1'-carboxylate

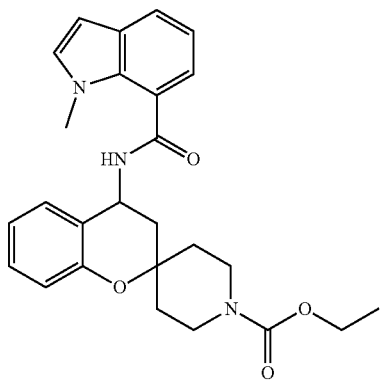 [SMILES: CCOC(=O)N1CCC2(CC1)CC(NC(=O)c1cccc3ccn(C)c13)c1ccccc1O2]

Example 39: ethyl 4-(1H-benzo[d]imidazole-7-carboxamido)spiro[chroman-2,4'-piperidine]-1'-carboxylate

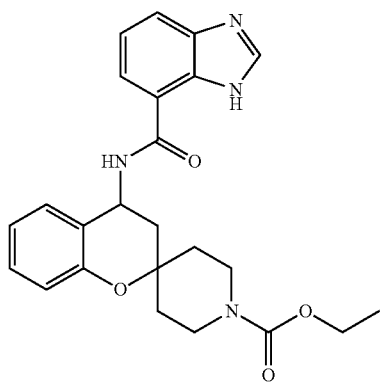 [SMILES: CCOC(=O)N1CCC2(CC1)CC(NC(=O)c1cccc3nc[nH]c13)c1ccccc1O2]

Example 40: ethyl 4-((5-(trifluoromethyl)-1,3,4-thiadiazol-2-yl)amino)spiro[chroman-2,4'-piperidine]-1'-carboxylate

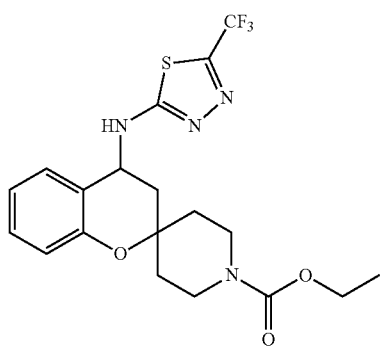 [SMILES: CCOC(=O)N1CCC2(CC1)CC(Nc1nnc(C(F)(F)F)s1)c1ccccc1O2]

Example 41: ethyl 4-(nicotinamido)spiro[chroman-2,4'-piperidine]-1'-carboxylate

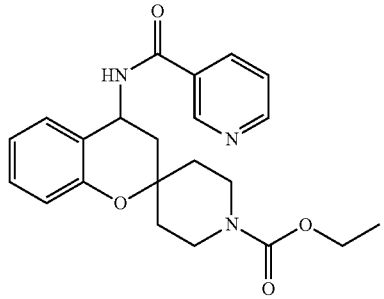 [SMILES: CCOC(=O)N1CCC2(CC1)CC(NC(=O)c1cccnc1)c1ccccc1O2]

Example 42: ethyl 4'-(1H-indazole-7-carboxamido)-3',4'-dihydrospiro[piperidine-4,2'-pyrano[2,3-b]pyridine]-1-carboxylate

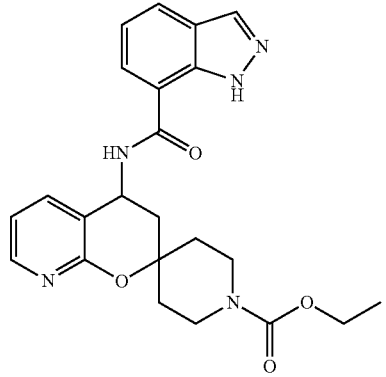 [SMILES: CCOC(=O)N1CCC2(CC1)CC(NC(=O)c1cccc3cn[nH]c13)c1cccnc1O2]

Example 43: ethyl 4-(1-methyl-1H-pyrazole-5-carboxamido)spiro[chroman-2,4'-piperidine]-1'-carboxylate

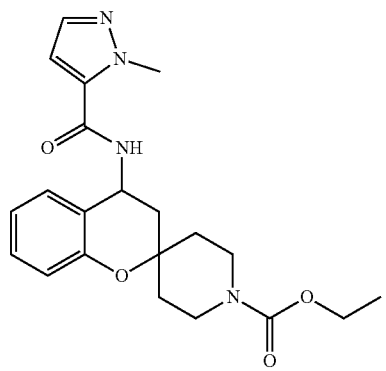 [SMILES: CCOC(=O)N1CCC2(CC1)CC(NC(=O)c1ccnn1C)c1ccccc1O2]

Example 44: (S)-ethyl 6-bromo-4-(1H-pyrazole-5-carboxamido)spiro[chroman-2,4'-piperidine]-1'-carboxylate

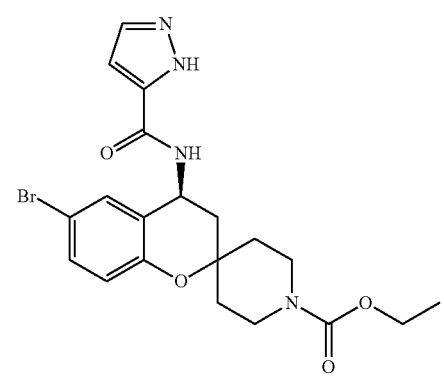 [SMILES: CCOC(=O)N1CCC2(CC1)C[C@H](NC(=O)c1ccn[nH]1)c1cc(Br)ccc1O2]

Example 45: ethyl 4-(pyrimidine-2-carboxamido)spiro[chroman-2,4'-piperidine]-1'-carboxylate Example 48: ethyl 4-(5-cyanonicotinamido)spiro[chroman-2,4'-piperidine]-1'-carboxylate

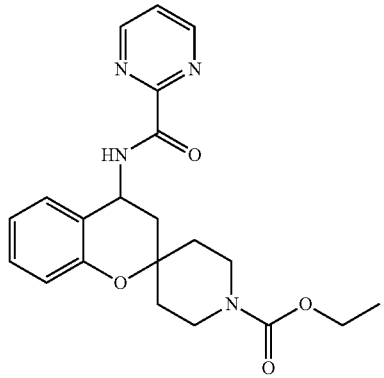 [SMILES: CCOC(=O)N1CCC2(CC1)CC(NC(=O)c1ncccn1)c1ccccc1O2]
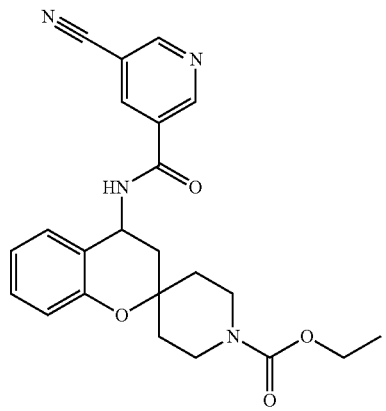

Example 46: ethyl 4-(3-methoxypicolinamido)spiro[chroman-2,4'-piperidine]-1'-carboxylate Example 49: ethyl 4'-(1H-indazole-7-carboxamido)-3',4'-dihydrospiro[piperidine-4,2'-pyrano[3,2-c]pyridine]-1-carboxylate

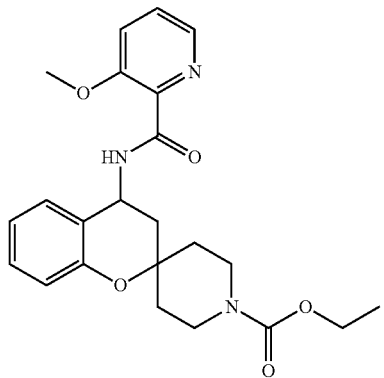 [SMILES: CCOC(=O)N1CCC2(CC1)CC(NC(=O)c1ncccc1OC)c1ccccc1O2]

Example 47: ethyl 4-(1-methyl-1H-imidazole-2-carboxamido)spiro[chroman-2,4'-piperidine]-1'-carboxylate Example 50: 2-amino-2-(hydroxymethyl)propane-1,3-diol hemi((S)-(7-((6-bromo-1-(ethoxycarbonyl)spiro[chroman-2,4'-piperidin]-4-yl)carbamoyl)-2H-indazol-2-yl)methyl phosphate)

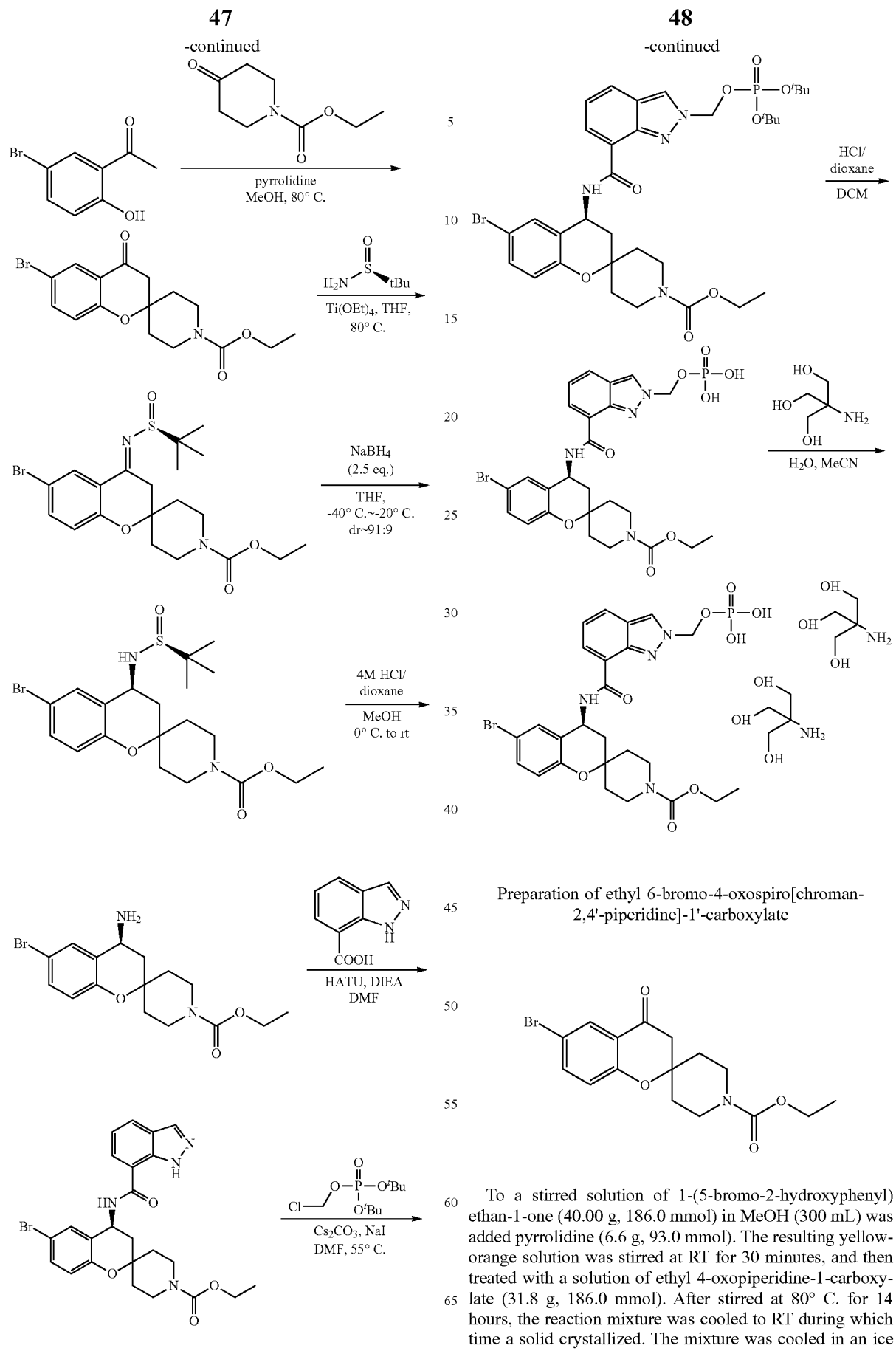

Preparation of ethyl 6-bromo-4-oxospiro[chroman-2,4'-piperidine]-1'-carboxylate

To a stirred solution of 1-(5-bromo-2-hydroxyphenyl)ethan-1-one (40.00 g, 186.0 mmol) in MeOH (300 mL) was added pyrrolidine (6.6 g, 93.0 mmol). The resulting yellow-orange solution was stirred at RT for 30 minutes, and then treated with a solution of ethyl 4-oxopiperidine-1-carboxylate (31.8 g, 186.0 mmol). After stirred at 80° C. for 14 hours, the reaction mixture was cooled to RT during which time a solid crystallized. The mixture was cooled in an ice water bath for 30 minutes, and the solid collected by vacuum filtration, washing with two portions of ice cold MeOH. Drying in vacuo afforded the title compound as a light yellow solid (63.5 g, 92.8%). LCMS (ESI) m/z calcd for $C_{16}H_{18}BrNO_4$: 367.04. Found: 368.14/370.13 (M/M+2)$^+$.

Preparation of (S)-ethyl 6-bromo-4-((S)-1,1-dimethylethylsulfinamido)spiro [chroman-2,4'-piperidine]-1'-carboxylate

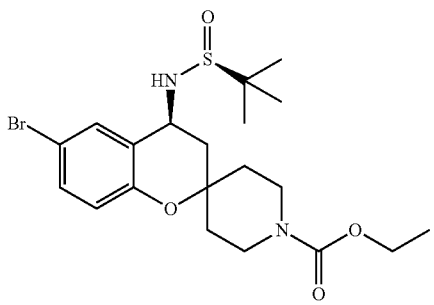

To a stirred solution of ethyl 6-bromo-4-oxospiro[chromane-2,4'-piperidine]-1'-carboxylate (50.00 g, 136.3 mmol) and (S)-2-methylpropane-2-sulfinamide (33.0 g, 272.6 mmol) in anhydrous THF (250 mL) was added Ti(OEt)$_4$ (86 mL, 408.9 mmol). The resulting mixture was heated at 80° C. under a nitrogen atmosphere. After 20 hours, the solution was cooled to –35° C. and treated with NaBH$_4$ (25.8 g, 681.0 mmol). After stirred at –35° C. for 30 minutes the mixture was allowed to warm to –20° C. and stirred overnight. LCMS indicated complete conversion of the imine intermediate to the desired amine product as a 92:8 mixture of diastereomers. The cloudy solution was cooled to 0° C. and quenched by slow addition of MeOH until gas evolution ceased. The resulting mixture was treated with saturated aqueous brine to afford a thick, light yellow suspension. The solid was removed by filtration. The filter cake was washed with EtOAc (3×). The filtrate was washed with saturated brine (1×), dried over Na$_2$SO$_4$, and concentrated at reduced pressure. The residue was subjected to flash chromatography (silica gel, 20-100% EtOAc/DCM, gradient elution) to afford the title compound as a white solid (37.9 g, 59% yield). LCMS (ESI) m/z calcd for $C_{20}H_{29}BrN_2O_4S$: 472.10. Found: 473.41/475.52 (M/M–2)$^+$.

Preparation of (S)-ethyl 4-amino-6-bromospiro [chroman-2,4'-piperidine]-1'-carboxylate hydrochloride

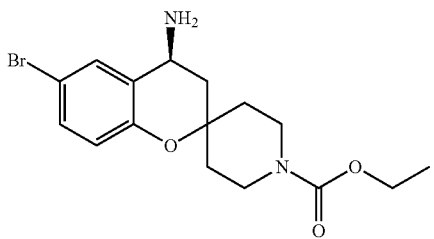

At 0° C., to a stirred suspension of ethyl (S)-6-bromo-4-(((S)-tert-butylsulfinyl)amino) spiro[chromane-2,4'-piperidine]-1'-carboxylate (30.1 g, 63.6 mmol) in anhydrous MeOH (200 mL) was added 4N HCl/dioxane (25.0 mL, 95.4 mmol) drop wise and then the mixture was stirred at room temperature for 3 h. The solution was concentrated to dryness at reduced pressure. The residue was redissolved in MeOH and again concentrated to dryness to afford the title compound as a tan solid in quantitative yield which was used in the following step without further purification. LCMS (ESI) m/z calcd for $C_{16}H_{21}BrN_2O_3$: 368.07. Found: 369.16/371.22 (M/M–2)$^+$.

Preparation of (S)-ethyl 6-bromo-4-(1H-indazole-7-carboxamido)spiro[chroman-2,4'-piperidine]-1'-carboxylate

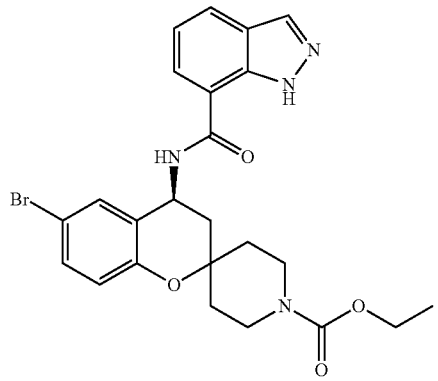

To a stirred solution of (S)-ethyl 4-amino-6-bromospiro [chroman-2,4'-piperidine]-1'-carboxylate hydrochloride (27.6 g, 68.0 mmol) and 1H-indole-7-carboxylic acid (9.9 g, 61.8 mmol) in DMF (300 mL) was added DIEA (32.6 mL, 185.4 mmol) followed by HATU (23.8 g, 68.0 mmol). After stirred at room temperature for 15 hours, the resulting solution was partitioned between EtOAc and 10% aqueous citric acid. After separating the phases, the EtOAc phase was washed with 10% aqueous citric acid (1×), saturated aqueous NaHCO$_3$ (2×), dried over Na$_2$SO$_4$ and concentrated to dryness at reduced pressure. The residue was subjected to flash chromatography (silica gel, 20-100% EtOAc/hexanes) to afford the title compound as a white solid (22.3 g, 71.2% yield). $^1$H NMR (400 MHz, CDCl$_3$) δ 11.78 (s, 1H), 8.15 (s, 1H), 7.98 (d, J=8.0 Hz, 1H), 7.60 (d, J=7.2 Hz, 1H), 7.44 (d, J=1.9 Hz, 1H), 7.31 (dd, J=8.7, 2.3 Hz, 1H), 7.24-7.18 (m, 1H), 6.80 (d, J=8.7 Hz, 1H), 6.61 (s, 1H), 5.65-5.57 (m, 1H), 4.14 (q, J=7.1 Hz, 2H), 4.05-3.85 (m, 2H), 3.43-3.31 (m, 1H), 3.20-3.05 (m, 1H), 2.39-2.31 (m, 1H), 1.97-1.82 (m, 3H), 1.76-1.65 (m, 2H), 1.27 (t, J=7.1 Hz, 3H). LCMS (ESI) m/z calcd for $C_{24}H_{25}BrN_4O_4$: 512.11. Found: 513.15/515.14 (M/M–2)$^+$.

Preparation of ethyl (S)-6-bromo-4-(2-(((di-tert-butoxyphosphoryl)oxy)methyl)-2H-indazole-7-carboxamido)spiro[chromane-2,4'-piperidine]-1'-carboxylate

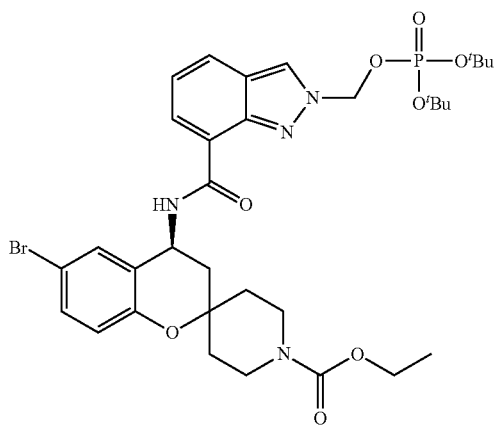 [SMILES: CCOC(=O)N1CCC2(CC1)C[C@H](NC(=O)c1cccc3cn(COP(=O)(OC(C)(C)C)OC(C)(C)C)nc13)c1cc(Br)ccc1O2]

To a stirred suspension of (S)-ethyl 6-bromo-4-(1H-indazole-7-carboxamido)spiro [chroman-2,4'-piperidine]-1'-carboxylate (10.8 g, 21.1 mmol) and $Cs_2CO_3$ (20.6 g, 63.2 mmol) in DMF (100 mL) was added di-tert-butyl (chloromethyl) phosphate (8.2 g, 31.6 mmol), NaI (3.5 g, 23.2 mmol). After stirred at 55° C. for 5 hours, the resulting mixture was partitioned between EtOAc and water. The organic layer was separated and washed with saturated aqueous NaCl (2×), dried over $Na_2SO_4$ and concentrated to dryness at reduced pressure to afford the title compound as a yellow gum (10.3 g, 66.5% yield), which was used in the following step without purification. LCMS (ESI) m/z calcd for $C_{33}H_{44}BrN_4O_8P$: 734.21. Found: 735.50/737.63 $(M/M+2)^+$.

Preparation of ethyl (S)-6-bromo-4-(2-((phosphonooxy)methyl)-2H-indazole-7-carboxamido)spiro[chromane-2,4'-piperidine]-1'-carboxylate

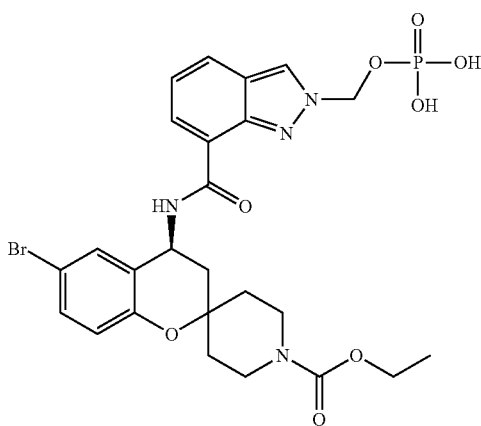

To a stirred solution of ethyl (S)-6-bromo-4-(2-(((di-tert-butoxyphosphoryl)oxy)methyl)-2H-indazole-7-carboxamido)spiro[chromane-2,4'-piperidine]-1'-carboxylate (405 mg, 0.55 mmol) in DCM (4 mL) was added 4 M HCl in dioxane (4.1 mL, 16.5 mmol). After stirred at 25° C. for 3 hours, the resulting mixture was concentrated at reduced pressure to afford a residue, which was dried under high vacuum. The resulting residue was purified by recrystallization in MCN/water (9:1) to afford the title compound as a white solid (233 mg, 68% yield). $^1$H NMR (400 MHz, DMSO) δ 9.40 (d, J=8.3 Hz, 1H), 8.76 (s, 1H), 8.13 (dd, J=7.0, 0.9 Hz, 1H), 8.08-8.02 (m, 1H), 7.42 (d, J=2.0 Hz, 1H), 7.37-7.25 (m, 2H), 6.87 (d, J=8.7 Hz, 1H), 6.18-6.05 (m, 2H), 5.51-5.41 (m, 1H), 4.05 (q, J=7.1 Hz, 2H), 3.88-3.73 (m, 2H), 3.38-3.24 (m, 1H), 3.17-3.04 (m, 1H), 2.37-2.27 (m, 1H), 2.06-1.98 (m, 1H), 1.89-1.73 (m, 3H), 1.70-1.61 (m, 1H), 1.19 (t, J=7.1 Hz, 3H). LCMS (ESI) m/z calcd for $C_{25}H_{28}BrN_4O_8P$: 622.08. Found: 623.17/625.11 $(M/M+2)^+$.

Preparation of ethyl (S)-6-bromo-4-(2-((phosphonooxy)methyl)-2H-indazole-7-carboxamido)spiro [chromane-2,4'-piperidine]-1'-carboxylate, bis 2-amino-2-(hydroxymethyl)-1,3-propanediol salt

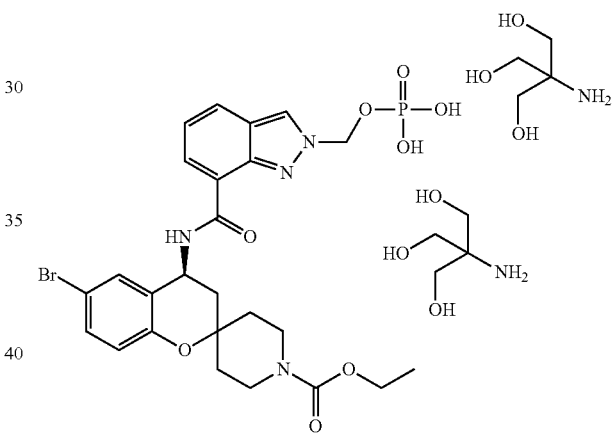

To a suspension of ethyl (S)-6-bromo-4-(2-((phosphonooxy)methyl)-2H-indazole-7-carboxamido)spiro[chromane-2,4'-piperidine]-1'-carboxylate (250 mg, 0.40 mmol) in water (2.0 mL) was added a solution of tris(hydroxymethyl)aminomethane (97 mg, 0.80 mmol) in water (2.0 mL) to provide a clear solution. After 30 min the mixture was diluted with acetonitrile (8 mL) until cloudy and seeded some crystalline. Stirring at ambient temperature continued for 4 h. The solid was filtered, washed with MeCN/water (9:1) and dried in vac. to provide the title compound (300 mg, 86% yield) as a white solid. $^1$H NMR (400 MHz, DMSO) δ 9.44 (d, J=7.8 Hz, 1H), 8.82 (s, 1H), 8.08 (d, J=6.8 Hz, 1H), 7.99 (d, J=8.2 Hz, 1H), 7.42 (s, 1H), 7.33 (d, J=8.6 Hz, 1H), 7.23 (t, J=7.6 Hz, 1H), 6.85 (d, J=8.7 Hz, 1H), 6.00-5.87 (m, 2H), 5.48-5.39 (m, 1H), 4.81 (br, 16H), 3.37 (s, 12H), 3.30-3.23 (m, 1H), 3.15-3.05 (m, 1H), 2.38-2.28 (m, 1H), 2.04-1.97 (m, 1H), 1.87-1.71 (m, 3H), 1.68-1.59 (m, 1H), 1.19 (t, J=6.9 Hz, 3H).

Example 51

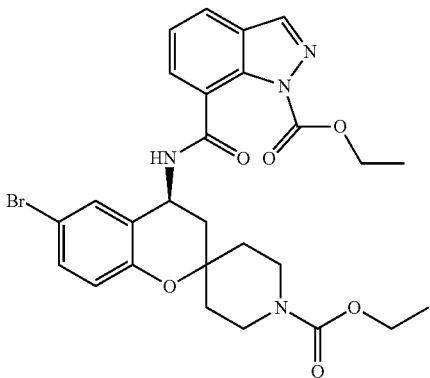 [SMILES: CCOC(=O)N1CCC2(CC1)C[C@H](NC(=O)c1cccc3cnn(C(=O)OCC)c13)c1cc(Br)ccc1O2]

Preparation of ethyl (S)-6-bromo-4-(1-(ethoxycarbonyl)-1H-indazole-7-carboxamido)spiro[chromane-2,4'-piperidine]-1'-carboxylate At 0° C., to a stirred suspension of ethyl (S)-6-bromo-4-(1H-indazole-7-carboxamido) spiro[chromane-2,4'-piperidine]-1'-carboxylate (150 mg, 0.30 mmol) and DIPEA (0.16 mL, 0.90 mmol) in DCM (2 mL) was added ethyl chloroformate (0.045 mL, 0.45 mmol) drop wise. After 20 minutes, the reaction mixture was partitioned between DCM and aq. NaHCO$_3$. The layers were separated and the organic layer was washed with brine, dried over Na$_2$SO$_4$ and concentrated to give the crude product, which was purified by Prep. HPLC (C18, 10-100% MeCN in H$_2$O with 0.5% formic acid) to afford the title compound (47 mg, 27% yield) as a white solid. $^1$H NMR (400 MHz, DMSO) δ 9.41 (d, J=8.3 Hz, 1H), 9.20 (s, 1H), 8.19 (dd, J=6.9, 1.0 Hz, 1H), 8.03 (dd, J=8.6, 0.9 Hz, 1H), 7.44 (d, J=2.0 Hz, 1H), 7.40-7.32 (m, 2H), 6.89 (d, J=8.7 Hz, 1H), 5.48-5.41 (m, 1H), 4.52 (q, J=7.1 Hz, 2H), 4.04 (q, J=7.1 Hz, 2H), 3.86-3.74 (m, 2H), 3.27-3.09 (m, 2H), 2.41-2.35 (m, 1H), 2.02-1.75 (m, 4H), 1.70-1.62 (m, 1H), 1.35 (t, J=7.1 Hz, 3H), 1.18 (t, J=7.1 Hz, 3H). LCMS (ESI) m/z calcd for C$_{27}$H$_{29}$BrN$_4$O$_6$: 584.13. Found: 585.611/587.61 (M/M−2)$^+$.

Example 52

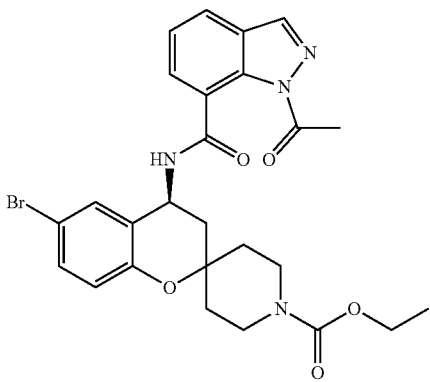 [SMILES: CCOC(=O)N1CCC2(CC1)C[C@H](NC(=O)c1cccc3cnn(C(C)=O)c13)c1cc(Br)ccc1O2]

Preparation of ethyl (S)-4-(1-acetyl-1H-indazole-7-carboxamido)-6-bromospiro [chromane-2,4'-piperidine]-1'-carboxylate At 0° C., to a stirred suspension of ethyl (S)-6-bromo-4-(1H-indazole-7-carboxamido) spiro[chromane-2,4'-piperidine]-1'-carboxylate (150 mg, 0.3 mmol) and DIPEA (0.16 mL, 0.9 mmol) in DCM (2 mL) was added acetyl chloride (0.03 mL, 0.45 mmol) drop wise. After 2 h, the reaction mixture was partitioned between DCM and aq. NaHCO$_3$. The layers were separated and the organic layer was washed with brine, dried over Na$_2$SO$_4$ and concentrated to give the crude product, which was purified by Prep. HPLC (C18, 10-100% MeCN in H$_2$O with 0.5% formic acid) to afford the title compound (56 mg, 34% yield) as a white solid. $^1$H NMR (400 MHz, DMSO) δ 9.21 (s, 1H), 9.18 (d, J=7.9 Hz, 1H), 8.16 (dd, J=6.9, 0.8 Hz, 1H), 8.06-8.01 (m, 1H), 7.51 (d, J=1.9 Hz, 1H), 7.39-7.33 (m, 2H), 6.88 (d, J=8.7 Hz, 1H), 5.47-5.41 (m, 1H), 4.05 (q, J=7.1 Hz, 2H), 3.83-3.75 (m, 2H), 3.30-3.21 (m, 1H), 3.15-3.06 (m, 1H), 2.80 (s, 3H), 2.42-2.34 (m, 1H), 2.00-1.94 (m, 1H), 1.85-1.65 (m, 4H), 1.19 (t, J=7.1 Hz, 3H). LCMS (ESI) m/z calcd for C$_{26}$H$_{27}$BrN$_4$O$_5$: 554.12. Found: 555.14/557.09 (M/M−2)$^+$.

Example 53: 2-amino-2-(hydroxymethyl)propane-1, 3-diol hemi((S)-(7-((6-bromo-1'-(methoxycarbonyl)spiro[chroman-2,4'-piperidin]-4-yl)carbamoyl)-2H-indazol-2-yl)methyl phosphate)

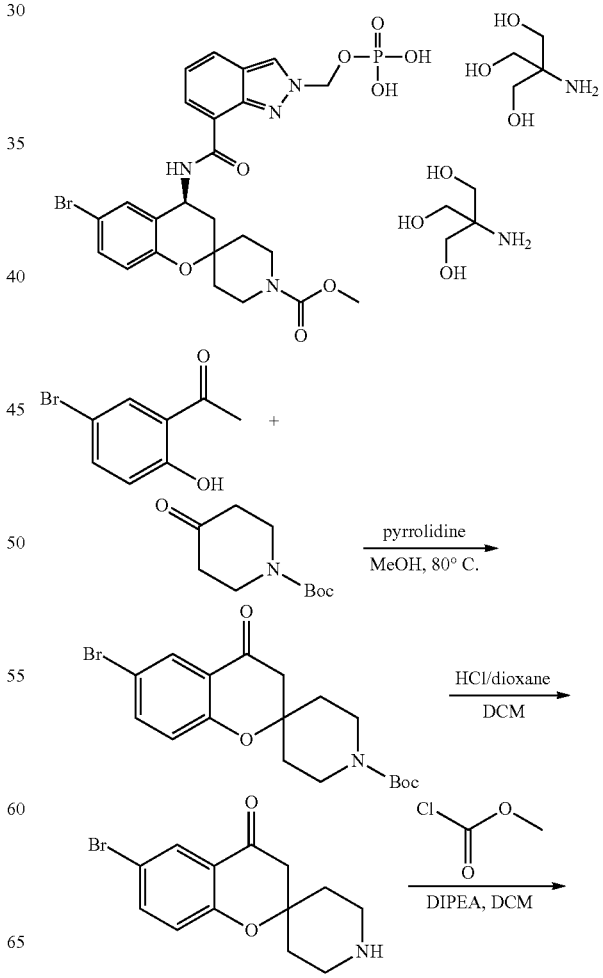

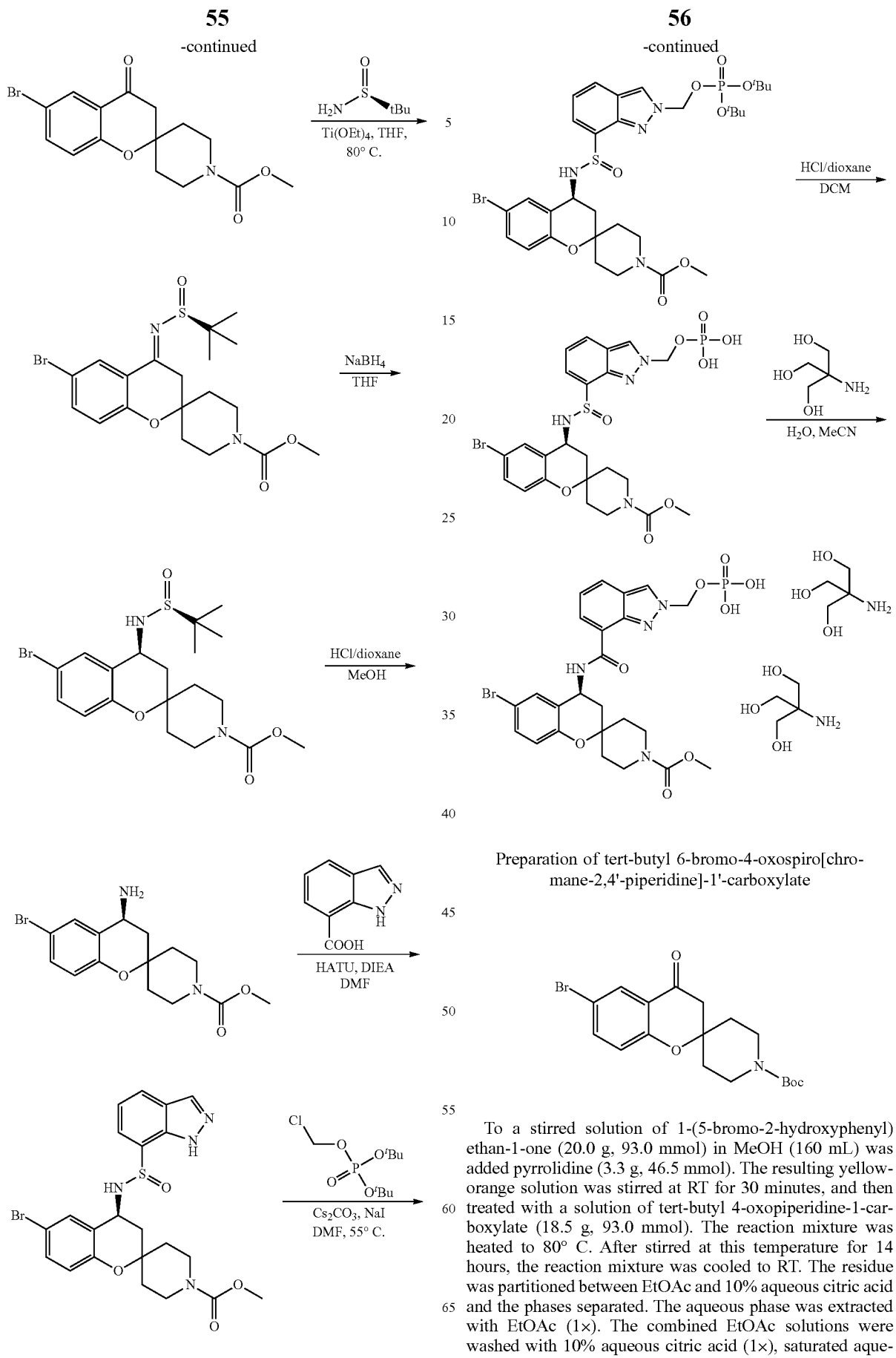

Preparation of tert-butyl 6-bromo-4-oxospiro[chromane-2,4'-piperidine]-1'-carboxylate To a stirred solution of 1-(5-bromo-2-hydroxyphenyl)ethan-1-one (20.0 g, 93.0 mmol) in MeOH (160 mL) was added pyrrolidine (3.3 g, 46.5 mmol). The resulting yellow-orange solution was stirred at RT for 30 minutes, and then treated with a solution of tert-butyl 4-oxopiperidine-1-carboxylate (18.5 g, 93.0 mmol). The reaction mixture was heated to 80° C. After stirred at this temperature for 14 hours, the reaction mixture was cooled to RT. The residue was partitioned between EtOAc and 10% aqueous citric acid and the phases separated. The aqueous phase was extracted with EtOAc (1×). The combined EtOAc solutions were washed with 10% aqueous citric acid (1×), saturated aqueous NaHCO$_3$ (2×), dried over Na$_2$SO$_4$, and concentrated at reduced pressure. The residue was purified by recrystallization in PE/EA to afford the title compound as a light yellow solid (17 g, 46%). LCMS (ESI) m/z calcd for C$_{18}$H$_{22}$BrNO$_4$: 395.07. Found: 296.1/298.1 (M−100/M−98)$^+$.

Preparation of 6-bromospiro[chromane-2,4'-piperidin]-4-one

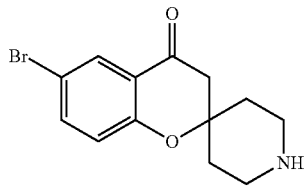 [SMILES: O=C1CC2(CCNCC2)Oc2ccc(Br)cc21]

To a solution of tert-butyl 6-bromo-4-oxospiro[chromane-2,4'-piperidine]-1'-carboxylate (39.1 g, 98.90 mmol) in DCM (240.0 mL) was added 4 M HCl in dioxane (123.6 mL). After stirred at r.t. for 1.5 h, the reaction mixture was concentrated under vacuum to afford the title compound (32.7 g, quantitative yield) as a HCl salt, which was used in the following step directly. LCMS (ESI) m/z calcd for C$_{13}$H$_{14}$BrNO$_2$: 295.02. Found: 296.14/298.14 (M/M+2)$^+$.

Preparation of (S)-isopropyl 6-bromo-4-(1H-indazole-7-carboxamido)spiro [chroman-2,4'-piperidine]-1'-carboxylate

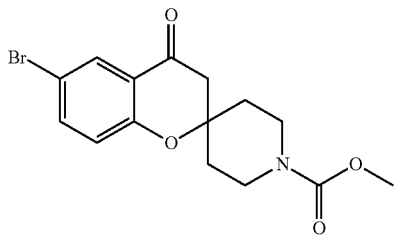

At 0° C., to a stirred suspension of (S)—N-(6-bromospiro[chromane-2,4'-piperidin]-4-yl)-1H-indazole-7-carboxamide dihydrochloride (30.5 g, 92.10 mmol) in DCM (300 mL) was added DIPEA (48.0 mL, 276.2 mmol). The resulting solution was treated with methyl chloroformate (11.0 mL, 138.15 mmol) drop wise. After 60 minutes, the reaction mixture was partitioned between DCM and 10% aqueous citric acid and the phases separated. The aqueous phase was extracted with DCM (1×). The combined EtOAc solutions were washed with 10% aqueous citric acid (1×), saturated aqueous NaHCO$_3$ (2×), dried over Na$_2$SO$_4$, and concentrated at reduced pressure. The residue was purified by recrystallization in PE/EA to afford the title compound as a light yellow solid (28.8 g, 89% yield). LCMS (ESI) m/z calcd for C$_{15}$H$_{16}$BrNO$_4$: 353.03. Found: 354.13/356.13 (M/M−2)$^+$.

Preparation of methyl 6-bromo-4-oxospiro[chromane-2,4'-piperidine]-1'-carboxylate

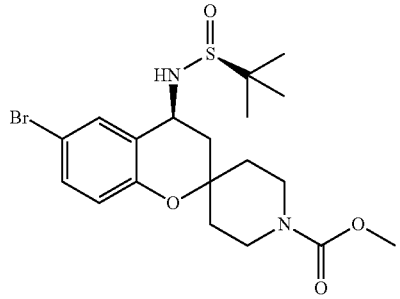 [SMILES: COC(=O)N1CCC2(CC1)C[C@H](N[S@@](=O)C(C)(C)C)c1cc(Br)ccc1O2]

To a stirred solution of methyl 6-bromo-4-oxospiro[chromane-2,4'-piperidine]-1'-carboxylate (28.80 g, 81.30 mmol) and (S)-2-methylpropane-2-sulfinamide (19.7 g, 162.6 mmol) in anhydrous THF (300 mL) was added Ti(OEt)$_4$ (51.0 mL, 243.9 mmol). The resulting mixture was heated at 80° C. under a nitrogen atmosphere. After 20 hours, the solution was cooled to RT and then to −35° C. The solution was treated with NaBH$_4$ (15.4 g, 406.5 mmol). After stirring at −35° C. for 30 minutes, the mixture was allowed to warm to −20° C. and stirred at this temperature overnight. LCMS indicated complete conversion of the imine intermediate to the desired amine product as a 96:4 mixture of diastereomers. The cloudy solution was cooled to 0° C. and quenched by slow addition of MeOH until gas evolution ceased. The resulting mixture was treated with saturated aqueous brine to afford a thick, light yellow suspension. The solid was removed by filtration through a medium fritted funnel. The filtrate was washed with saturated brine (1×), dried over Na$_2$SO$_4$, and concentrated at reduced pressure. The residue was subjected to flash chromatography (silica gel, 20-100% EtOAc/DCM, gradient elution) to afford the title compound as a white solid (28.7 g, 77% yield). LCMS (ESI) m/z calcd for C$_{19}$H$_{27}$BrN$_2$O$_4$S: 458.09. Found: 459.23/461.23 (M/M+2)+.

Preparation of (S)-methyl 4-amino-6-bromospiro[chroman-2,4'-piperidine]-1'-carboxylate hydrochloride

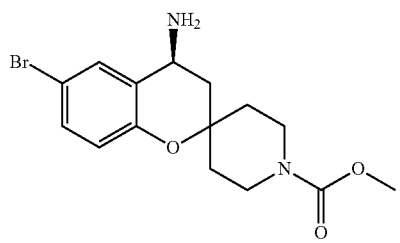 [SMILES: COC(=O)N1CCC2(CC1)C[C@H](N)c1cc(Br)ccc1O2]

At 0° C., to a stirred suspension of methyl (S)-6-bromo-4-(((S)-tert-butylsulfinyl)amino) spiro[chromane-2,4'-piperidine]-1'-carboxylate (26.9 g, 58.3 mmol) in anhydrous MeOH (200 mL) was added 4N HCl/dioxane (58.3 mL, 233.2 mmol) drop wise. The solution was then allowed to warm to RT. After 3 hours, the solution was concentrated to dryness at reduced pressure. The residue was redissolved in MeOH and concentrated again to dryness to afford the title compound as a tan solid (20.8 g, quantitative yield), which was used in the following step without further purification. LCMS (ESI) m/z calcd for $C_{15}H_{19}BrN_2O_3$: 354.06. Found: 355.61/357.32 $(M/M-2)^+$.

Preparation of methyl (S)-6-bromo-4-(1H-indazole-7-carboxamido)spiro[chromane-2,4'-piperidine]-1'-carboxylate

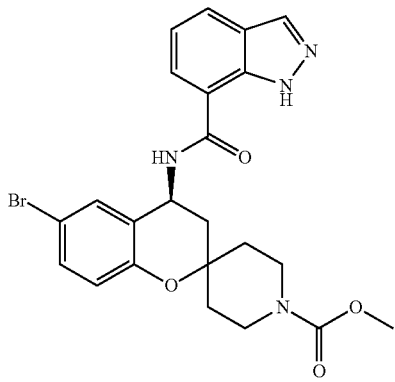 [SMILES: COC(=O)N1CCC2(CC1)C[C@H](NC(=O)c1cccc3cn[nH]c13)c1cc(Br)ccc1O2]

To a stirred solution of (S)-methyl 4-amino-6-bromospiro [chroman-2,4'-piperidine]-1'-carboxylate hydrochloride (15.0 g, 38.5 mmol) and 1H-indole-7-carboxylic acid (5.6 g, 35 mmol) in DMF (150 mL) was added DIEA (18.3 mL, 105 mmol) followed by HATU (14.6 g, 38.5 mmol). The resulting solution was stirred at RT. After 18 hours the solution was partitioned between EtOAc and 10% aqueous citric acid. After separating the phases, the EtOAc phase was washed with 10% aqueous citric acid (1×), saturated aqueous NaHCO$_3$ (2×), dried over Na$_2$SO$_4$ and concentrated to dryness at reduced pressure. The residue was subjected to flash chromatography (silica gel, 20-100% EtOAc/hexanes) to afford the title compound as a white solid (10.1 g, 53% yield). $^1$H NMR (400 MHz, CDCl$_3$) δ 8.16 (s, 1H), 7.98 (d, J=8.0 Hz, 1H), 7.60 (d, J=7.3 Hz, 1H), 7.44 (d, J=1.7 Hz, 1H), 7.31 (dd, J=8.7, 2.3 Hz, 1H), 7.22 (t, J=7.7 Hz, 1H), 6.80 (d, J=8.7 Hz, 1H), 6.61 (d, J=8.4 Hz, 1H), 5.65-5.57 (m, 1H), 4.05-3.83 (m, 2H), 3.70 (s, 3H), 3.42-3.31 (m, 1H), 3.18-3.08 (m, 1H), 2.39-2.30 (m, 1H), 1.97-1.82 (m, 3H), 1.75-1.60 (m, 2H). Proton of nitrogen in the indazole ring was not observed. LCMS (ESI) m/z calcd for $C_{23}H_{23}BrN_4O_4$: 498.09. Found: 499.28/501.28 $(M/M+2)^+$.

Preparation of methyl (S)-6-bromo-4-(2-(((di-tert-butoxyphosphoryl)oxy)methyl)-2H-indazole-7-carboxamido)spiro[chromane-2,4'-piperidine]-1'-carboxylate

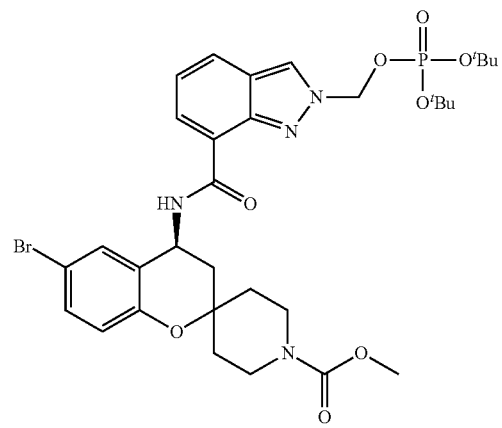 [SMILES: COC(=O)N1CCC2(CC1)C[C@H](NC(=O)c1cccc3cn(COP(=O)(OC(C)(C)C)OC(C)(C)C)nc13)c1cc(Br)ccc1O2]

To a stirred suspension of (S)-ethyl 6-bromo-4-(1H-indazole-7-carboxamido)spiro [chroman-2,4'-piperidine]-1'-carboxylate (10 g, 20.0 mmol) and Cs$_2$CO$_3$ (19.6 g, 60.0 mmol) in DMF (80 mL) was added di-tert-butyl (chloromethyl) phosphate (7.8 g, 30 mmol), NaI (3.3 g, 22 mmol). After stirred at 55° C. for 5 hours, the resulting mixture was partitioned between EtOAc and water. The organic layer was separated and washed with saturated aqueous NaCl (2×), dried over Na$_2$SO$_4$ and concentrated to dryness at reduced pressure to afford the title compound as a yellow gum (14.7 g, quantitative yield), which was used in the following step without purification. LCMS (ESI) m/z calcd for $C_{32}H_{42}BrN_4O_8P$: 720.19. Found: 721.41/723.56 $(M/M-2)^+$.

Preparation of methyl (S)-6-bromo-4-(2-((phosphonooxy)methyl)-2H-indazole-7-carboxamido)spiro [chromane-2,4'-piperidine]-1'-carboxylate

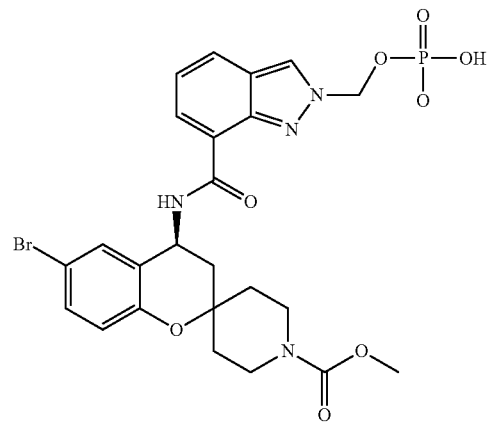 [SMILES: COC(=O)N1CCC2(CC1)C[C@H](NC(=O)c1cccc3cn(COP(=O)(O)O)nc13)c1cc(Br)ccc1O2]

To a stirred solution of methyl (S)-6-bromo-4-(2-(((di-tert-butoxyphosphoryl)oxy)methyl)-2H-indazole-7-carboxamido)spiro[chromane-2,4'-piperidine]-1'-carboxylate (405 mg, 0.55 mmol) in DCM (4 mL) was added 4 M HCl in dioxane (4.1 mL, 16.5 mmol). After stirred at 25° C. for 3 hours, the resulting mixture was concentrated at reduced pressure to afford a residue, which was dried under high vacuum. The resulting residue was purified by recrystallization in MCN/water (9:1) to afford the title compound as a white solid (233 mg, 68% yield). $^1$H NMR (400 MHz, DMSO) δ 9.40 (d, J=8.2 Hz, 1H), 8.76 (s, 1H), 8.17-7.99 (m, 2H), 7.42 (s, 1H), 7.38-7.23 (m, 2H), 6.86 (d, J=8.7 Hz, 1H), 6.20-6.01 (m, 2H), 5.52-5.40 (m, 1H), 3.86-3.75 (m, 2H), 3.61 (s, 3H), 3.40-3.27 (m, 3H), 3.14-3.09 (m, 1H), 2.36-2.29 (m, 1H), 2.07-1.93 (m, 2H), 1.84-1.76 (m, 2H), 1.70-1.61 (m, 1H). LCMS (ESI) m/z calcd for $C_{24}H_{26}BrN_4O_8P$: 608.07. Found: 607.68/609.67 (M/M−2)$^+$.

Preparation of methyl (S)-6-bromo-4-(2-((phosphonooxy)methyl)-2H-indazole-7-carboxamido)spiro[chromane-2,4'-piperidine]-1'-carboxylate, bis 2-amino-2-(hydroxymethyl)-1,3-propanediol salt

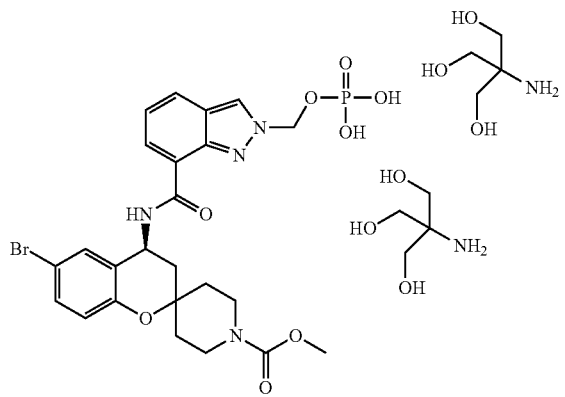 [SMILES: COC(=O)N1CCC2(CC1)C[C@H](NC(=O)c1cccc3cn(COP(=O)(O)O)nc13)c1cc(Br)ccc1O2 ; NC(CO)(CO)CO ; NC(CO)(CO)CO]

To a suspension of methyl (S)-6-bromo-4-(2-((phosphonooxy)methyl)-2H-indazole-7-carboxamido)spiro[chromane-2,4'-piperidine]-1'-carboxylate (10.7 g, 17.6 mmol) in water (30.0 mL) was added a solution of tris(hydroxymethyl)aminomethane (4.5 g, 37.1 mmol) in water (20.0 mL) to provide a clear solution. After 60 min the mixture was diluted with acetonitrile (300 mL) until cloudy and seeded some crystalline. Stirring at ambient temperature continued for 4 h. The solid was collected by filtration, washed with MeCN/water (9:1) and dried in vac. to provide the title compound (300 mg, 86% yield) as a white solid. $^1$H NMR (400 MHz, DMSO) δ 9.44 (d, J=8.2 Hz, 1H), 8.80 (s, 1H), 8.08 (dd, J=7.0, 0.9 Hz, 1H), 7.99 (dd, J=8.4, 0.9 Hz, 1H), 7.43 (d, J=1.8 Hz, 1H), 7.33 (dd, J=8.7, 2.4 Hz, 1H), 7.26-7.19 (m, 1H), 6.85 (d, J=8.7 Hz, 1H), 5.99-5.87 (m, 2H), 5.48-4.61 (m, 13H), 3.85-3.72 (m, 2H), 3.61 (s, 3H), 3.36 (s, 12H), 3.32-3.26 (m, 1H), 3.15-3.05 (m, 1H), 2.36-2.29 (m, 1H), 2.03-1.97 (m, 1H), 1.86-1.72 (m, 3H), 1.68-1.60 (m, 1H).

Example 54

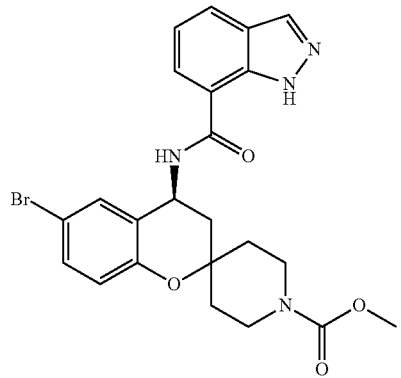 [SMILES: COC(=O)N1CCC2(CC1)C[C@H](NC(=O)c1cccc3cn[nH]c13)c1cc(Br)ccc1O2]

Preparation of methyl (S)-4-(1H-indazole-7-carboxamido)spiro[chromane-2,4'-piperidine]-1'-carboxylate To a solution of methyl (S)-6-bromo-4-(1H-indazole-7-carboxamido)spiro[chromane-2,4'-piperidine]-1'-carboxylate (6.5 g, 13.0 mmol) in EtOH (60 mL) was added 10% Pd/C (4.1 g) and this was stirred at 55° C. under hydrogen atmosphere for 16 hr. The reaction mixture was filtered through celite and the filtrate was concentrated and subjected to flash chromatography (silica gel, 0-10% MeOH/DCM) to afford the title compound (2.5 g, 46% yield) as a white solid. $^1$H NMR (400 MHz, DMSO) δ 13.15 (s, 1H), 9.01 (d, J=8.5 Hz, 1H), 8.17 (s, 1H), 7.97 (t, J=7.1 Hz, 2H), 7.30-7.10 (m, 3H), 6.96-6.80 (m, 2H), 5.54-5.43 (m, 1H), 3.89-3.72 (m, 2H), 3.61 (s, 3H), 3.39 (s, 1H), 3.15-3.03 (m, 1H), 2.25-2.15 (m, 1H), 2.07-1.98 (m, 1H), 1.89-1.69 (m, 3H), 1.67-1.58 (m, 1H). LCMS (ESI) m/z calcd for $C_{23}H_{24}N_4O_4$: 420.18. Found: 421.35 (M+1)$^+$.

Example 55: 2-amino-2-(hydroxymethyl)propane-1,3-diol hemi((S)-(7-((1'-(ethoxycarbonyl)spiro[chroman-2,4'-piperidin]-4-yl)carbamoyl)-2H-indazol-2-yl)methyl phosphate)

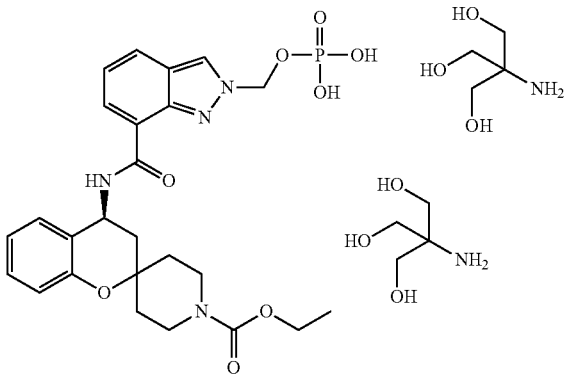

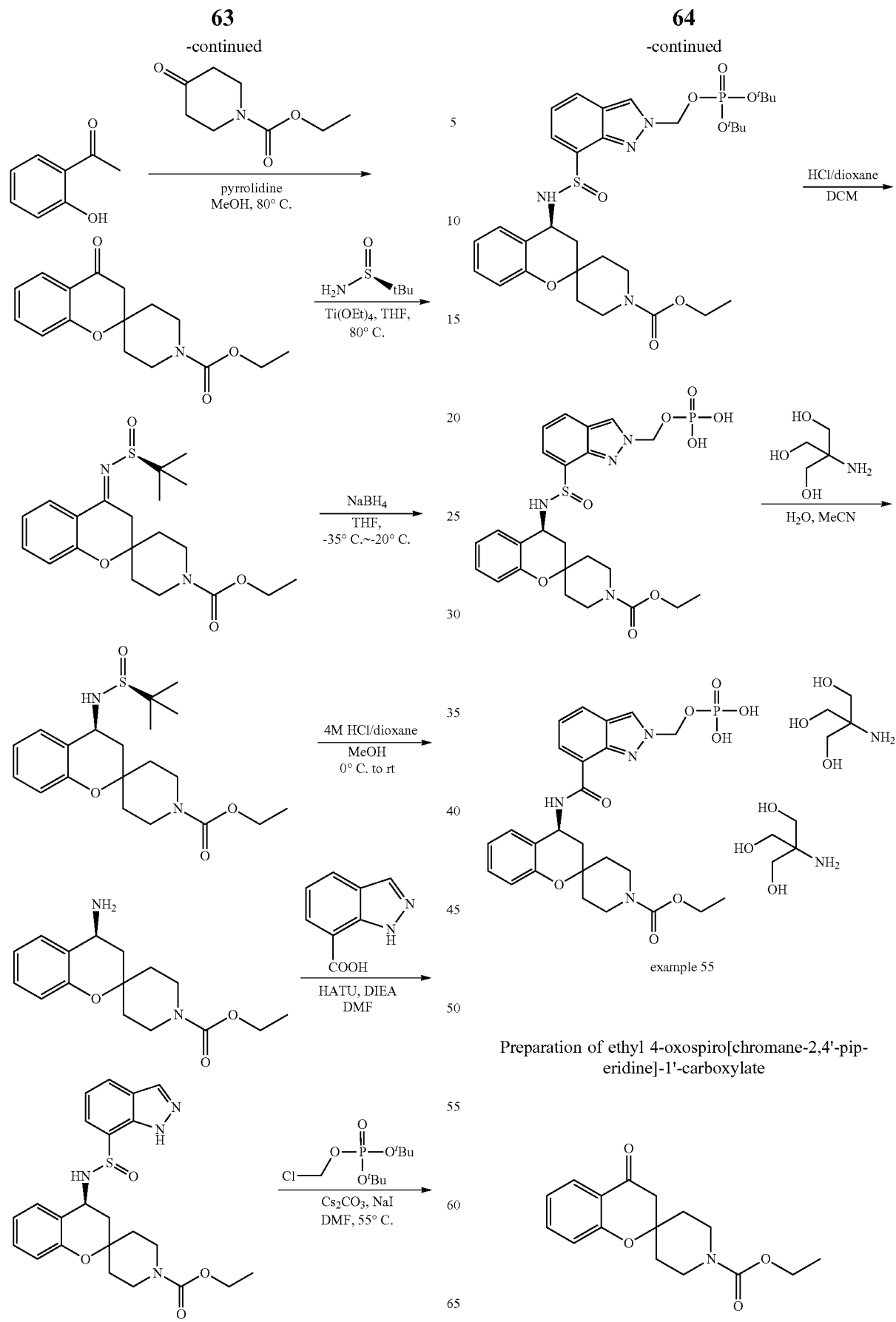
Preparation of ethyl 4-oxospiro[chromane-2,4'-piperidine]-1'-carboxylate To a stirred solution of 1-(2-hydroxyphenyl)ethan-1-one (20.00 g, 146.9 mmol) in MeOH (200 mL) was added pyrrolidine (6 mL, 73.45 mmol). The resulting yellow-orange solution was stirred at RT for 30 minutes, and then treated with a solution of ethyl 4-oxopiperidine-1-carboxylate (25.0 g, 146.9 mmol). After stirred at 80° C. for 14 hours, the reaction mixture was cooled to RT during which time a solid crystallized. The mixture was cooled in an ice water bath for 30 minutes, and the solid collected by vacuum filtration, washing with two portions of ice cold MeOH. Drying in vacuo afforded the title compound as a light yellow solid (33.3 g, 73%). LCMS (ESI) m/z calcd for $C_{16}H_{19}NO_4$: 289.13. Found: 290.27 $(M+1)^+$.

Preparation of ethyl (S)-4-(((S)-tert-butylsulfinyl)amino)spiro[chromane-2,4'-piperidine]-1'-carboxylate

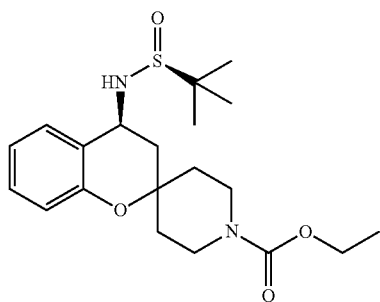 [SMILES: CCOC(=O)N1CCC2(CC1)C[C@H](N[S@@](=O)C(C)(C)C)c1ccccc1O2]

To a stirred solution of ethyl 4-oxospiro[chromane-2,4'-piperidine]-1'-carboxylate (33.3 g, 115.1 mmol) and (S)-2-methylpropane-2-sulfinamide (21.2 g, 172.6 mmol) in anhydrous THF (300 mL) was added Ti(OEt)$_4$ (78.7 g, 345.3 mmol). The resulting mixture was heated at 80° C. under a nitrogen atmosphere. After 20 hours, the solution was cooled to −35° C. and treated with NaBH$_4$ (21.7 g, 575.5 mmol).). After stirred at −35° C. for 30 minutes the mixture was allowed to warm to −20° C. and stirred overnight. LCMS indicated complete conversion of the imine intermediate to the desired amine product as a 92:8 mixture of diastereomers. The cloudy solution was cooled to 0° C. and quenched by slow addition of MeOH until gas evolution ceased. The resulting mixture was treated with saturated aqueous brine to afford a thick, light yellow suspension. The solid was removed by filtration. The filter cake was washed with EtOAc (3×). The filtrate was washed with saturated brine (1×), dried over Na$_2$SO$_4$, and concentrated at reduced pressure. The residue was subjected to flash chromatography (silica gel, 20-100% EtOAc/DCM, gradient elution) to afford the title compound (25.6 g, 56.0% yield) as a white solid. LCMS (ESI) m/z calcd for $C_{20}H_{30}N_2O_4S$: 394.19. Found: 395.35 $(M+1)^+$.

Preparation of ethyl (S)-4-aminospiro[chromane-2,4'-piperidine]-1'-carboxylate

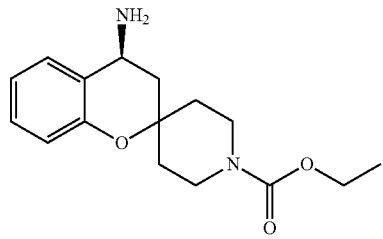 [SMILES: CCOC(=O)N1CCC2(CC1)C[C@H](N)c1ccccc1O2]

To a stirred suspension of ethyl (S)-4-(((S)-tert-butylsulfinyl)amino)spiro[chromane-2,4'-piperidine]-1'-carboxylate (30.0 g, 76 mmol) in anhydrous MeOH (200 mL) at 0° C. was added 4N HCl/dioxane (19 mL, 76 mmol) drop wise. The solution was then allowed to warm to RT. The solution was concentrated to dryness at reduced pressure. The residue was redissolved in MeOH and again concentrated to dryness to afford the title compound as a tan solid in quantitative yield. This material was used without further purification. LCMS (ESI) m/z calcd for $C_{16}H_{22}N_2O_3$: 290.16. Found: 291.36 $(M-1)^+$.

Preparation of ethyl (S)-4-(1H-indazole-7-carboxamido)spiro[chromane-2,4'-piperidine]-1'-carboxylate

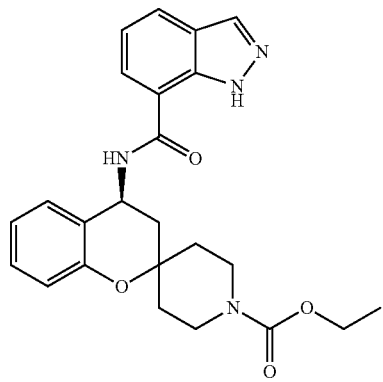 [SMILES: CCOC(=O)N1CCC2(CC1)C[C@H](NC(=O)c1cccc3cn[nH]c13)c1ccccc1O2]

To a stirred solution of ethyl (S)-4-aminospiro[chromane-2,4'-piperidine]-1'-carboxylate (28 g, 96.43 mmol) and 1H-indole-7-carboxylic acid (15.6 g, 96.43 mmol) in DMF (300 mL) was added DIEA (50 mL, 289.29 mmol), followed by HATU (55 g, 144.65 mmol). The resulting solution was stirred at RT. After 8 hours the solution was partitioned between EtOAc and 10% aqueous citric acid. After separating the phases, the EtOAc phase was washed with 10% aqueous citric acid (1×), saturated aqueous NaHCO$_3$ (2×), dried over Na$_2$SO$_4$ and concentrated to dryness at reduced pressure. The residue was subjected to flash chromatography (silica gel, 20-100% EtOAc/hexanes) to afford the title compound as a white solid (23 g, 55% yield). LCMS (ESI) m/z calcd for $C_{24}H_{26}N_4O_4$: 434.20. Found: 435.32 $(M+1)^+$.

Preparation of ethyl (S)-4-(2-(((di-tert-butoxyphosphoryl)oxy)methyl)-2H-indazole-7-carboxamido)spiro[chromane-2,4'-piperidine]-1'-carboxylate

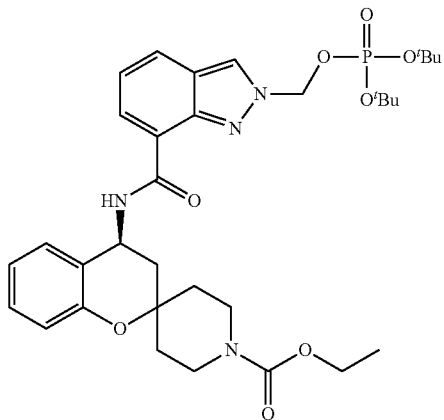 [SMILES: CCOC(=O)N1CCC2(CC1)C[C@H](NC(=O)c1cccc3cn(COP(=O)(OC(C)(C)C)OC(C)(C)C)nc13)c1ccccc1O2]

To a stirred suspension of ethyl (S)-4-(1H-indazole-7-carboxamido)spiro[chromane-2,4'-piperidine]-1'-carboxylate (1.56 g, 3.6 mmol), NaI (593 mg, 3.96 mmol) and Cs$_2$CO$_3$ (3.5 g, 10.8 mmol) in DMF (20 mL) was added di-tert-butyl (chloromethyl) phosphate (1.4 g, 5.4 mmol). After stirred at 55° C. for 5 hours, the resulting mixture was partitioned between EtOAc and water. After separating the layers, the organic layer was washed with saturated aqueous NaCl (2×), dried over Na$_2$SO$_4$ and concentrated to dryness at reduced pressure to afford the title compound as a yellow gum (2.2 g, 94% yield), which was used in the following step without purification. LCMS (ESI) m/z calcd for C$_{33}$H$_{45}$BrN$_4$O$_8$P: 656.30. Found: 657.42 (M+1)+.

Preparation of ethyl (S)-4-(2-((phosphonooxy)methyl)-2H-indazole-7-carboxamido)spiro[chromane-2,4'-piperidine]-1'-carboxylate

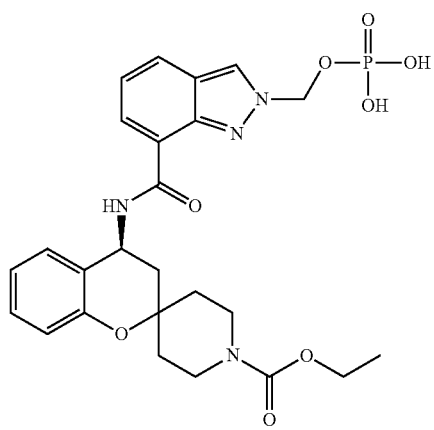 [SMILES: CCOC(=O)N1CCC2(CC1)C[C@H](NC(=O)c1cccc3cn(COP(=O)(O)O)nc13)c1ccccc1O2]

To a stirred solution of ethyl (S)-4-(2-(((di-tert-butoxyphosphoryl)oxy)methyl)-2H-indazole-7-carboxamido)spiro[chromane-2,4'-piperidine]-1'-carboxylate (2.2 g, 3.35 mmol) in dioxane (5 mL) was added 4 M HCl in dioxane (5 mL, 20 mmol). After stirred at 25° C. for 3 hours, the resulting mixture was concentrated at reduced pressure to afford a residue, which was purified by recrystallization in MCN/water (9:1) to afford the title compound as a white solid (654 mg, 36% yield). LCMS (ESI) m/z calcd for C$_{25}$H$_{29}$N$_4$O$_8$P: 544.17. Found: 545.24 (M+1)+.

Preparation of ethyl (S)-4-(2-((phosphonooxy)methyl)-2H-indazole-7-carboxamido)spiro[chromane-2,4'-piperidine]-1'-carboxylate, bis 2-amino-2-(hydroxymethyl)-1,3-propanediol salt

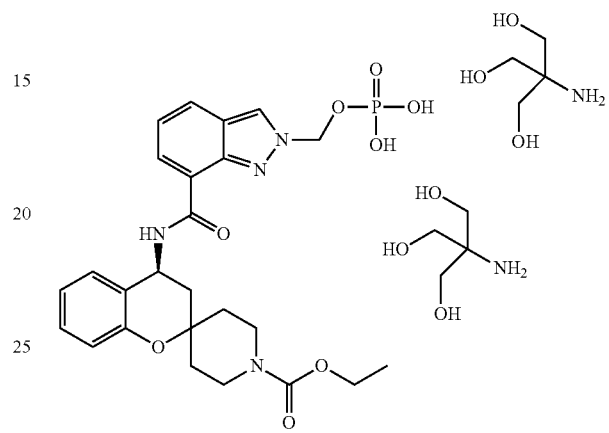

To a suspension of ethyl (S)-4-(2-((phosphonooxy)methyl)-2H-indazole-7-carboxamido)spiro[chromane-2,4'-piperidine]-1'-carboxylate (100 mg, 0.184 mmol) in water (1.0 mL) was added a solution of tris(hydroxymethyl)aminomethane (47 mg, 0.387 mmol) in water (1.5 mL) to provide a clear solution. After 30 min the mixture was diluted with acetonitrile (10 mL) until cloudy and seeded some crystalline. Stirring at ambient temperature was continued for 2 h. The solid was filtered, washed with MeCN/water (9:1) and dried in vac. to provide the title compound (120 mg, 85% yield) as a white solid. $^1$H NMR (400 MHz, DMSO) δ 9.40 (d, J=8.3 Hz, 1H), 8.79 (s, 1H), 8.09 (d, J=6.9 Hz, 1H), 7.97 (d, J=8.3 Hz, 1H), 7.29 (d, J=7.5 Hz, 1H), 7.25-7.12 (m, 2H), 6.92-6.82 (m, 2H), 5.89 (d, J=11.3 Hz, 2H), 5.50-5.43 (m, 1H), 4.75 (br, 12H), 4.05 (q, J=7.0 Hz, 2H), 3.80 (t, J=15.5 Hz, 2H), 3.37 (s, 12H), 3.32-3.23 (m, 1H), 3.18-3.08 (m, 1H), 2.37-2.29 (m, 1H), 2.00-1.92 (m, 1H), 1.85-1.58 (m, 4H), 1.19 (t, J=7.1 Hz, 3H).

Example 56: 2-amino-2-(hydroxymethyl)propane-1,3-diol hemi((S)-(7-((1-phosphate)

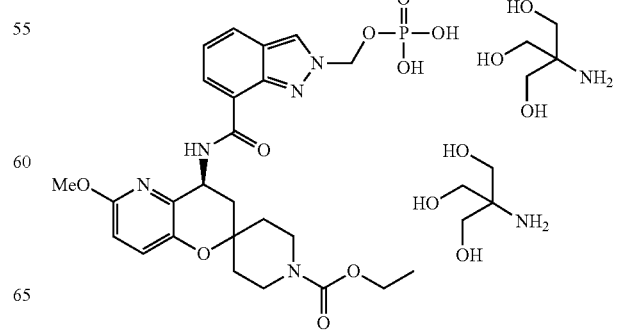

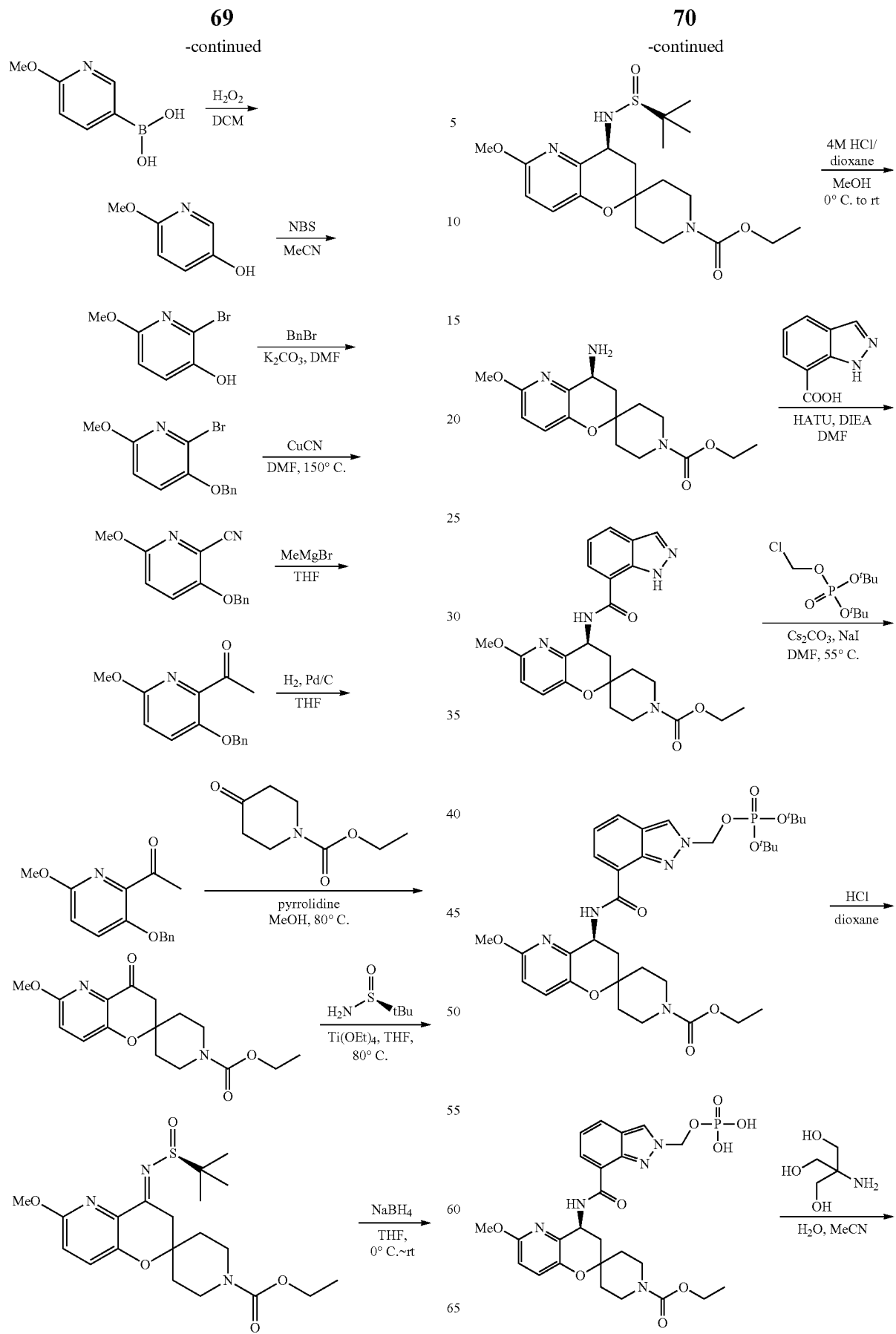

-continued

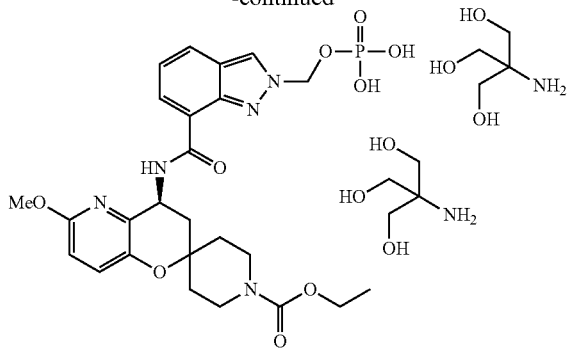

Preparation of 6-methoxypyridin-3-ol

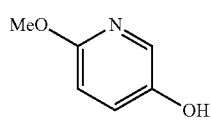

To a solution of (6-methoxypyridin-3-yl)boronic acid (25 g, 163 mmol) in DCM (300 mL) was added hydroperoxide at room temperature drop wise and the mixture was stirred for 4 hr. The resulting mixture was quenched with solid $Na_2SO_3$ and washed with water, brine, dried over $Na_2SO_4$. The resulting solution was concentrated to give the crude product which was purified by flash chromatography (silica gel, 0-10% EtOAc in PE) to afford the title compound (18 g, 88% yield). LCMS (ESI) m/z calcd for $C_6H_7NO_2$: 125.05. Found: 126.14 $(M+1)^+$.

Preparation of 2-bromo-6-methoxypyridin-3-ol

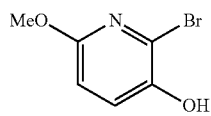

To a stirring solution of 6-methoxypyridin-3-ol (17 g, 136 mmol) in Acetonitrile (170 mL) and water (25 mL) was added NBS (26.6 g, 149 mmol) at 0° C., then this was stirred at 60° C. overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-50% EtOAc in PE) to afford the title compound (22 g, 79% yield). LCMS (ESI) m/z calcd for $C_6H_6BrNO_2$: 202.96. Found: 204.09/206.07 $(M/M-2)^+$.

Preparation of 3-(benzyloxy)-2-bromo-6-methoxypyridine

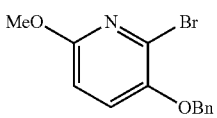

To a stirring suspension of 2-bromo-6-methoxypyridin-3-ol (22 g, 108 mmol) and $K_2CO_3$ (44 g, 324 mmol) in DMF (300 mL) was added BnBr (24 g, 140 mmol) and this was stirred at 40° C. overnight. The resulting mixture was partitioned between EtOAc and $H_2O$. The layers were separated and the organic layer was washed with brine, dried over $Na_2SO_4$. The resulting solution was concentrated to give the crude product which was purified by flash chromatography (silica gel, 0-30% EtOAc in PE) to afford the title compound (33 g, 100% yield). LCMS (ESI) m/z calcd for $C_{13}H_{12}BrNO_2$: 293.01. Found: 294.09/296.08 $(M/M-2)^+$.

Preparation of 3-(benzyloxy)-6-methoxypicolinonitrile

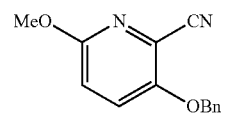

To a stirring solution of 3-(benzyloxy)-2-bromo-6-methoxypyridine (33 g, 113 mmol) in DMF (500 mL) was added CuCN (40.5 g, 452 mmol), and this was stirred at 150° C. for 6 hr. The solid was removed by filtration and the filtrate was partitioned between EtOAc and $H_2O$. The layers were separated and the organic layer was washed with brine, dried over $Na_2SO_4$. The resulting solution was concentrated to give the crude product which was purified by flash chromatography (silica gel, 0-30% EtOAc in PE) to afford the title compound (21 g, 77% yield). LCMS (ESI) m/z calcd for $C_{14}H_{12}N_2O_2$: 240.09. Found: 241.26 $(M+1)^+$.

Preparation of 1-(3-(benzyloxy)-6-methoxypyridin-2-yl)ethanone

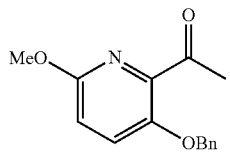 [SMILES: COc1ccc(OCc2ccccc2)c(C(C)=O)n1]

To a stirring solution of 3-(benzyloxy)-6-methoxypicolinonitrile (20 g, 83.3 mmol) in THF (200 mL) was added methylmagnesium bromide (139 mL, 417 mmol) at 0° C. and this was allowed to stir at room temperature for 16 hr. The reaction mixture was quenched with 1N HCl (300 mL) and stirred for another 1 h. Then it was basified with 2M sodium hydroxide solution and extracted with EtOAc (2×200 mL). The layers were separated and the organic layer was washed with brine, dried over $Na_2SO_4$. The resulting solution was concentrated to give the crude product which was purified by flash chromatography (silica gel, 0-30% EtOAc in PE) to afford the title compound (12.6 g, 59% yield). LCMS (ESI) m/z calcd for $C_{15}H_{15}NO_3$: 257.11. Found: 258.24 $(M+1)^+$.

Preparation of 1-(3-hydroxy-6-methoxypyridin-2-yl)ethanone

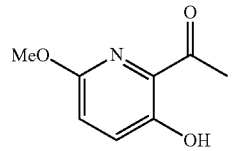

To a solution of 1-(3-(benzyloxy)-6-methoxypyridin-2-yl)ethanone (12 g, 46.7 mmol) in THF (200 mL) was added 10% Pd/C (6 g) at room temperature and this was stirred under hydrogen atmosphere for 16 hr. The reaction mixture was filtered through celite and the filtrate was concentrated to afford the title compound (7.3 g, 94% yield) which was used directly in the following step. LCMS (ESI) m/z calcd for $C_8H_9NO_3$: 167.06. Found: 168.17 $(M+1)^+$.

Preparation of ethyl 6'-methoxy-4'-oxo-3',4'-dihydrospiro[piperidine-4,2'-pyrano [3,2-b]pyridine]-1-carboxylate

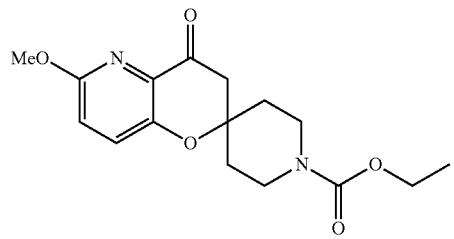 [SMILES: CCOC(=O)N1CCC2(CC1)CC(=O)c1nc(OC)ccc1O2]

To a stirring solution of 1-(3-hydroxy-6-methoxypyridin-2-yl)ethanone (7.3 g, 43.7 mmol) in methanol (150 mL) and was added pyrrolidine (5.3 g, 75.5 mmol) and ethyl 4-oxopiperidine-1-carboxylate (9.73 g, 56.8 mmol) at room temperature and then the reaction mixture was heated to 80° C. and stirred at this temperature for 14 hr. The resulting mixture was partitioned between EtOAc and $H_2O$. The layers were separated and the organic layer was washed with brine, dried over $Na_2SO_4$ and concentrated to give the crude product which was purified by flash chromatography (silica gel, 0-50% EtOAc in PE) to afford the title compound (8.8 g, 63% yield). LCMS (ESI) m/z calcd for $C_{16}H_{20}N_2O_5$: 320.14. Found: 321.24 $(M+1)^+$.

Preparation of ethyl (S)-4'-(((S)-tert-butylsulfinyl)amino)-6'-methoxy-3',4'-dihydrospiro[piperidine-4,2'-pyrano[3,2-b]pyridine]-1-carboxylate

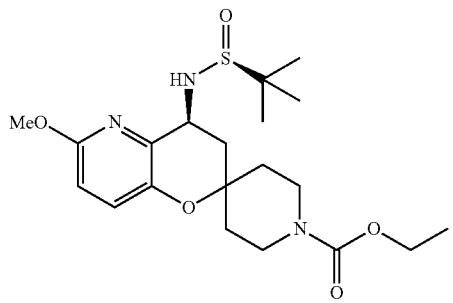 [SMILES: CCOC(=O)N1CCC2(CC1)C[C@H](N[S@@](=O)C(C)(C)C)c1nc(OC)ccc1O2]

To a stirring solution of ethyl 6'-methoxy-4'-oxo-3',4'-dihydrospiro[piperidine-4,2'-pyrano[3,2-b]pyridine]-1-carboxylate (8.8 g, 27.5 mmol) and (S)-2-methylpropane-2-sulfinamide (6.7 g, 55.3 mmol) in THF (200 mL) and was added $Ti(OEt)_4$ (19 g, 83.3 mmol) at room temperature. The resulting mixture was heated at 80° C. under a nitrogen atmosphere. After 20 hours, the solution was cooled to RT and then to −35° C. The solution was treated with $NaBH_4$ (5.2 g, 137.4 mmol). After stirring at −35° C. for 30 minutes, the mixture was allowed to warm to −10° C. and stirred at this temperature overnight. After 18 hours LCMS indicated complete conversion of the imine intermediate to the desired amine product as a 75:25 mixture of diastereomers. The cloudy solution was cooled to 0° C. and quenched by slow addition of MeOH until gas evolution ceased. The resulting mixture was treated with saturated aqueous brine to afford a thick, light yellow suspension. The solid was removed by filtration through a medium fritted funnel. The filtrate was washed with saturated brine (1×), dried over $Na_2SO_4$, and concentrated at reduced pressure to give a residue, which was purified by flash chromatography (silica gel, 20-100% EtOAc/DCM, gradient elution) to afford the title compound as a white solid (4.6 g, 39% yield). LCMS (ESI) m/z calcd for $C_{20}H_{31}N_3O_5S$: 425.20. Found: 426.38 $(M+1)^+$.

Preparation of ethyl (S)-4'-amino-6'-methoxy-3',4'-dihydrospiro[piperidine-4,2'-pyrano[3,2-b]pyridine]-1-carboxylate

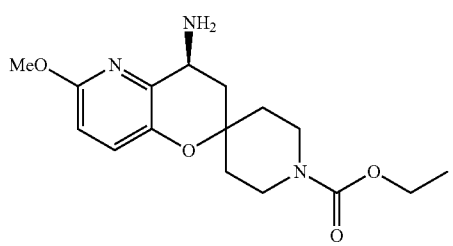 [SMILES: CCOC(=O)N1CCC2(CC1)C[C@H](N)c1nc(OC)ccc1O2]

To a stirring solution of (S)-ethyl 4'-((S)-1,1-dimethylethylsulfinamido)-6'-methoxy-3',4'-dihydrospiro[piperidine-4,2'-pyrano[3,2-b]pyridine]-1-carboxylate (4.6 g, 10.8 mmol) in methanol (50 mL) was added HCl/dioxane (4 mol/L, 5.4 ml, 21.6 mmol) drop wise. The solution was then allowed to warm to RT. After 3 hours, the solution was concentrated to dryness at reduced pressure. The residue was redissolved in MeOH and concentrated again to dryness to afford the title compound as a tan solid (3.5 g, 100% yield), which was used in the following step without further purification. LCMS (ESI) m/z calcd for $C_{16}H_{23}N_3O_4$: 321.17. Found: 322.27 (M+1)$^+$.

Preparation of (S)-ethyl 4'-(1H-indazole-7-carboxamido)-6'-methoxy-3',4'-dihydrospiro[piperidine-4,2'-pyrano[3,2-b]pyridine]-1-carboxylate

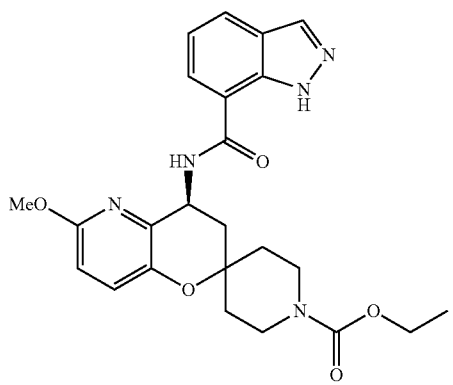 [SMILES: CCOC(=O)N1CCC2(CC1)C[C@H](NC(=O)c1cccc3cn[nH]c13)c1nc(OC)ccc1O2]

To a stirring solution of (S)-ethyl 4'-amino-6'-methoxy-3',4'-dihydrospiro[piperidine-4,2'-pyrano[3,2-b]pyridine]-1-carboxylate (4.5 g, 12.6 mmol) and 1H-indazole-7-carboxylic acid (2.17 g, 13.4 mmol) in DMF (100 mL) and was added DIPEA (8.8 ml, 50.6 mmol), followed by portion wise addition of HATU (5.6 g, 14.7 mmol) and the resulting mixture was stirred at room temperature for 2 h. Then the mixture was partitioned between EtOAc and saturated aq. NaHCO$_3$. The layers were separated and the organic layer was washed with brine, dried over Na$_2$SO$_4$ and concentrated to give the crude product, which was purified by flash chromatography (silica gel, 0-60% EtOAc in PE) to afford the title compound (5 g, 85% yield). $^1$H NMR (400 MHz, DMSO) δ 13.10 (s, 1H), 8.86 (s, 1H), 8.16 (S, 1H), 7.99-7.89 (m, 2H), 7.28 (d, J=8.8 Hz, 1H), 7.19 (t, J=7.6 Hz, 1H), 6.69 (d, J=8.7 Hz, 1H), 5.38-5.28 (m, 1H), 4.05 (q, J=7.1 Hz, 2H), 3.85-3.73 (m, 2H), 3.64 (s, 3H), 3.30-3.21 (m, 1H), 3.18-3.07 (m, 1H), 2.35-2.25 (m, 1H), 2.13-2.03 (m, 1H), 1.91-1.79 (m, 2H), 1.77-1.60 (m, 2H), 1.19 (t, J=7.1 Hz, 3H). LCMS (ESI) m/z calcd for $C_{24}H_{27}N_5O_5$: 465.20. Found: 466.36 (M+1)$^+$.

Preparation of (S)-ethyl 4'-(2-((di-tert-butoxyphosphoryloxy)methyl)-2H-indazole-7-carboxamido)-6'-methoxy-3',4'-dihydrospiro[piperidine-4,2'-pyrano[3,2-b]pyridine]-1-carboxylate

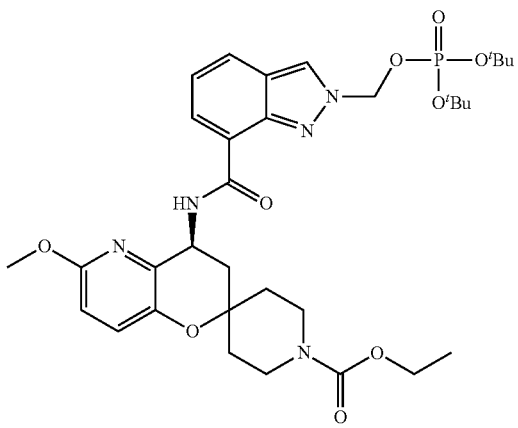 [SMILES: CCOC(=O)N1CCC2(CC1)C[C@H](NC(=O)c1cccc3cn(COP(=O)(OC(C)(C)C)OC(C)(C)C)nc13)c1nc(OC)ccc1O2]

To a stirring solution of (S)-ethyl 4'-(1H-indazole-7-carboxamido)-6'-methoxy-3',4'-dihydrospiro[piperidine-4,2'-pyrano[3,2-b]pyridine]-1-carboxylate (800 mg, 1.72 mmol) in DMF (15 mL) and was added di-tert-butyl chloromethyl phosphate (667 mg, 2.58 mmol), Cs$_2$CO$_3$ (1.68 g, 5.16 mmol) and NaI (284 mg, 1.89 mmol). After stirred at 55° C. for 5 hours, the resulting mixture was partitioned between EtOAc and water. The organic layer was separated and washed with saturated aqueous NaCl (2×), dried over Na$_2$SO$_4$ and concentrated to dryness at reduced pressure to afford the title compound as a yellow gum (1.2 g, 100% yield). LCMS (ESI) m/z calcd for $C_{33}H_{46}N_5O_9P$: 687.30. Found: 688.30 (M+1)$^+$.

Preparation of ethyl (S)-6'-methoxy-4'-(2-((phosphonooxy)methyl)-2H-indazole-7-carboxamido)-3',4'-dihydrospiro[piperidine-4,2'-pyrano[3,2-b]pyridine]-1-carboxylate

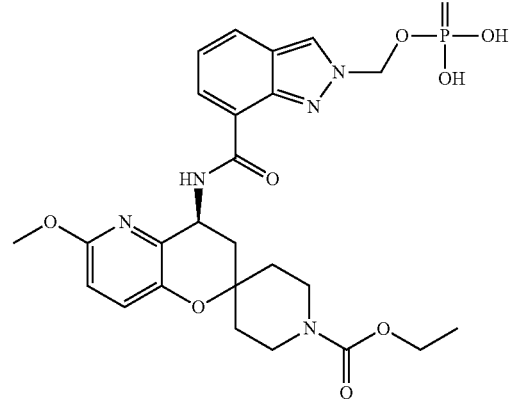

To a stirring solution of (S)-ethyl 4'-(2-((di-tert-butoxyphosphoryloxy)methyl)-2H-indazole-7-carboxamido)-6'-methoxy-3',4'-dihydrospiro[piperidine-4,2'-pyrano[3,2-b]pyridine]-1-carboxylate (1.2 g, 1.75 mmol) in DCM (20 mL)

was added 4 M HCl/dioxane (4.4 ml, 17.4 mmol) at room temperature and stirred for 1 hr. The reaction mixture was concentrated to give the crude product which was purified by Glison (C18, 20-100% MeCN in H$_2$O) to afford the title compound (450 mg, 45% yield). $^1$H NMR (400 MHz, DMSO) δ 9.49 (d, J=6.0 Hz, 1H), 8.73 (s, 1H), 8.12 (dd, J=7.0, 0.8 Hz, 1H), 8.03 (d, J=8.4 Hz, 1H), 7.33-7.23 (m, 2H), 6.73 (d, J=8.8 Hz, 1H), 6.11-6.00 (m, 2H), 5.26-5.19 (m, 1H), 4.06 (q, J=7.0 Hz, 2H), 3.82-3.71 (m, 5H), 3.50-3.25 (m, 3H), 3.17-3.10 (m, 1H), 2.70-2.64 (m, 1H), 1.94-1.85 (m, 2H), 1.83-1.72 (m, 2H), 1.70-1.62 (m, 1H), 1.20 (t, J=7.1 Hz, 3H). LCMS (ESI) m/z calcd for C$_{25}$H$_{30}$N$_5$O$_9$P: 575.18. Found: 576.30 (M+1)$^+$.

Preparation of ethyl (S)-6'-methoxy-4'-(2-((phosphonooxy)methyl)-2H-indazole-7-carboxamido)-3',4'-dihydrospiro[piperidine-4,2'-pyrano[3,2-b]pyridine]-1-carboxylate, bis 2-amino-2-(hydroxymethyl)-1,3-propanediol salt

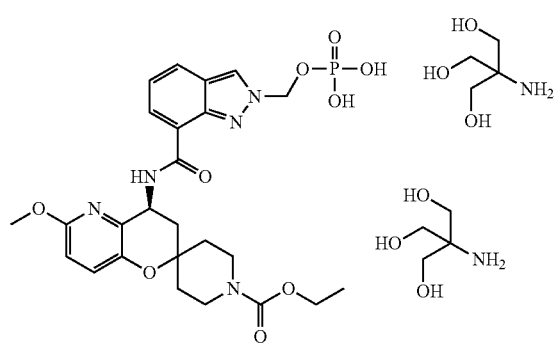 [SMILES: CCOC(=O)N1CCC2(CC1)C[C@H](NC(=O)c1cccc3cn(COP(=O)(O)O)nc13)c1nc(OC)ccc1O2 ; NC(CO)(CO)CO ; NC(CO)(CO)CO]

To a stirred suspension of (S)-ethyl 6'-methoxy-4'-(2-(phosphonooxymethyl)-2H-indazole-7-carboxamido)-3',4'-dihydrospiro[piperidine-4,2'-pyrano[3,2-b]pyridine]-1-carboxylate (60 mg, 0.104 mmol) in H$_2$O (0.5 mL) was added a solution of 2-amino-2-(hydroxymethyl)propane-1,3-diol (25.3 mg, 0.209 mmol) in H$_2$O (0.5 mL) and this was stirred at room temperature for 30 min. The reaction mixture was diluted with MeCN (3 ml) until cloudy and seeded with some crystalline. Stirring at ambient temperature was continued for 2 h. The solid was collected by filtration, washed with MeCN/water (9:1) and dried in vac. to provide the title compound (51 mg, 60% yield). $^1$H NMR (400 MHz, DMSO) δ 9.61 (d, J=5.5 Hz, 1H), 8.77 (s, 1H), 8.08 (d, J=7.0 Hz, 1H), 7.98 (d, J=8.2 Hz, 1H), 7.30 (d, J=8.8 Hz, 1H), 7.26-7.16 (m, 1H), 6.72 (d, J=8.8 Hz, 1H), 5.87 (d, J=10.8 Hz, 2H), 5.23-4.64 (m, 13H), 4.09-4.01 (m, 2H), 3.85-3.67 (m, 5H), 3.35 (s, 12H), 3.29-3.22 (m, 1H), 3.18-3.10 (m, 1H), 2.72-2.65 (m, 1H), 1.97-1.83 (m, 2H), 1.81-1.58 (m, 3H), 1.20 (t, J=7.0 Hz, 3H). LCMS (ESI) m/z Found: 576.30 (M+1)$^+$.

Example 57

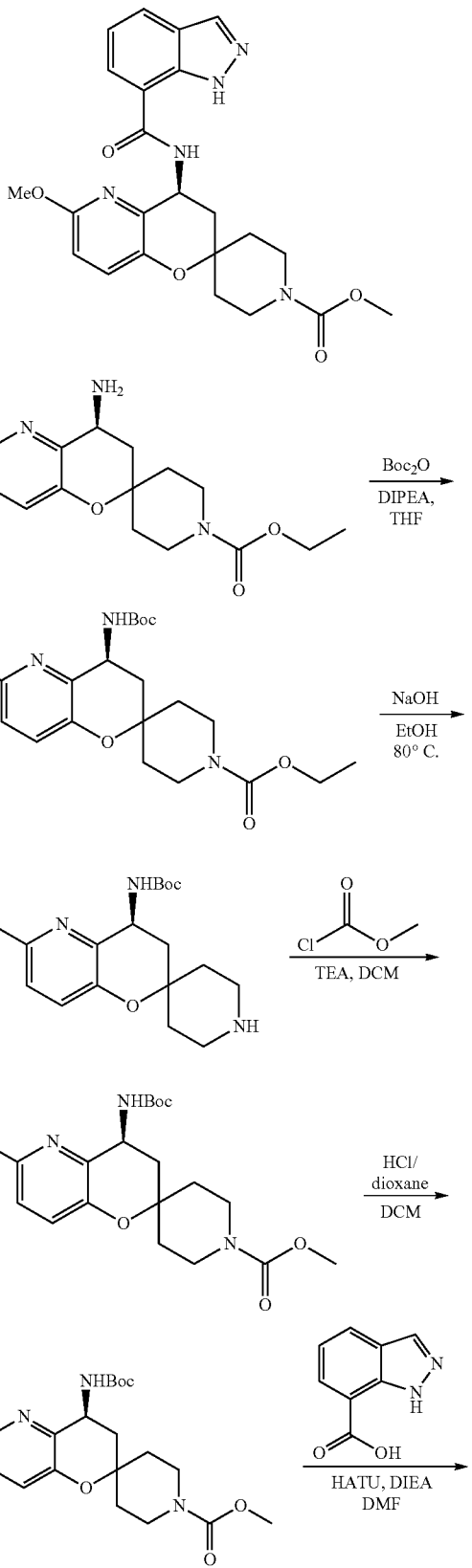

-continued

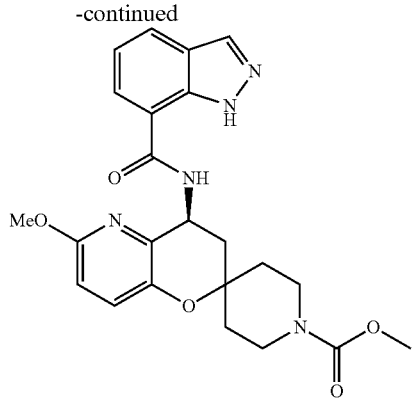

Preparation of ethyl (S)-4'-((tert-butoxycarbonyl) amino)-6'-methoxy-3',4'-dihydrospiro[piperidine-4, 2'-pyrano[3,2-b]pyridine]-1-carboxylate

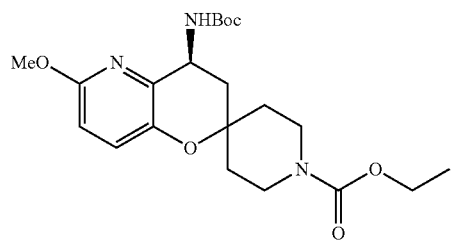 [SMILES: CCOC(=O)N1CCC2(CC1)C[C@H](NC(=O)OC(C)(C)C)c1nc(OC)ccc1O2]

To a stirred solution of ethyl (S)-4'-amino-6'-methoxy-3', 4'-dihydrospiro[piperidine-4,2'-pyrano[3,2-b]pyridine]-1-carboxylate (370 mg, 1.04 mmol) in THF (15 mL) was added Boc$_2$O (337 mg, 1.56 mmol) and DIPEA (536 mg, 4.15 mmol). After stirred at room temperature overnight, the resulting mixture was partitioned between EtOAc and H$_2$O. The layers were separated and the organic layer was washed with brine, dried over Na$_2$SO$_4$ and concentrated to give the crude product, which was purified by flash chromatography (silica gel, 0-30% EtOAc in PE) to afford the title compound (488 mg, 100% yield). LCMS (ESI) m/z calcd for C$_{21}$H$_{31}$N$_3$O$_6$: 421.22. Found: 422.30 (M+1)$^+$.

Preparation of tert-butyl (S)-(6'-methoxy-3',4'-dihydrospiro[piperidine-4,2'-pyrano[3,2-b]pyridin]-4'-yl) carbamate

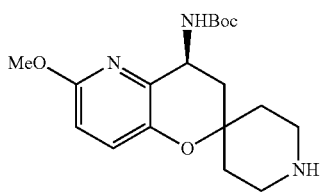

To a stirred solution of ethyl (S)-4'-((tert-butoxycarbonyl) amino)-6'-methoxy-3',4'-dihydrospiro[piperidine-4,2'-pyrano[3,2-b]pyridine]-1-carboxylate (488 mg, 1.06 mmol) in ethanol (20 mL) and was added NaOH (25 mol/L, 0.46 ml, 10.6 mmol) and this was stirred at 80° C. overnight. The resulting mixture was partitioned between DCM and H$_2$O. The layers were separated and the organic layer was washed with brine, dried over Na$_2$SO$_4$ and concentrated to afford the title compound (263 mg, 65% yield), which was used in the following step directly.

Preparation of methyl (S)-4'-((tert-butoxycarbonyl) amino)-6'-methoxy-3',4'-dihydrospiro[piperidine-4, 2'-pyrano[3,2-b]pyridine]-1-carboxylate

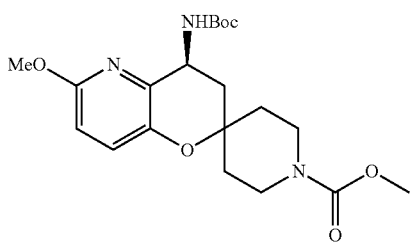 [SMILES: COC(=O)N1CCC2(CC1)C[C@H](NC(=O)OC(C)(C)C)c1nc(OC)ccc1O2]

At 0° C., to a stirred solution of tert-butyl (S)-(6'-methoxy-3',4'-dihydrospiro[piperidine-4,2'-pyrano[3,2-b]pyridin]-4'-yl)carbamate (263 mg, 0.754 mmol) and TEA (0.32 ml, 2.261 mmol) in DCM (3 mL) was added methyl carbonochloridate (0.09 ml, 1.13 mmol) portion wise. After stirred for 1 h, the resulting mixture was partitioned between DCM and water. The layers were separated and the organic layer was washed with brine, dried over Na$_2$SO$_4$ and concentrated. The residue was purified by column chromatography (silica gel, 0-50% EA in PE) to afford the title compound (240 mg, 78% yield). LCMS (ESI) m/z calcd for C$_{20}$H$_{29}$N$_3$O$_6$: 407.21. Found: 408.86 (M+1)$^+$.

Preparation of methyl (S)-4'-amino-6'-methoxy-3', 4'-dihydrospiro[piperidine-4,2'-pyrano[3,2-b]pyridine]-1-carboxylate

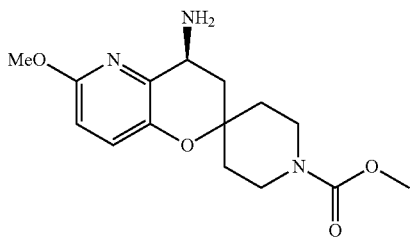 [SMILES: COC(=O)N1CCC2(CC1)C[C@H](N)c1nc(OC)ccc1O2]

To a stirring solution of methyl (S)-4'-((tert-butoxycarbonyl)amino)-6'-methoxy-3',4'-dihydrospiro[piperidine-4,2'-pyrano[3,2-b]pyridine]-1-carboxylate (160 mg, 0.393 mmol) in DCM (4 mL) was added HCl/dioxane (4 mol/L, 1 ml, 3.93 mmol) and this was stirred at room temperature for 1 hr. The reaction mixture was concentrated to afford the title compound as a tan solid (120 mg, 99% yield), which was used in the following step directly. LCMS (ESI) m/z calcd for C$_{15}$H$_{21}$N$_3$O$_4$: 307.15. Found: 308.72 (M+1)$^+$.

Preparation of methyl (S)-4'-(1H-indazole-7-carbox-amido)-6'-methoxy-3',4'-dihydrospiro[piperidine-4, 2'-pyrano[3,2-b]pyridine]-1-carboxylate

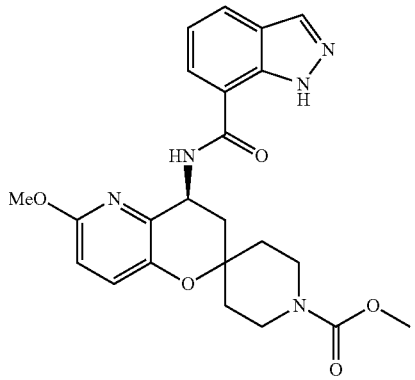 [SMILES: COC(=O)N1CCC2(CC1)C[C@H](NC(=O)c1cccc3cn[nH]c13)c1nc(OC)ccc1O2]

To a stirred solution of methyl (S)-4'-amino-6'-methoxy-3',4'-dihydrospiro[piperidine-4,2'-pyrano[3,2-b]pyridine]-1-carboxylate (70 mg, 0.227 mmol), 1H-indazole-7-carboxylic acid (44 mg, 0.273 mmol) and DIPEA (0.2 ml, 1.136 mmol) in DMF (3 mL) was added HATU (113 mg, 0.295 mmol) and this was stirred at room temperature for 1 hr. The reaction mixture was partitioned between EtOAc and water. The layers were separated and the organic layer was washed with brine, dried over $Na_2SO_4$ and concentrated to give the crude product, which was purified by Prep. HPLC (C18, 40-100% MeCN in $H_2O$ with 0.5% formic acid) to afford the title compound (62 mg, 61% yield) as a white solid. $^1$H NMR (400 MHz, DMSO) δ 13.10 (s, 1H), 8.86 (s, 1H), 8.16 (s, 1H), 8.00-7.88 (m, 2H), 7.28 (d, J=8.8 Hz, 1H), 7.22-7.15 (m, 1H), 6.69 (d, J=8.7 Hz, 1H), 5.43-5.27 (m, 1H), 3.87-3.71 (m, 2H), 3.62 (d, J=11.2 Hz, 6H), 3.31-3.23 (m, 1H), 3.18-3.06 (m, 1H), 2.36-2.24 (m, 1H), 2.13-2.03 (m, 1H), 1.92-1.80 (m, 2H), 1.79-1.70 (m, 1H), 1.69-1.60 (m, 1H). LCMS (ESI) m/z calcd for $C_{23}H_{25}N_5O_5$: 451.19. Found: 452.35 $(M+1)^+$.

Example 58: (S)-ethyl 6'-bromo-4'-(2-((phosphonooxy)methyl)-2H-indazole-7-carboxamido)-3',4'-dihydrospiro[piperidine-4,2'-pyrano[2,3-c]pyridine]-1-carboxylate

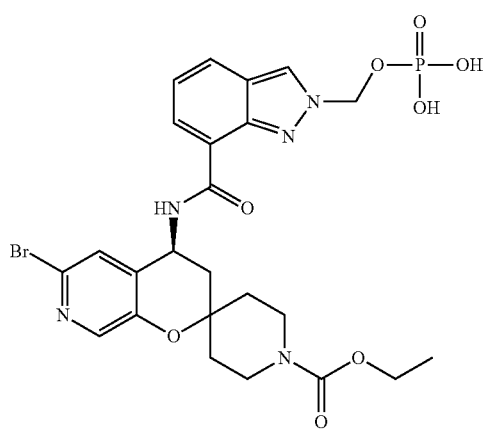 [SMILES: CCOC(=O)N1CCC2(CC1)C[C@H](NC(=O)c1cccc3cn(COP(=O)(O)O)nc13)c1cc(Br)ncc1O2]

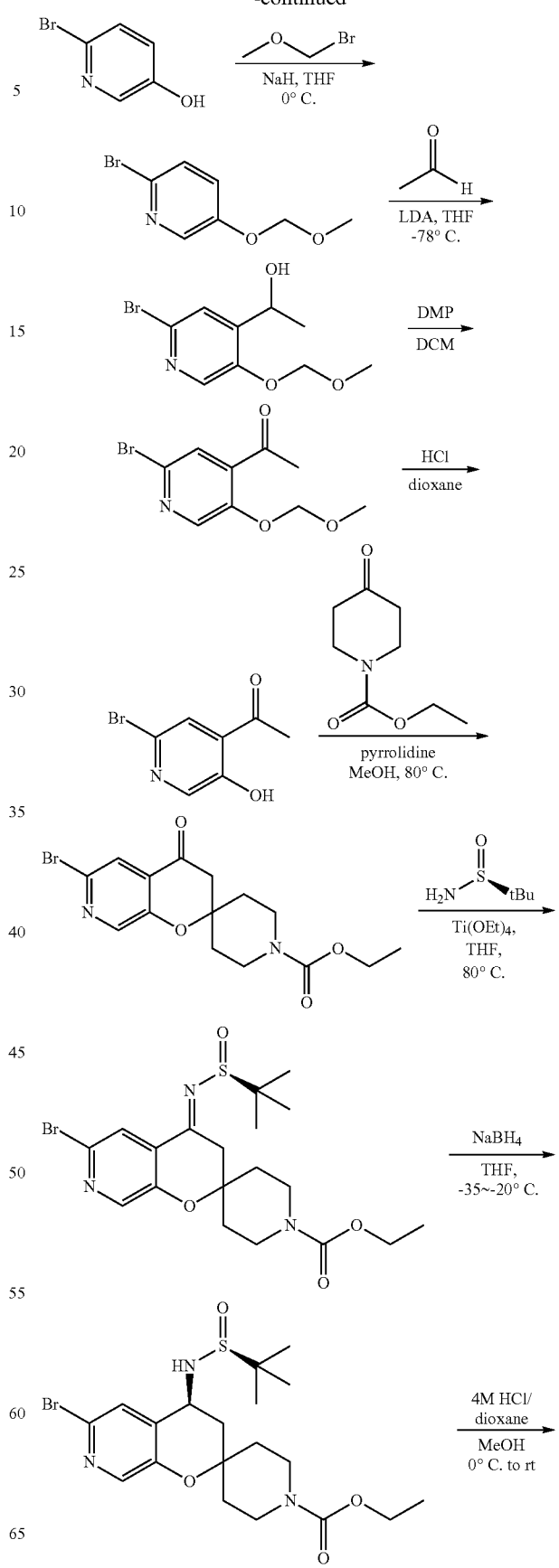

-continued

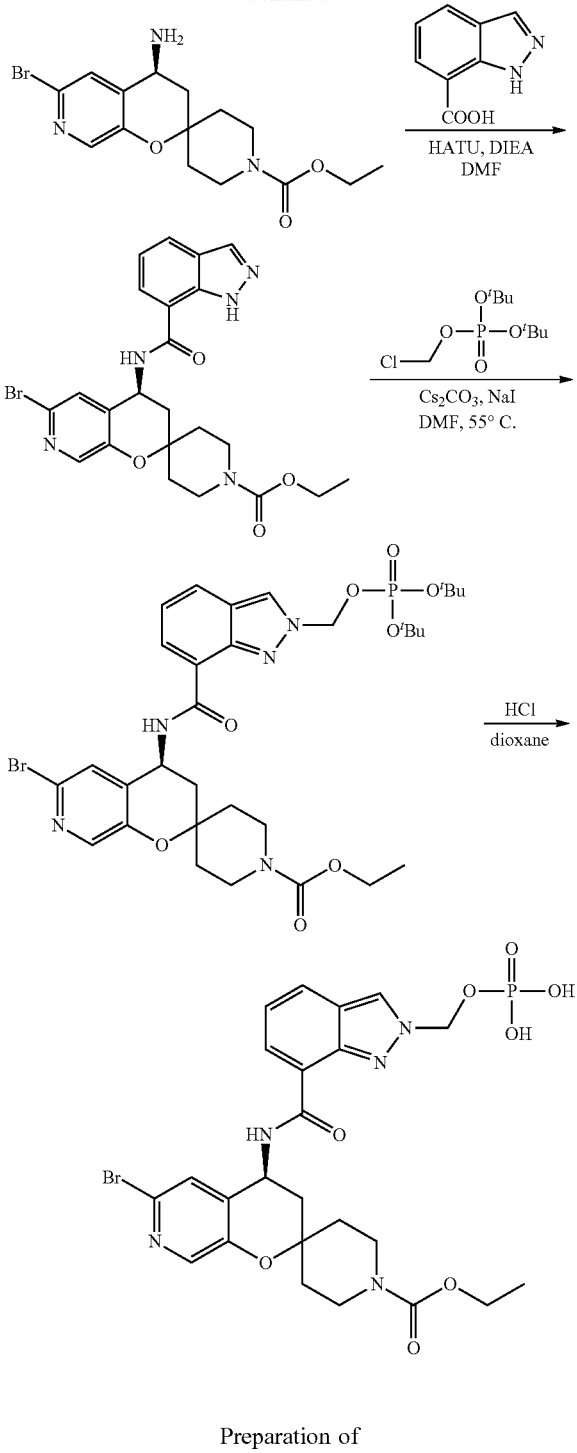

Preparation of 2-bromo-5-(methoxymethoxy)pyridine

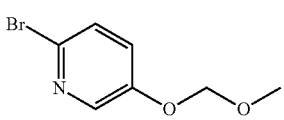

At 0° C., to a solution of 6-bromopyridin-3-ol (25 g, 144 mmol) in THF (300 mL) was added NaH (60% in mineral oil) (7.5 g, 187 mmol) portion wise. After stirred at this temperature for 1 h, to the reaction mixture was added bromo(methoxy)methane (23.3 g, 187 mmol). After stirred at room temperature for another 2 h, the resulting mixture was partitioned between EtOAc and saturated aq. NH$_4$Cl. The layers were separated and the organic layer was washed with brine, dried over Na$_2$SO$_4$ and concentrated to give the crude product, which was purified by flash chromatography (silica gel, 0-30% EtOAc in PE) to afford the title compound (24 g, 77% yield). LCMS (ESI) m/z calcd for C$_7$H$_8$BrNO$_2$: 216.97. Found: 218.09/220.08 (M/M+2)$^+$.

Preparation of 1-(2-bromo-5-(methoxymethoxy)pyridin-4-yl)ethan-1-ol

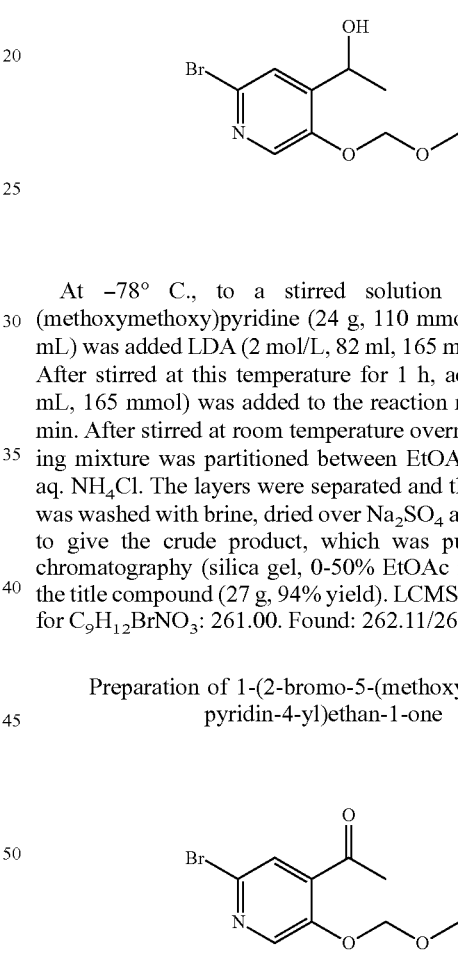

At −78° C., to a stirred solution of 2-bromo-5-(methoxymethoxy)pyridine (24 g, 110 mmol) in THF (300 mL) was added LDA (2 mol/L, 82 ml, 165 mmol) drop wise. After stirred at this temperature for 1 h, acetaldehyde (10 mL, 165 mmol) was added to the reaction mixture over 10 min. After stirred at room temperature overnight, the resulting mixture was partitioned between EtOAc and saturated aq. NH$_4$Cl. The layers were separated and the organic layer was washed with brine, dried over Na$_2$SO$_4$ and concentrated to give the crude product, which was purified by flash chromatography (silica gel, 0-50% EtOAc in PE) to afford the title compound (27 g, 94% yield). LCMS (ESI) m/z calcd for C$_9$H$_{12}$BrNO$_3$: 261.00. Found: 262.11/264.11 (M/M+2)$^+$.

Preparation of 1-(2-bromo-5-(methoxymethoxy)pyridin-4-yl)ethan-1-one

To a solution of 1-(2-bromo-5-(methoxymethoxy)pyridin-4-yl)ethan-1-ol (27 g, 103 mmol) in DCM (600 mL) was added DMP (110 g, 259 mmol) at 0° C. The reaction mixture was allowed to warm to room temperature and stirred for 3 h. The solid was filtered off and the filtrate was concentrated to give the crude product, which was purified by flash chromatography (silica gel, 0-30% EtOAc in PE) to afford the title compound (22 g, 82% yield). LCMS (ESI) m/z calcd for C$_9$H$_{10}$BrNO$_3$: 258.98. Found: 260.11/262.10 (M/M−2)+.

Preparation of 1-(2-bromo-5-hydroxypyridin-4-yl)ethan-1-one

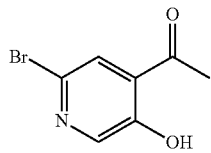

At 0° C., to a stirred solution of 1-(2-bromo-5-(methoxymethoxy)pyridin-4-yl)ethanone (22 g, 84.6 mmol) in dioxane (300 mL) was added HCl/dioxane (4 mol/L, 64 ml, 254 mmol). After stirred at temperature overnight, the reaction mixture was neutralized with 4N NaOH to pH 7-8 and extracted with EA. The layers were separated and the organic layer was washed with brine, dried over $Na_2SO_4$ and concentrated to afford the title compound (16.4 g, 90% yield). LCMS (ESI) m/z calcd for $C_7H_6BrNO_2$: 214.96. Found: 216.06/218.07 (M/M−2)$^+$.

Preparation of ethyl 6'-bromo-4=oxo-3',4'-dihydrospiro[piperidine-4,2=pyrano[2,3-c]pyridine]-1-carboxylate

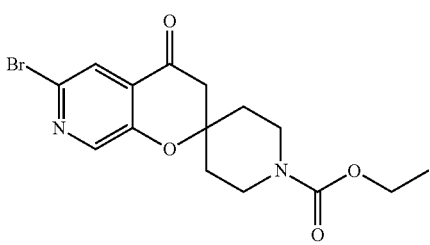 [SMILES: CCOC(=O)N1CCC2(CC1)CC(=O)c1cc(Br)ncc1O2]

To a stirring solution of 1-(2-bromo-5-hydroxypyridin-4-yl)ethan-1-one (16 g, 74.8 mmol) in methanol (300 mL) was added pyrrolidine (9 g, 126 mmol) and ethyl 4-oxopiperidine-1-carboxylate (16.6 g, 96.9 mmol) at room temperature and this was heated to 80° C. After stirred for 14 h, the resulting mixture was partitioned between EtOAc and $H_2O$. The layers were separated and the organic layer was washed with brine, dried over $Na_2SO_4$ and concentrated to give the crude product, which was purified by flash chromatography (silica gel, 0-50% EtOAc in PE) to afford the title compound (24 g, 87% yield). LCMS (ESI) m/z calcd for $C_{15}H_{17}BrN_2O_4$: 368.04. Found: 369.10/371.10 (M/M+2)$^+$.

Preparation of ethyl (S)-6'-bromo-4'-(((S)-tert-butylsulfinyl)amino)-3',4'-dihydrospiro[piperidine-4,2'-pyrano[2,3-c]pyridine]-1-carboxylate

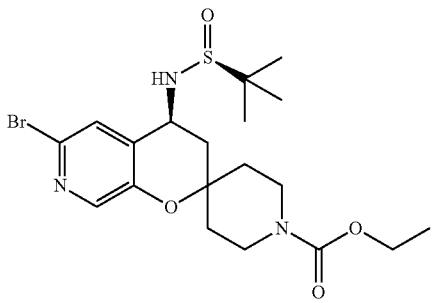

To a stirred solution of 6'-bromo-4'-oxo-3',4'-dihydrospiro[piperidine-4,2'-pyrano[2,3-c]pyridine]-1-carboxylate (14 g, 37.9 mmol) and (S)-2-methylpropane-2-sulfinamide (9.2 g, 75.9 mmol) in THF (300 mL) was added and $Ti(OEt)_4$ (26 g, 113.9 mmol). The resulting mixture was heated at 80° C. under a nitrogen atmosphere. After 20 hours, the solution was cooled to RT and then to −35° C. The solution was treated with $NaBH_4$ (7.2 g, 190 mmol) and this was stirred at −35° C. for 30 minutes. Then the mixture was allowed to warm to −20° C. and stirred at this temperature overnight. LCMS indicated complete conversion of the imine intermediate to the desired amine product as a 92:8 mixture of diastereomers. The cloudy solution was cooled to 0° C. and quenched by slow addition of MeOH until gas evolution ceased. The resulting mixture was treated with saturated aqueous brine to afford a thick, light yellow suspension. The solid was removed by filtration through a medium fritted funnel. The filtrate was washed with saturated brine (1×), dried over $Na_2SO_4$, and concentrated at reduced pressure. The residue was purified by flash chromatography (silica gel, 0-30% EtOAc in DCM) to afford the title compound (5.7 g, 32% yield). LCMS (ESI) m/z calcd for $C_{19}H_{28}BrN_3O_4S$: 473.10. Found: 474.22/476.23 (M/M+2)$^+$.

Preparation of ethyl (S)-4'-amino-6'-bromo-3',4'-dihydrospiro[piperidine-4,2'-pyrano[2,3-c]pyridine]-1-carboxylate

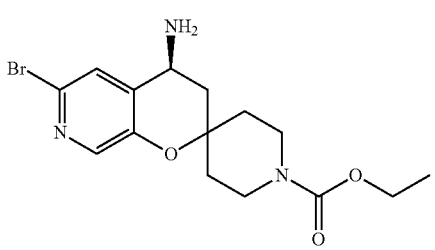 [SMILES: CCOC(=O)N1CCC2(CC1)C[C@H](N)c1cc(Br)ncc1O2]

To a stirred solution of ethyl (S)-6'-bromo-4'-(((S)-tert-butylsulfinyl)amino)-3',4'-dihydrospiro[piperidine-4,2'-pyrano[2,3-c]pyridine]-1-carboxylate (5.7 g, 12.0 mmol) in MeOH (50 mL) was added HCl/dioxane (4 mol/L, 6 ml, 24.0 mmol) drop wise. The solution was then allowed to warm to RT. After 3 hours, the solution was concentrated to dryness at reduced pressure. The residue was redissolved in MeOH and concentrated again to dryness to afford the title compound as a tan solid (4.5 g, 100% yield). LCMS (ESI) m/z calcd for $C_{15}H_{20}BrN_3O_3$: 369.07. Found: 370.10/372.11 (M/M+2)[30].

Preparation of ethyl (S)-6'-bromo-4'-(1H-indazole-7-carboxamido)-3',4'-dihydrospiro[piperidine-4,2'-pyrano[2,3-c]pyridine]-1-carboxylate

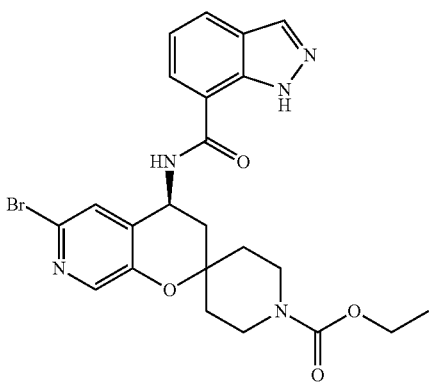 [SMILES: CCOC(=O)N1CCC2(CC1)C[C@H](NC(=O)c1cccc3cn[nH]c13)c1cc(Br)ncc1O2]

To a stirred solution of ethyl (S)-4'-amino-6'-bromo-3',4'-dihydrospiro[piperidine-4,2'-pyrano[2,3-c]pyridine]-1-carboxylate (4.5 g, 11.1 mmol) and 1H-indazole-7-carboxylic acid (1.93 g, 11.9 mmol) in DMF (100 mL) and was added DIPEA (8 mL, 44.4 mmol) followed by HATU (5 g, 13.1 mmol). After stirred at room temperature for 3 hours, the reaction mixture was partitioned between EtOAc and saturated aq. NaHCO₃. The layers were separated and the organic layer was washed with brine, dried over Na₂SO₄ and concentrated to give the crude product, which was purified by flash chromatography (silica gel, 0-60% EtOAc in PE) to afford the title compound (3.9 g, 64% yield). ¹H NMR (400 MHz, CDCl₃) δ 11.90 (br, 1H), 8.14 (s, 1H), 8.04-7.96 (m, 2H), 7.72 (d, J=6.8 Hz, 1H), 7.40 (s, 1H), 7.22 (t, J=7.7 Hz, 1H), 6.92 (br, 1H), 5.73-5.63 (m, 1H), 4.14 (q, J=7.1 Hz, 2H), 4.05-3.88 (m, 2H), 3.43-3.28 (m, 1H), 3.19-3.04 (m, 1H), 2.41-2.32 (m, 1H), 1.96-1.88 (m, 2H), 1.79-1.63 (m, 3H), 1.27 (t, J=7.1 Hz, 3H). LCMS (ESI) m/z calcd for $C_{23}H_{24}BrN_5O_4$: 513.10. Found: 514.18/516.17 (M/M+2)⁺.

Preparation of ethyl (S)-6'-bromo-4'-(2-(((di-tert-butoxyphosphoryl)oxy)methyl)-2H-indazole-7-carboxamido)-3',4'-dihydrospiro[piperidine-4,2'-pyrano[2,3-c]pyridine]-1-carboxylate

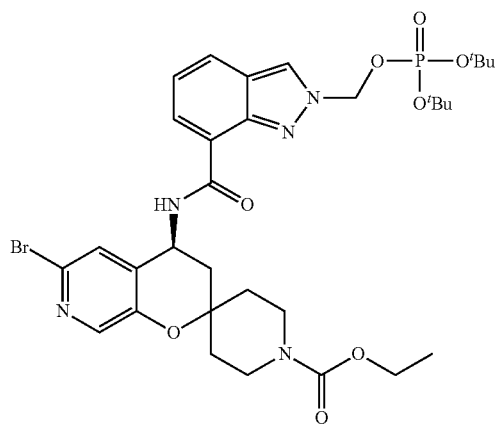 [SMILES: CCOC(=O)N1CCC2(CC1)C[C@H](NC(=O)c1cccc3cn(COP(=O)(OC(C)(C)C)OC(C)(C)C)nc13)c1cc(Br)ncc1O2]

To a stirred suspension of (S)-ethyl 6'-bromo-4'-(1H-indazole-7-carboxamido)-3',4'-dihydrospiro[piperidine-4,2'-pyrano[2,3-c]pyridine]-1-carboxylate (800 mg, 1.55 mmol), Cs₂CO₃ (1.52 g, 4.66 mmol) and NaI (255 mg, 1.70 mmol) in DMF (20 mL) and was added di-tert-butyl chloromethyl phosphate (604 mg, 2.34 mmol) After stirred at 55° C. for 5 hours, the resulting mixture was partitioned between EtOAc and water. The organic layer was separated and washed with saturated aqueous NaCl (2×), dried over Na₂SO₄ and concentrated to dryness at reduced pressure to afford the title compound (1.25 g, 100% yield) as a yellow gum. LCMS (ESI) m/z calcd for $C_{32}H_{43}BrN_5O_8P$: 735.20. Found: 736.40/738.36 (M/M+2)⁺.

Preparation of ethyl (S)-6'-bromo-4'-(2-((phosphonooxy)methyl)-2H-indazole-7-carboxamido)-3',4'-dihydrospiro[piperidine-4,2'-pyrano[2,3-c]pyridine]-1-carboxylate

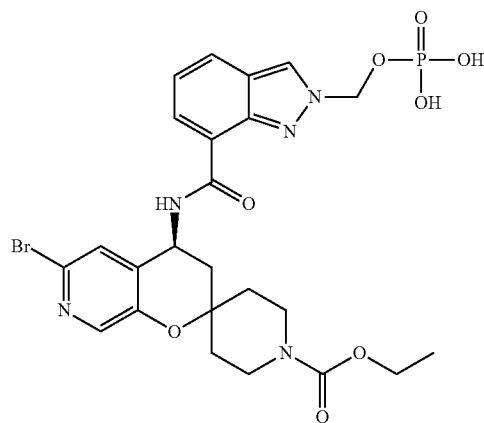 [SMILES: CCOC(=O)N1CCC2(CC1)C[C@H](NC(=O)c1cccc3cn(COP(=O)(O)O)nc13)c1cc(Br)ncc1O2]

To a stirred solution of ethyl (S)-6'-bromo-4'-(2-(((di-tert-butoxyphosphoryl)oxy)methyl)-2H-indazole-7-carboxamido)-3',4'-dihydrospiro[piperidine-4,2'-pyrano[2,3-c]pyridine]-1-carboxylate (1.25 g, 1.70 mmol) in DCM (12 mL) was added HCl/dioxane (4 mol/L, 4.2 ml, 16.98 mmol)). After stirred at 25° C. for 2 hours, the resulting mixture was concentrated at reduced pressure to afford a residue, which was purified by Glison (C$_{18}$, 20-100% MeCN in H$_2$O) to afford the title compound (530 mg, 50% yield). $^1$H NMR (400 MHz, DMSO) δ 9.45 (d, J=8.1 Hz, 1H), 8.77 (s, 1H), 8.15-8.00 (m, 3H), 7.42 (s, 1H), 7.29 (dd, J=8.3, 7.1 Hz, 1H), 6.20-6.07 (m, 2H), 5.48-5.39 (m, 1H), 4.05 (q, J=7.0 Hz, 2H), 3.94-3.39 (m, 4H), 3.36-3.28 (m, 1H), 3.16-3.07 (m, 1H), 2.38-2.30 (m, 1H), 2.17-2.08 (m, 1H), 1.90-1.75 (m, 3H), 1.71-1.63 (m, 1H), 1.19 (t, J=7.1 Hz, 3H). LCMS (ESI) m/z calcd for C$_{24}$H$_{27}$BrN$_5$O$_8$P: 623.08. Found: 624.20/626.20 (M/M+2)$^+$.

Example 59

7.20 (t, J=7.6 Hz, 1H), 6.87 (d, J=8.4 Hz, 1H), 5.52-5.43 (m, 1H), 5.31 (s, 1H), 4.83 (s, 2H), 4.05 (q, J=7.0 Hz, 2H), 3.87-3.73 (m, 2H), 3.32-3.19 (m, 1H), 3.14-3.00 (m, 1H), 2.28-2.17 (m, 1H), 2.07-1.98 (m, 1H), 1.87-1.70 (m, 3H), 1.67-1.58 (m, 1H), 1.19 (t, J=7.1 Hz, 3H). LCMS (ESI) m/z calcd for C$_{25}$H$_{27}$BrN$_4$O$_5$: 542.12. Found: 543.36/545.36 (M/M+2)$^+$.

Example 60

Preparation of (S)-4-((7-(((6-bromo-1'-(ethoxycarbonyl)spiro[chromane-2,4'-piperidin]-4-yl)carbamoyl)-1H-indazol-3-yl)methoxy)-4-oxobutanoic acid

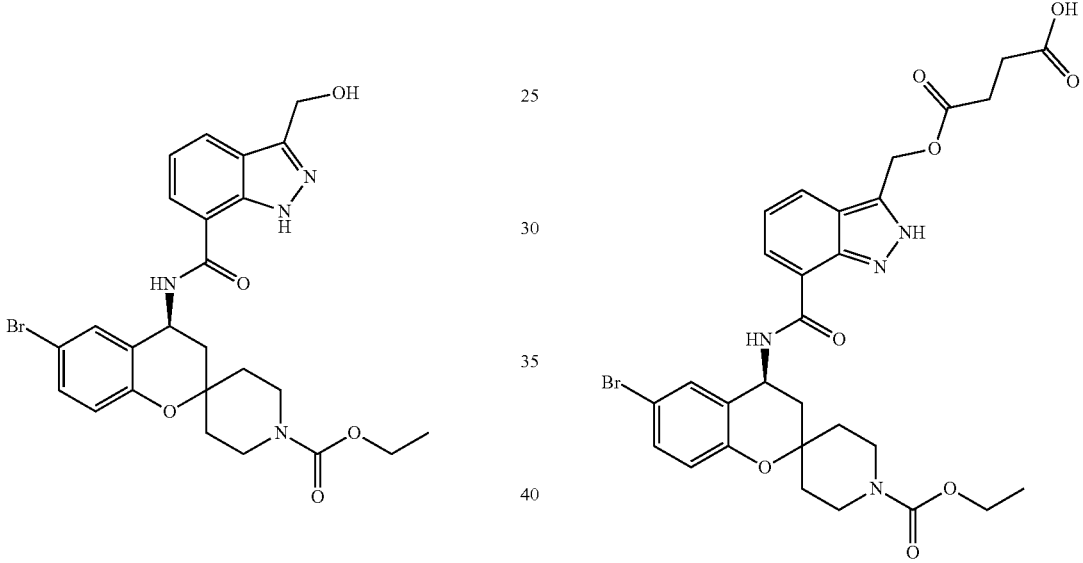

Preparation of ethyl (S)-6-bromo-4-(3-(hydroxymethyl)-1H-indazole-7-carboxamido) spiro[chromane-2,4'-piperidine]-1'-carboxylate A suspension of ethyl (S)-6-bromo-4-(1H-indazole-7-carboxamido) spiro[chromane-2,4'-piperidine]-1'-carboxylate (1.0 g, 1.95 mmol), Cs$_2$CO$_3$ (952 mg, 2.92 mmol) and 37% formalin (5 mL) in Ethanol (19 mL) and THF (1 mL) was stirred at 85° C. for 5 days. After cooling down to room temperature, the resulting reaction mixture was partitioned between ethyl acetate and H$_2$O. The organic layer was washed with brine, dried over Na$_2$SO$_4$ and concentrated under reduced pressure to give a crude product, which was purified by preparative HPLC (C18, 30-100% MeCN in H$_2$O with 0.5% formic acid) to afford the title compound as a white solid (300 mg, 28% yield). $^1$H NMR (400 MHz, DMSO) δ 12.94 (s, 1H), 9.07 (d, J=8.0 Hz, 1H), 8.08 (d, J=7.9 Hz, 1H), 7.97 (d, J=7.2 Hz, 1H), 7.41-7.29 (m, 2H), At 0° C., a stirred solution of ethyl (S)-6-bromo-4-(3-(hydroxymethyl)-1H-indazole-7-carboxamido)spiro[chromane-2,4'-piperidine]-1'-carboxylate (80 mg, 0.147 mmol) and DMAP (5 mg, 0.04 mmol) in pyridine (1 mL) was added dihydrofuran-2,5-dione (73 mg, 0.736 mmol) and this was stirred at room temperature overnight. The reaction mixture was concentrated under reduced pressure to give the crude product, which was purified by preparative HPLC (C18, 20-100% MeCN in H$_2$O with 0.5% formic acid) to afford the title compound (28 mg, 29%) as a white solid. $^1$H NMR (400 MHz, DMSO) δ 13.25 (s, 1H), 12.29 (br, 1H), 9.09 (d, J=8.5 Hz, 1H), 8.04-7.96 (m, 2H), 7.37-7.30 (m, 2H), 7.25 (t, J=7.7 Hz, 1H), 6.87 (d, J=8.5 Hz, 1H), 5.49-5.38 (m, 3H), 4.05 (q, J=7.0 Hz, 2H), 3.85-3.73 (m, 2H), 3.29-3.23 (m, 1H), 3.11-3.03 (m, 1H), 2.60-2.53 (m, 2H), 2.49-2.46 (m, 2H), 2.25-2.19 (m, 1H), 2.05-1.98 (m, 1H), 1.86-1.72 (m, 3H), 1.66-1.59 (m, 1H), 1.19 (t, J=7.1 Hz, 3H). LCMS (ESI) m/z calcd for C$_{29}$H$_{31}$BrN$_4$O$_8$: 642.13. Found: 643.29/645.24 (M/M-2)$^+$.

Example 61

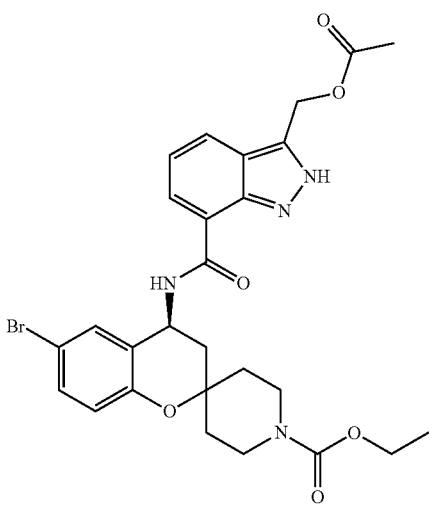 [SMILES: CCOC(=O)N1CCC2(CC1)C[C@H](NC(=O)c1cccc3c(COC(C)=O)[nH]nc13)c1cc(Br)ccc1O2]

Preparation of ethyl (S)-4-(3-(acetoxymethyl)-1H-indazole-7-carboxamido)-6-bromo spiro[chromane-2,4'-piperidine]-1'-carboxylate At 0° C., to a solution of ethyl (S)-6-bromo-4-(3-(hydroxymethyl)-1H-indazole-7-carboxamido)spiro[chromane-2,4'-piperidine]-1'-carboxylate (86 mg, 0.158 mmol), TEA (0.65 mL, 0.474 mmol) and DMAP (7.0 mg, 0.057 mmol) in dry DMF (1 mL) was added acetyl chloride (15 mg, 1.9 mmol) drop wise. After stirred at room temperature overnight, the mixture was concentrated under reduced pressure to give the crude product, which was purified by preparative HPLC (C18, 30-100% MeCN in $H_2O$ with 0.5% formic acid) to afford the title compound as a white solid (20 mg, 21%). $^1$H NMR (400 MHz, DMSO) δ 13.26 (s, 1H), 9.09 (d, J=7.9 Hz, 1H), 8.01 (dd, J=15.6, 7.6 Hz, 2H), 7.38-7.31 (m, 2H), 7.25 (t, J=7.7 Hz, 1H), 6.87 (d, J=8.6 Hz, 1H), 5.51-5.38 (m, 3H), 4.05 (q, J=7.1 Hz, 2H), 3.86-3.74 (m, 2H), 3.30-3.25 (m, 1H), 3.13-3.05 (m, 1H), 2.25-2.19 (m, 1H), 2.08-1.98 (m, 4H), 1.86-1.72 (m, 3H), 1.66-1.58 (m, 1H), 1.19 (t, J=7.1 Hz, 3H). LCMS (ESI) m/z calcd for $C_{27}H_{29}BrN_4O_6$: 584.13. Found: 585.32/587.31 $(M/M-2)^+$.

PBMC IDO1 Assay:

Data shown in Table 1. Compounds of the present invention were tested via high-throughput cellular assays utilizing detection of kynurenine via mass spectrometry and cytotoxicity as end-points. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from *Salmonella minnesota* (LPS) (Invivogen, San Diego, Calif.) to induce the expression of indoleamine 2,3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 μL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 μL of DMSO in the presence of unstimulated (−IFN-γ/−LPS) PBMCs for the mass spectrometry assay or 0.5 μL of DMSO in the absence of cells for the cytotoxicity assay, and high control wells (100% kynurenine or 0% cytotoxicity) contained 0.5 μL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 1,000,000 cells/mL in the supplemented RPMI 1640 medium. 50 μL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 μL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 μL were added to each plate well. After a twenty-minute incubation at room temperature, luminescence was read on an EnVision® Multilabel Reader (PerkinElmer Inc., Waltham, Mass.). For the mass spectrometry assay, 10 μL of supernatant from each well of the compound-treated plates were added to 40 μL of acetonitrile, containing 10 μM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 μL from each well of the acetonitrile extraction plates were added to 90 μL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C1−C2))), where U was the unknown value, C1 was the average of the high (0% cytotoxicity) control wells and C2 was the average of the low (100% cytotoxicity) control wells.

Curve fitting was performed with the equation $y=A+((B-A)/(1+(10^y/10^C)^D))$, where A was the minimum response, B was the maximum response, C was the $\log(XC_{50})$ and D was the Hill slope. The results for each test compound were recorded as pIC50 values for the mass spectrometry assay and as pCC50 values for the cytoxicity assay (−C in the above equation).

TABLE 1

| example number | IDO1 PBMC pIC$_{50}$ |
| --- | --- |
| 1 | 8.3 |
| 2 | 8.3 |
| 3 | 6.6 |
| 4 | 8.4 |
| 5 | 8.3 |
| 6 | 8.3 |
| 7 | 8.1 |
| 8 | 8.3 |
| 9 | 8 |
| 10 | 7.9 |
| 11 | 7.8 |
| 12 | 7.8 |
| 13 | 7.7 |
| 14 | 7.7 |
| 15 | 7.5 |
| 16 | 7.5 |
| 17 | 7.4 |
| 18 | 7.4 |
| 19 | 7.3 |
| 20 | 7.2 |
| 21 | 7.1 |
| 22 | 7.1 |
| 23 | 7.1 |
| 24 | 7 |
| 25 | 7 |
| 26 | 6.9 |
| 27 | 6.8 |
| 28 | 6.8 |
| 29 | 6.8 |
| 30 | 6.7 |
| 31 | 6.7 |
| 32 | 6.7 |
| 33 | 6.7 |
| 34 | 6.6 |
| 35 | 6.6 |
| 36 | 6.6 |
| 37 | 6.6 |
| 38 | 6.4 |
| 39 | 6.4 |
| 40 | 6.4 |
| 41 | 6.3 |
| 42 | 6.3 |
| 43 | 6.2 |
| 44 | 6.2 |
| 45 | 6.1 |
| 46 | 6.1 |
| 50 | 6.9 |
| 51 | 8 |
| 52 | 8.4 |
| 53 | 6.2 |
| 54 | 7.7 |
| 55 | 6.9 |
| 56 | 7.1 |
| 57 | 8 |
| 58 | 6.3 |
| 59 | 9.1 |
| 60 | 8.9 |
| 61 | 8.9 |

What is claimed is:

1. A compound of Formula I

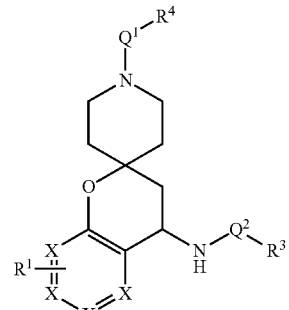

Formula I or a pharmaceutically acceptable salt thereof wherein:
each X is CH or one X is N and the other 3 are CH;
$Q^1$ is a bond (i.e. is absent), —C(O)C—, or C(O)—;
$Q^2$ is a bond (i.e. is absent) or C(O)—;
$R^1$ is absent, halogen, $C_{1-3}$alkylOH, or C(O)OC$_{1-3}$alkyl;
$R^3$ is $C_{5-9}$aryl, or 5-9 membered heteroaryl, wherein aryl and heteroaryl include bicycles and heteroaryl contains 1-3 hetero atoms selected from O, S, and N, and wherein $R^3$ may optionally be substituted with a substituent selected from halogen, OH, $C_{1-3}$alkyl, OC$_{1-3}$alkyl, $C_{1-3}$fluoroalkyl, CN, and NH$_2$; and
$R^4$ is H, $C_{1-3}$haloalkyl, phenyl or $C_{1-6}$alkyl.

2. A compound or salt according to claim 1 wherein each X is CH.

3. A compound or salt according to claim 1 wherein $Q^1$ is C(O)O.

4. A compound or salt according to claim 1 wherein $Q^2$ is C(O).

5. A compound or salt according to claim 1 wherein $R^1$ is Br, OCH$_3$, or is absent.

6. A compound or salt according to claim 1 wherein $R^3$ is indole, benzodiazole, phenyl, pyridyl, diazole, or pyrimidine, and wherein $R^3$ may optionally be substituted with a substituent selected from halogen, OH, $C_{1-3}$alkyl, OC$_{1-3}$alkyl, $C_{1-3}$fluoroalkyl, CN, and NH$_2$.

7. A compound or salt according to claim 6 wherein $R^3$ is indole or benzodiazole, and wherein $R^3$ may optionally be substituted with a substituent selected from halogen, OH, $C_{1-3}$alkyl, OC$_{1-3}$alkyl, $C_{1-3}$fluoroalkyl, CN, and NH$_2$.

8. A compound or salt according to claim 7 wherein $R^3$ is unsubstituted indazole.

9. A compound or salt according to claim 1 wherein $R^4$ is H, $C_{1-4}$alkyl, CF$_3$, or phenyl.

10. A compound or salt according to claim 9 wherein $R^4$ is $C_{1-4}$alkyl.

11. A compound or salt according to claim 1 wherein each X is CH; $Q^1$ is C(O)O; $Q^2$ is C(O); $R^1$ is Br, OCH$_3$, or is absent; $R^3$ is indole, benzodiazole, phenyl, pyridyl, diazole, or pyrimidine, and wherein $R^3$ may optionally be substituted with a substituent selected from halogen, OH, $C_{1-3}$alkyl, OC$_{1-3}$alkyl, $C_{1-3}$fluoroalkyl, CN, and NH$_2$; and $R^4$ is H, $C_{1-4}$alkyl, CF$_3$, or phenyl.

12. A pharmaceutical composition comprising a compound or salt according to claim 1.

13. A method of treating a disease or condition that would benefit from inhibition of IDO1, wherein said disease or condition is chronic viral infection; chronic bacterial infections; cancer; sepsis; or a neurological disorder, comprising the step of administration of a composition according to claim 12.

14. The method of claim 13 wherein in said disease or condition, biomarkers of IDO activity are elevated.

15. The method of claim 13 wherein said biomarkers are plasma kynurenine or the plasma kynurenine/tryptophan ratio.

16. The method of claim 13 wherein said chronic viral infections are those involving HIV, HBV, or HCV; said chronic bacterial infections are tuberculosis or prosthetic joint infection; and said neurological disorders are major depressive disorder, Huntington's disease, or Parkinson's disease.

17. The method of claim 16 wherein said disease or condition is inflammation associated with HIV infection; chronic viral infections involving hepatitis B virus or hepatitis C virus; cancer; or sepsis.

* * * * *